(12) United States Patent
Das et al.

(10) Patent No.: US 8,779,156 B2
(45) Date of Patent: Jul. 15, 2014

(54) ANALOGUES FOR THE TREATMENT OR PREVENTION OF FLAVIVIRUS INFECTIONS

(71) Applicant: Vertex Pharmaceuticals Incorporated, Cambridge, MA (US)

(72) Inventors: Sanjoy Kumar Das, Pierrefonds (CA); Youssef L. Benanni, Lorriane (CA); Laval Chan Chun Kong, Kirkland (CA); John Maxwell, Hingham, MA (US); T. Jagadeeswar Reddy, Pierrefonds (CA); Constantin Yannopoulos, Notre-Dame de l'Ile Perrot (CA); Bingcan Liu, Montreal (CA); Caroline Cadilhac, Montreal (CA); Simon Giroux, Cambridge, MA (US); James A. Henderson, Cambridge, MA (US); Real Denis, Laval (CA); Louis Vaillancourt, Mascouche (CA); Oswy Z. Pereira, Kirkland (CA); Carl Poisson, Montreal (CA); Guy Falardeau, Laval (CA); Mark A. Morris, Somerville, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 13/625,135

(22) Filed: Sep. 24, 2012

(65) Prior Publication Data
US 2013/0090351 A1    Apr. 11, 2013

Related U.S. Application Data

(63) Continuation of application No. PCT/US2011/029825, filed on Mar. 24, 2011.

(60) Provisional application No. 61/316,988, filed on Mar. 24, 2010.

(51) Int. Cl.
| | |
|---|---|
| *C07D 235/18* | (2006.01) |
| *C07D 235/20* | (2006.01) |
| *C07D 235/22* | (2006.01) |
| *C07D 235/06* | (2006.01) |

(52) U.S. Cl.
CPC ............ *C07D 235/18* (2013.01); *C07D 235/20* (2013.01); *C07D 235/22* (2013.01); *C07D 235/06* (2013.01)
USPC .................................... 548/305.4; 548/306.1

(58) Field of Classification Search
CPC .. C07D 235/18; C07D 235/20; C07D 235/22; C07D 235/06
USPC ............ 514/394, 303, 44.5; 548/305.4, 306.1
See application file for complete search history.

(56) References Cited

U.S. PATENT DOCUMENTS

| | | | |
|---|---|---|---|
| 8,101,643 B2 * | 1/2012 | Qiu et al. | 514/394 |
| 8,354,419 B2 | 1/2013 | Henderson et al. | |
| 8,507,522 B2 * | 8/2013 | Or et al. | 514/303 |
| 2011/0218231 A1 * | 9/2011 | Fewell et al. | 514/44 A |
| 2013/0072523 A1 * | 3/2013 | Liu et al. | 514/314 |
| 2013/0115193 A1 * | 5/2013 | Lavoie et al. | 424/85.2 |

FOREIGN PATENT DOCUMENTS

| | | |
|---|---|---|
| WO | 2004014313 | 2/2004 |
| WO | 2004014852 | 2/2004 |
| WO | 2006133326 | 12/2006 |
| WO | 2008021927 | 2/2008 |
| WO | 2008021928 | 2/2008 |
| WO | 2008021936 | 2/2008 |
| WO | 2008144380 | 11/2008 |
| WO | 2009020825 | 2/2009 |
| WO | 2009020828 | 2/2009 |
| WO | 2009102318 | 8/2009 |
| WO | 2009102325 | 8/2009 |
| WO | 2009102568 | 8/2009 |
| WO | 2009102633 | 8/2009 |
| WO | 2010017401 | 2/2010 |
| WO | 2010038790 | 4/2010 |
| WO | 2010038791 | 4/2010 |
| WO | 2010138488 | 4/2010 |
| WO | 2010065668 | 6/2010 |
| WO | 2010065674 | 6/2010 |
| WO | 2010065681 | 6/2010 |
| WO | 2010091413 | 8/2010 |
| WO | 2010094977 | 8/2010 |
| WO | 2010096302 | 8/2010 |
| WO | 2010096462 | 8/2010 |
| WO | 2010096777 | 8/2010 |
| WO | 2010038368 | 9/2010 |
| WO | 2010099527 | 9/2010 |

(Continued)

OTHER PUBLICATIONS

International Search Report, PCT/US2011/029825, dated May 24, 2011.

*Primary Examiner* — D M Seaman
(74) *Attorney, Agent, or Firm* — Min Lin

(57) ABSTRACT

Compounds represented by formula I

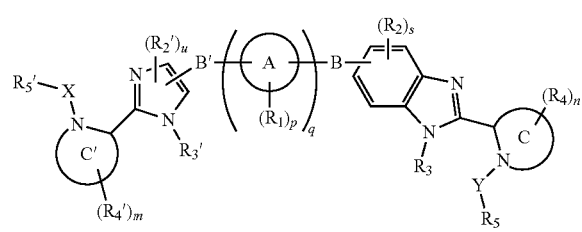

(I)

or pharmaceutically acceptable salts thereof, wherein A, B, B', X, Y, $R_1$, $R_2$, $R_2'$, $R_3$, $R_3'$, $R_4$, $R_4'$, $R_5$, $R_5'$, m, n, or p are as defined herein, are useful for treating flaviviridae viral infections.

27 Claims, No Drawings

(56) References Cited

FOREIGN PATENT DOCUMENTS

| | | |
|---|---|---|
| WO | 2010111483 | 9/2010 |
| WO | 2010111534 | 9/2010 |
| WO | 2010111673 | 9/2010 |
| WO | 2010117635 | 10/2010 |
| WO | 2010117704 | 10/2010 |
| WO | 2010117977 | 10/2010 |
| WO | 2010120621 | 10/2010 |
| WO | 2010120935 | 10/2010 |
| WO | 2010122162 | 10/2010 |
| WO | 2010132538 | 11/2010 |
| WO | 2010132601 | 11/2010 |
| WO | 2010138791 | 12/2010 |
| WO | 2010144646 | 12/2010 |
| WO | 2011004276 | 1/2011 |
| WO | 2011028596 | 3/2011 |
| WO | 2011050146 | 4/2011 |
| WO | 2011059850 | 5/2011 |
| WO | 2011059887 | 5/2011 |
| WO | 2011060000 | 5/2011 |
| WO | 2011075439 | 6/2011 |
| WO | 2011075615 | 6/2011 |
| WO | 2011081918 | 7/2011 |
| WO | 2011082077 | 7/2011 |
| WO | 2011091417 | 7/2011 |
| WO | 2011091446 | 7/2011 |
| WO | 2011109037 | 9/2011 |
| WO | 2011112429 | 9/2011 |
| WO | 2011127350 | 10/2011 |
| WO | 2011149856 | 12/2011 |
| WO | 2011150243 | 12/2011 |
| WO | 2011153396 | 12/2011 |
| WO | 2011156543 | 12/2011 |
| WO | 2012018325 | 2/2012 |
| WO | 2012021591 | 2/2012 |
| WO | 2012021704 | 2/2012 |
| WO | 2012039717 | 3/2012 |
| WO | 2012040389 | 3/2012 |
| WO | 2012040923 | 4/2012 |
| WO | 2012040924 | 4/2012 |
| WO | 2012041014 | 4/2012 |
| WO | 2012041227 | 4/2012 |
| WO | 2012050918 | 4/2012 |
| WO | 2012058125 | 5/2012 |
| WO | 2012122716 | 9/2012 |
| WO | 2012125926 | 9/2012 |
| WO | 2012135581 | 10/2012 |
| WO | 2012166716 | 12/2012 |

* cited by examiner

ANALOGUES FOR THE TREATMENT OR PREVENTION OF FLAVIVIRUS INFECTIONS

CROSS REFERENCE TO RELATED APPLICATIONS

The present application claims the benefit of PCT application number PCT/US2011/029825, filed Mar. 24, 2011, which claims priority to U.S. Provisional Application No. 61/316,988, filed Mar. 24, 2010, which are hereby incorporated by reference in their entirety.

The present invention relates to novel compounds and a method for the treatment or prevention of Flavivirus infections using novel compounds.

Hepatitis is a disease occurring throughout the world. It is generally of viral nature, although there are other causes known. Viral hepatitis is by far the most common form of hepatitis. Nearly 750,000 Americans are affected by hepatitis each year, and out of those, more than 150,000 are infected with the hepatitis C virus ("HCV").

HCV is a positive-stranded RNA virus belonging to the Flaviviridae family and has close relationship to the pestiviruses that include hog cholera virus and bovine viral diarrhea virus (BVDV). HCV is believed to replicate through the production of a complementary negative-strand RNA template. Due to the lack of efficient culture replication system for the virus, HCV particles were isolated from pooled human plasma and shown, by electron microscopy, to have a diameter of about 50-60 nm. The HCV genome is a single-stranded, positive-sense RNA of about 9,600 bp coding for a polyprotein of 3009-3030 amino-acids, which is cleaved co- and post-translationally into mature viral proteins (core, E1, E2, p7, NS2, NS3, NS4A, NS4B, NS5A, NS5B). It is believed that the structural glycoproteins, E1 and E2, are embedded into a viral lipid envelope and form stable heterodimers. It is also believed that the structural core protein interacts with the viral RNA genome to form the nucleocapsid. The nonstructural proteins designated NS2 to NS5 include proteins with enzymatic functions involved in virus replication and protein processing including a polymerase, protease and helicase.

The main source of contamination with HCV is blood. The magnitude of the HCV infection as a health problem is illustrated by the prevalence among high-risk groups. For example, 60% to 90% of hemophiliacs and more than 80% of intravenous drug abusers in western countries are chronically infected with HCV. For intravenous drug abusers, the prevalence varies from about 28% to 70% depending on the population studied. The proportion of new HCV infections associated with post-transfusion has been markedly reduced lately due to advances in diagnostic tools used to screen blood donors.

Combination of pegylated interferon plus ribavirin is the treatment of choice for chronic HCV infection. This treatment does not provide sustained viral response (SVR) in a majority of patients infected with the most prevalent genotype (1a and 1b). Furthermore, significant side effects prevent compliance to the current regimen and may require dose reduction or discontinuation in some patients.

There is therefore a great need for the development of anti-viral agents for use in treating or preventing Flavivirus infections.

In one aspect, the present invention provides a compound of formula (I):

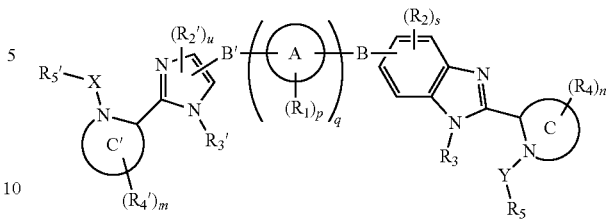

or a pharmaceutically acceptable salt thereof, wherein
each A is independently $C_{6-14}$ aryl, 4-12 membered heterocycle, $C_{3-10}$ cycloalkyl, or 5-12 membered heteroaryl;
B and B' are each independently absent, $C_{1-6}$ alkyl, $C_{2-6}$ alkenyl, or $C_{2-6}$ alkynyl;
C and C' are each independently a 4-7 membered heterocycle;
$R_1$ is halogen, $-OR_a$, $-NR_aR_b$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, $-P(=O)OR_aOR_b$, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, or any two occurrences of $R_1$ can be taken together with the atoms to which they are attached to form a 5-7 cycloalkyl which is unsubstituted or substituted one or more times by $R^{11}$ or a 5-7 membered heterocycle which is unsubstituted or substituted one or more times by $R^{12}$
$R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;
$R_{2'}$ is halogen, $C_{1-10}$ alkyl, $C_{1-6}$ halogenated alkyl, $-(CH_2)_{1-6}OH$, $-NR_bC(=O)R_a$, $C_{6-12}$ aryl, or 5-12 membered heteroaryl;
Each $R_2$ is independently halogen, $C_{1-10}$ alkyl, $C_{1-6}$ halogenated alkyl, $-(CH_2)_{1-6}OH$, $-OR_a$, $-C(=O)OR_a$, $-NR_aR_b$, $-NR_bC(=O)R_a$, $-C(O)NR_aR_b$, $-S(O)_{0-3}R_a$, $C_{6-12}$ aryl, 5-12 membered heterocycle, or 5-12 membered heteroaryl;
$R_3$ and $R_{3'}$ are each independently H, $C_{1-6}$ alkyl, $-(CH_2)_{1-6}OH$, $C_{2-6}$ alkenyl, or $C_{2-6}$ alkynyl;
$R_4$ and $R_{4'}$ are each independently halogen, $-NR_aR_b$, $-C(O)NR_aR_b$, $-(CH_2)_{1-6}OH$) $C_{1-6}$ alkyl, $C_{1-6}$ halogenated alkyl, hydroxyl, $C_{6-14}$ aryl, or $C_{1-6}$ alkoxy; wherein two occurrence of $R_4$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein two occurrence of $R_{4'}$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$;

X and Y are each independently

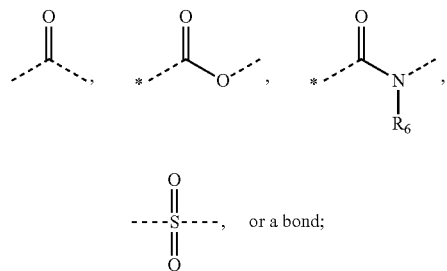

wherein the asterisk (*) indicates the point of attachment to the nitrogen of ring C or C';

$R_5$ and $R_5'$ are each independently H, $C_{1-18}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R_{12}$;

$R_6$ is H, $C_{1-6}$ alkyl, or halogenated $C_{1-6}$ alkyl;

m, and n, are each independently 0, 1, 2, 3 or 4;

p is 0, 1, 2, 3 or 4;

d is 0, 1 or 2;

u is 0 or 1;

s is 0, 1, 2, 3 or 4;

$R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NOR$_c$)$R_a$, —C(=NR$_c$)NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$;

$R^{11}$ is halogen, —$OR_a$, —$NR_aR_b$, —C(=O)$OR_a$, —C(O)NR$_a$R$_b$, —C(=O)OH, —C(=O)R$_a$, —C(=NOR$_c$)R$_a$, —C(=NR$_c$)NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and $R^{12}$ is halogen, —$OR_a$, oxo, —$NR_aR_b$, =NO—$R_c$, —C(=O)$OR_a$, —C(O)NR$_a$R$_b$, —C(=O)OH, —C(=O)R$_a$, —C(=NOR$_c$)R$_a$, —C(=NR$_c$)NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In another aspect, there is provided a method for treating or preventing a Flaviviridae viral infection in a patient comprising administering to the patient a therapeutically effective amount of a compound, composition or combination of the invention.

In another aspect, there is provided a pharmaceutical composition comprising at least one compound of the invention and at least one pharmaceutically acceptable carrier or excipient.

In another aspect, there is provided a combination comprising a compound of the invention and one or more additional agents chosen from viral serine protease inhibitors, viral polymerase inhibitors, viral helicase inhibitors, immunomudulating agents, antioxidant agents, antibacterial agents, therapeutic vaccines, hepatoprotectant agents, antisense agent, inhibitors of HCV NS2/3 protease and inhibitors of internal ribosome entry site (IRES).

In a further aspect, there is provided the use of a compound, composition or combination of the invention for treating or preventing a Flaviviridae viral infection in a human.

In still another aspect, there is provided the use of a compound, composition or combination of the invention for the manufacture of a medicament for treating or preventing a viral Flaviviridae infection in a human.

In one embodiment, compounds of the present invention comprise those wherein the following embodiments are present, either independently or in combination.

In accordance with a further embodiment, the compounds of the present invention are represented by formula (II):

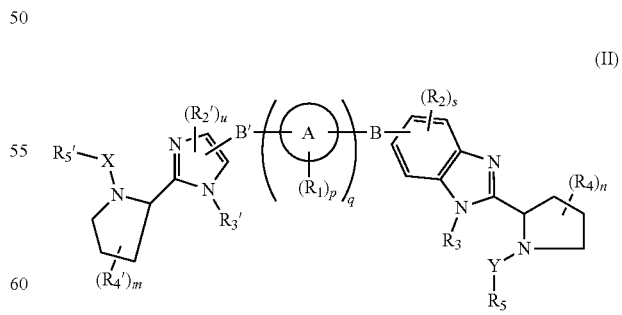

wherein each of the variables are as defined herein.

In accordance with a further embodiment, the compounds of the present invention are represented by formula (IIIA), (IIIB), (IV) or (V):

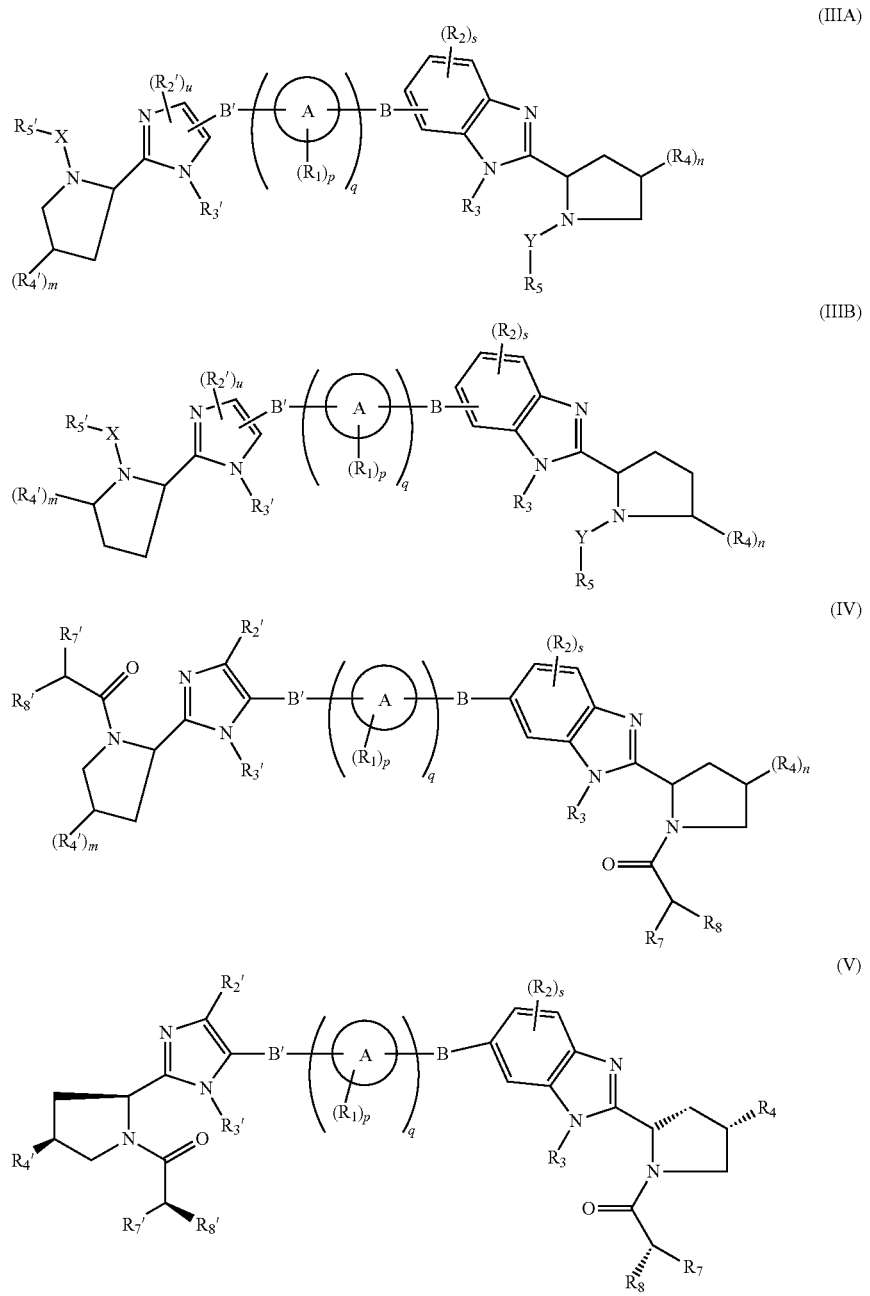

wherein each of the variables are as defined herein.

According to a further embodiment, A is phenyl, thiophene, thieno[3,2-b]thiophene, pyridine, pyrimidine, naphthyl, benzo[1,3]dioxole, benzooxazole, or triazole According to a further embodiment, A is phenyl, thiophene, thieno[3,2-b]thiophene, naphtyl, benzo[1,3]dioxole, or benzooxazole.

According to a further embodiment, A is phenyl, thiophene, pyridine, pyrimidine, or triazole.

According to a further embodiment, A is phenyl or thieno[3,2-b]thiophene.

According to a further embodiment, A is phenyl or thiophene.

According to a further embodiment, A is

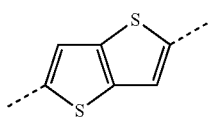

According to a further embodiment, A is

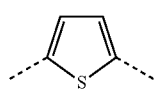

According to a further embodiment, A is

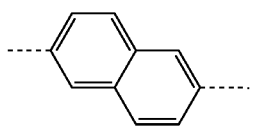

According to a further embodiment, A is

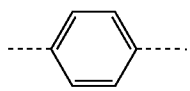

According to a further embodiment, A is a bond.

According to a further embodiment, B and B' are each independently $C_{2-6}$ alkynyl or $C_{1-6}$ alkyl.

According to a further embodiment, B and B' are each independently —(C≡C)— or —(CH$_2$)$_2$—.

According to a further embodiment, B and B' are each —(CH$_2$)$_2$—.

According to a further embodiment, B and B' are each —(C≡C)—.

According to a further embodiment,

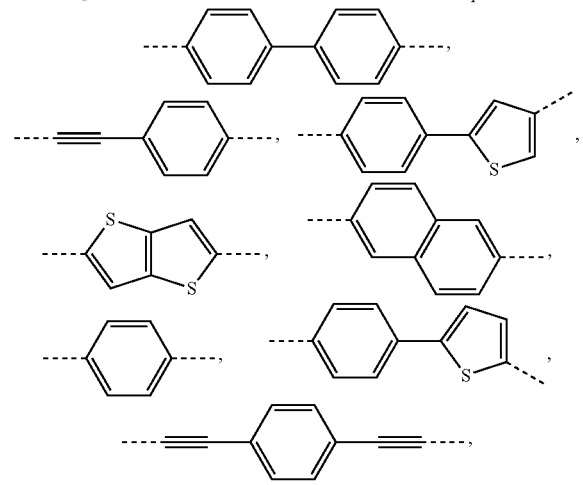

is:

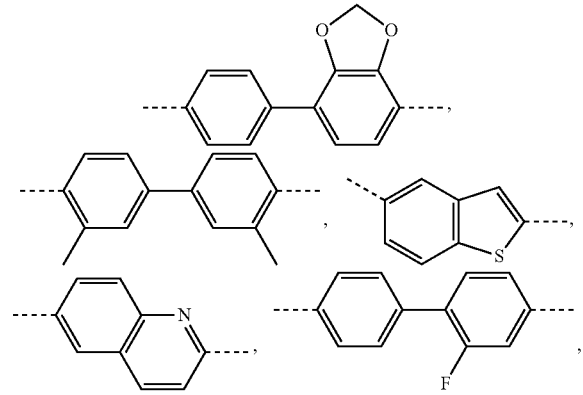

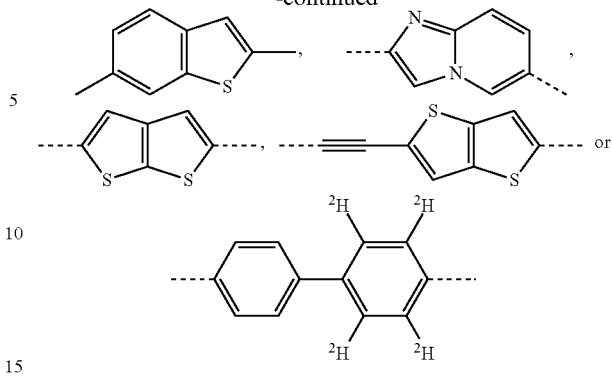

According to a further embodiment, m or n is 2.
According to a further embodiment, m or n is 1.
According to a further embodiment, m and n are 1.
According to a further embodiment, one of m or n is 1, and the other of m or n is 0.
According to a further embodiment, m, and n are each independently 0, or 1, provided that at least one of m and n is 1.
According to a further embodiment, p is 2.
According to a further embodiment, p is 1.
According to a further embodiment, X and Y are each

According to a further embodiment, X and Y are each

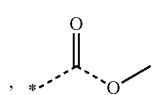

wherein the bond marked with an asterisk (*) indicates the attachment to the nitrogen of ring C or C'.

According to a further embodiment, $R_4$ and $R_4'$ are each independently H, halogen, $C_{1-6}$ alkyl, hydroxyl, phenyl, or $C_{1-4}$ alkoxy.

According to a further embodiment, $R_4$ and $R_4'$ are each independently H, halogen, methyl, ethyl, t-butoxy-, or hydroxyl.

According to a further embodiment, $R_4$ and $R_4'$ are each H.
According to a further embodiment, $R_4$ and $R_4'$ are each fluoro.
According to a further embodiment, $R_4$ and $R_4'$ are each methyl.
According to a further embodiment, at least one of $R_4$ and $R_4'$ is methyl.
According to a further embodiment, $R_3$ and $R_3'$ are each H.
According to a further embodiment, $R_1$ is H, halogen, —$OR_a$, —$NR_aR_b$, —C(=O)$OR_a$, —C(O)$NR_aR_b$, —C(=O)OH, —$NR_bC(=O)R_a$, -hydroxyl, nitro, cyano, —S(O)$_{0-3}R_a$, $C_{1-6}$ alkyl, $C_{2-6}$ alkenyl, $C_{2-6}$ alkynyl, or $C_{1-6}$ halogenated alkyl.

According to a further embodiment, $R_1$ is halogen, $C_{1-3}$ alkyl, hydroxyl, cyano, or $C_{1-3}$ alkoxy.

According to a further embodiment, $R_1$ is chloro, fluoro, methyl, hydroxyl, cyano, or methoxy.

According to a further embodiment, $R_1$ is methyl

According to a further embodiment, $R_1$ is H.

According to a further embodiment, $R_2$ and $R_2'$ are each independently H, halogen, $C_{1-6}$ alkyl, —$(CH_2)_{1-3}$OH, —$OR_a$, —$C(=O)OR_a$, —$C(O)NR_aR_b$, —$C(=O)OH$, $C_{6-12}$ aryl, or 5-12 membered heteroaryl, wherein $R_a$-$R_d$ are each independently H, $C_{1-12}$ alkyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R_2$ and $R_2'$ are each independently H, halogen, $C_{1-6}$ alkyl, —$(CH_2)_{1-3}$OH, —$OR_a$, —$C(=O)OR_a$, —$C(O)NR_aR_b$, —$C(=O)OH$, phenyl, or 5-6 membered heteroaryl, wherein $R_a$-$R_d$ are each independently H, $C_{1-12}$ alkyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R_2$ and $R_2'$ are each methyl.

According to a further embodiment, $R_2$ and $R_2'$ are each iodo.

According to a further embodiment, $R_2$ and $R_2'$ are each H.

According to a further embodiment, $R_6$ is H or $C_{1-3}$ alkyl.

According to a further embodiment, $R_5$ and $R_5'$ are each independently $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, $C_{7-8}$ aralkyl which is unsubstituted or substituted one or more times by $R^{11}$, 5-6 membered heteroaryl which is unsubstituted or substituted one or more times by $R^{11}$, 6-8 membered heteroaralkyl which is unsubstituted or substituted one or more times by $R^{11}$, 3-6 membered heterocycle which is unsubstituted or substituted one or more times by $R^{12}$, or 4-8 membered heterocycle-alkyl which is unsubstituted or substituted one or more times by $R^{12}$.

According to a further embodiment, $R_5$ and $R_5'$ are each independently $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 5-6 membered heterocycle which is unsubstituted or substituted one or more times by $R^{12}$, or 6-7 membered heterocycle-alkyl which is unsubstituted or substituted one or more times by $R^{12}$.

According to a further embodiment, $R_5$ and $R_5'$ are each independently $C_{1-6}$ alkyl which is unsubstituted or substituted one or more times by $R^{10}$, $C_{2-6}$ alkenyl which is unsubstituted or substituted one or more times by $R^{10}$, or $C_{2-6}$ alkynyl which is unsubstituted or substituted one or more times by $R^{10}$.

According to a further embodiment, $R_5$ and $R_5'$ are each independently $C_{1-12}$ alkyl which is unsubstituted or substituted one or more times by $R^{10}$.

According to a further embodiment, $R_5$ and $R_5'$ are each independently methyl, ethyl, propyl, isopropyl, butyl, sec-butyl, tert-butyl, pentyl, 2-methylbutane, 3-methylbutane, cyclopropyl, cyclobutyl, cyclopentyl, cyclohexyl, or cyclohexyl($CH_2$)—, which in each case is unsubstituted or substituted one or more times by $R^{10}$.

According to a further embodiment, $R_5$ and $R_5'$ are each independently methyl, ethyl, propyl, isopropyl, butyl, sec-butyl, tert-butyl, pentyl, 2-methylbutane, 3-methylbutane, cyclopropyl, cyclobutyl, cyclopentyl, cyclohexyl, or cyclohexyl($CH_2$)—.

According to a further embodiment, $R_5$ and $R_5'$ are each independently isopropyl which is unsubstituted or substituted one or more times by $R^{10}$.

According to a further embodiment, $R_5$ and $R_5'$ are each independently isopropyl which is unsubstituted or substituted one or more times by —$OCH_3$.

According to a further embodiment, $R_5$ and $R_5'$ are each isopropyl.

According to a further embodiment, $R_5$ and $R_5'$ are each H or tert-butyl.

According to a further embodiment, $R_5$ and $R_5'$ are each independently phenyl which is unsubstituted or substituted one or more times by $R^{11}$.

According to a further embodiment, $R_5$ and $R_5'$ are each independently benzyl which is unsubstituted or substituted one or more times by $R^{11}$.

According to a further embodiment, $R^{10}$ is halogen, —$OR_a$, oxo, —$NR_aR_b$, =NO—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_aC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{10}$ is —$NR_aR_b$, —$NR_dC(=O)NR_aR_b$, —$NR_bC(=O)R_a$, —$NR_dC(=NR_c)NR_aR_b$, —$NR_bC(=O)OR_a$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{10}$ is —$NR_aR_b$, —$NR_dC(=O)NR_aR_b$, —$NR_bC(=O)R_a$, —$NR_bC(=O)OR_a$, or —$NR_bSO_2R_a$, wherein $R_a$, $R_b$, and $R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{10}$ is —$NR_aR_b$ or —$NR_dC(=O)NR_aR_b$, wherein $R_a$ and $R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{10}$ is —$NR_dC(=O)NR_aR_b$, wherein $R_a$, $R_b$, are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{10}$ is halogen, —$OR_a$, oxo, —$C(=O)OR_a$, —$C(O)NR_aR_b$, —$C(=O)OH$, —$C(=O)R_a$, —$OC(=O)NR_aR_b$, —$OC(=O)R_a$, —$OC(=O)OR_a$, hydroxyl, cyano, wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{10}$ is halogen, —$OR_a$, oxo, —C(=O)$OR_a$, —C(O)$NR_aR_b$, —C(=O)OH, —OC(=O)$NR_aR_b$, hydroxyl, or cyano, wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{10}$ is halogen, $C_{1-6}$ alkoxy, hydroxyl, or $NH_2$.

According to a further embodiment, $R^{10}$ is halogen, hydroxyl, or $NH_2$.

According to a further embodiment, $R^{10}$ is halogen.

According to a further embodiment, $R^{11}$ is halogen, —$OR_a$, —$NR_aR_b$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, or —$NR_bSO_2NR_aR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{11}$ is halogen, —$OR_a$, —$NR_aR_b$, —C(=O)$OR_a$, —C(O)$NR_aR_b$, —C(=O)OH, —C(=O)$R_a$, —$NR_dC$(=O)$NR_aR_b$, —$NR_bC$(=O)$R_a$, —$NR_bC$(=O)$OR_a$, —OC(=O)$NR_aR_b$, —OC(=O)$R_a$, —OC(=O)$OR_a$, hydroxyl, cyano, —$SO_2NR_aR_b$, —$NR_bSO_2R_a$, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{11}$ is halogen, —$OR_a$, —$NR_aR_b$, —C(O)$NR_aR_b$, —C(=O)OH, —C(=O)$R_a$, —$NR_dC$(=O)$NR_aR_b$, —$NR_bC$(=O)$R_a$, —$NR_bC$(=O)$OR_a$, —OC(=O)$NR_aR_b$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{11}$ is halogen, —$OR_a$, —$NR_aR_b$, hydroxyl, cyano, or $C_{1-6}$ alkyl, wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{11}$ is halogen, hydroxyl, cyano, or $NH_2$.

According to a further embodiment, $R^{11}$ is halogen.

According to a further embodiment, $R^{12}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{12}$ is halogen, —$OR_a$, oxo, —$NR_aR_b$, —C(=O)$OR_a$, —C(O)$NR_aR_b$, —C(=O)OH, —C(=O)$R_a$, —$NR_dC$(=O)$NR_aR_b$, —$NR_bC$(=O)$R_a$, —$NR_bC$(=O)$OR_a$, —OC(=O)$NR_aR_b$, —OC(=O)$R_a$, —OC(=O)$OR_a$, hydroxyl, cyano, —$SO_2NR_aR_b$, —$NR_bSO_2R_a$, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{12}$ is halogen, —$OR_a$, oxo, —$NR_aR_b$, —C(O)$NR_aR_b$, —C(=O)OH, —C(=O)$R_a$, —$NR_dC$(=O)$NR_aR_b$, —$NR_bC$(=O)$R_a$, —$NR_bC$(=O)$OR_a$, —OC(=O)$NR_aR_b$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{12}$ is halogen, —$OR_a$, oxo, —$NR_aR_b$, hydroxyl, cyano, or $C_{1-6}$ alkyl, wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

According to a further embodiment, $R^{12}$ is halogen.

According to a further embodiment, $R_a$-$R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

According to a further embodiment, $R_a$ and $R_c$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, and $R_b$, and $R_d$ are each independently H or $C_{1-3}$ alkyl.

According to a further embodiment, $R_a$ and $R_c$ are each independently H, $C_{1-6}$ alkyl, $C_{2-6}$ alkenyl, $C_{2-6}$ alkynyl, phenyl, benzyl, 5-6 membered heteroaryl, 6-8 membered heteroaralkyl, 5-6 membered heterocycle, or 6-8 membered heterocycle-alkyl, and $R_b$, and $R_d$ are each independently H or $C_{1-3}$ alkyl.

According to a further embodiment, $R_a$-$R_d$ are each independently H or $C_{1-3}$ alkyl.

In accordance with a further embodiment, the compounds of the present invention are represented by formula (IV):

According to a further embodiment, $R_8$ and $R_8'$ are each independently —$NR_aR_b$, —$NR_bC$(=O)$R_a$, or —$NR_bC$(=O)$OR_a$, wherein $R_a$-$R_b$ are each independently H, $C_{1-6}$ alkyl, phenyl, benzyl, 5-6 membered heteroaryl, 6-8 membered heteroaralkyl, 5-6 membered heterocycle, or 6-8 membered heterocycle-alkyl.

According to a further embodiment, $R_8$ and $R_8'$ are each independently —$NR_aR_b$ or —$NR_bC(=O)OR_a$, wherein $R_a$-$R_b$ are each independently H, $C_{1-6}$ alkyl, phenyl, benzyl, 5-6 membered heteroaryl, 6-8 membered heteroaralkyl, 5-6 membered heterocycle, or 6-8 membered heterocycle-alkyl.

According to a further embodiment, $R_8$ and $R_8'$ are each independently —$NR_bC(=O)OR_a$, wherein $R_a$-$R_b$ are each independently H, $C_{1-6}$ alkyl, phenyl, benzyl, 5-6 membered heteroaryl, 6-8 membered heteroaralkyl, 5-6 membered heterocycle, or 6-8 membered heterocycle-alkyl.

According to a further embodiment, $R_8$ and $R_8'$ in formula (IV) are each independently —$NR_bC(=O)OR_a$, wherein $R_a$-$R_b$ are each independently H, $C_{1-6}$ alkyl, phenyl, tetrahydrofuran, or benzyl.

According to a further embodiment, $R_8$ and $R_8'$ in formula (IV) are each independently —$NR_bC(=O)OR_a$, wherein $R_a$ is $C_{1-6}$ alkyl and $R_b$ is H or methyl.

According to a further embodiment, $R_8$ and $R_8'$ in formula (IV) are each independently —$NR_bC(=O)OR_a$, wherein $R_a$ is $C_{1-6}$ alkyl and $R_b$ is H.

According to a further embodiment, $R_8$ and $R_8'$ in formula (IV) are each independently —$NR_bC(=O)OR_a$, wherein $R_a$ is methyl and $R_b$ is H.

According to a further embodiment, $R_7$ and $R_7'$ are each independently $C_{1-8}$ alkyl, $C_{2-8}$ alkenyl, $C_{2-8}$ alkynyl, phenyl, benzyl, 5-6 membered heteroaryl, 6-7 membered heteroaralkyl, 3-6 membered heterocycle, or 4-7 membered heterocycle-alkyl;

According to a further embodiment, $R_7$ and $R_7'$ are each independently phenyl.

According to a further embodiment, $R_7$ and $R_7'$ are each independently $C_{1-6}$ alkyl.

According to a further embodiment, $R_7$ and $R_7'$ are each independently methyl, ethyl, propyl, isopropyl, butyl, sec-butyl, tert-butyl, pentyl, 2-methylbutane, 3-methylbutane, cyclopropyl, cyclobutyl, cyclopentyl, or cyclohexyl.

According to a further embodiment, $R_7$ and $R_7'$ are each isopropyl.

In accordance with a further embodiment, the compounds of the present invention are represented by formula (V):

According to a further embodiment, as valency allows in B, B', $R_a$-$R_d$, $R_1$, $R_2$, $R_2'$, $R_3$, $R_3'$, $R_4$, $R_4'$, $R^{10}$, $R^{11}$ and $R^{12}$ each of alkyl, alkenyl, alkynyl, alkoxy, aryl, aralkyl, heteroaryl, heteroaralkyl, heterocycle, or heterocycle-alkyl is independently unsubstituted or substituted one or more times by halogen, —$OR_a$, —$NR_aR_b$, $C(=O)OR_a$, —$C(O)NR_aR_b$, —$C(=O)OH$, hydroxyl, nitro, azido, or cyano, wherein $R_a$-$R_d$, are each independently H, $C_{1-12}$ alkyl.

According to a further embodiment, as valency allows in B, B', $R_a$-$R_d$, $R_1$, $R_2$, $R_2'$, $R_3$, $R_3'$, $R_4$, $R_4'$, $R^{10}$, $R^{11}$ and $R^{12}$ each of alkyl, alkenyl, alkynyl, alkoxy, aryl, aralkyl, heteroaryl, heteroaralkyl, heterocycle, or heterocycle-alkyl is independently unsubstituted or substituted one time by halogen.

According to a further embodiment, as valency allows in B, B', $R_a$-$R_d$, $R_1$, $R_2$, $R_2'$, $R_3$, $R_3'$, $R_4$, $R_4'$, $R^{10}$, $R^{11}$ and $R^{12}$ each of alkyl, alkenyl, alkynyl, alkoxy, aryl, aralkyl, heteroaryl, heteroaralkyl, heterocycle, or heterocycle-alkyl is independently unsubstituted or substituted one time by fluoro.

In accordance with the present invention, the compounds are selected from compounds as defined in the formulas wherein:
A is $C_{6-14}$ aryl, 5-12 membered heteroaryl, or a bond;
B and B' are each independently —(C≡C)— or —(CH$_2$)$_2$—;
$R_1$ is H, halogen, —$OR_a$, —$NR_aR_b$, —$C(=O)OR_a$, —$C(O)NR_aR_b$, —$C(=O)OH$, —$NR_bC(=O)R_a$, hydroxyl, nitro, cyano, —$S(O)_{0-3}R_a$, —$C_{1-6}$ alkyl, $C_{2-6}$ alkenyl, $C_{2-6}$ alkynyl, or $C_{1-6}$ halogenated alkyl;

$R_2$ and $R_2'$ are each independently H, methyl, or iodo;
m and n are each independently 0, 1 or 2;
p is 0, 1 or 2;
$R_3$ and $R_3'$ are H;
$R_4$ and $R_4'$ are each independently H, halogen, $C_{1-6}$ alkyl, hydroxyl, phenyl, or $C_{1-4}$ alkoxy;
X and Y are

$R_5$ and $R_5'$ are each independently $C_{1-12}$ alkyl which is unsubstituted or substituted one or more times by $R^{10}$.

In accordance with the present invention, the compounds are selected from compounds as defined in the formulas wherein:
A is $C_{6-14}$ aryl, 5-12 membered heteroaryl, or a bond;
B and B' are each independently —(C≡C)— or —(CH$_2$)$_2$—;
$R_1$ is H or methyl;
$R_2$ and $R_2'$ are each independently H, methyl or iodo;
m and n are each independently 0, 1 or 2;
p is 0, 1 or 2;
$R_3$ and $R_3'$ are H;
$R_4$ and $R_4'$ are each independently H, halogen, $C_{1-6}$ alkyl, hydroxyl, phenyl, or $C_{1-4}$ alkoxy;
X and Y are

$R_5$ and $R_5'$ are each independently $C_{1-12}$ alkyl which is unsubstituted or substituted one or more times by $R^{10}$.

In accordance with the present invention, the compounds are selected from compounds as defined in the formulas wherein:
A is phenyl, thiophene, thieno[3,2-b]thiophene, pyridine, pyrimidine, naphthyl, benzo[1,3]dioxole, benzooxazole, or triazole;
B and B' are each independently —(C≡C)— or —(CH$_2$)$_2$—;
$R_1$ is H or methyl;
$R_2$ and $R_2'$ are each independently H, methyl or iodo;
m and n are each independently 0, 1 or 2;
p is 0, 1 or 2;
$R_3$ and $R_3'$ are H;
$R_4$ and $R_4'$ are each independently H, halogen, $C_{1-6}$ alkyl, hydroxyl, phenyl, or $C_{1-4}$ alkoxy;
X and Y are

$R_5$ and $R_5'$ are each independently $C_{1-12}$ alkyl which is unsubstituted or substituted one or more times by $R^{10}$.

In accordance with the present invention, the compounds are selected from compounds as defined in the formulas wherein:
A is phenyl, thiophene, thieno[3,2-b]thiophene, naphthyl, benzo[1,3]dioxole, or benzooxazole;
B and B' are each independently —(C≡C)— or —(CH$_2$)$_2$—;

$R_1$ is H, halogen, $-OR_a$, $-NR_aR_b$, $-C(=O)OR_a$, $-C(O)NR_aR_b$, $-C(=O)OH$, $-NR_bC(=O)R_a$, hydroxyl, nitro, cyano, $-S(O)_{0-3}R_a$, $C_{1-6}$ alkyl, $C_{2-6}$ alkenyl, $C_{2-6}$ alkynyl, or $C_{1-6}$ halogenated alkyl;

$R_2$ and $R_2'$ are each independently H, methyl or iodo;

m and n are each independently 0, 1 or 2;

p is 0, 1 or 2;

$R_3$ and $R_3'$ are H;

$R_4$ and $R_4'$ are each independently H, halogen, $C_{1-6}$ alkyl, hydroxyl, phenyl, or $C_{1-4}$ alkoxy;

X and Y are each

$R_5$ and $R_5'$ are each independently $C_{1-12}$ alkyl which is unsubstituted or substituted one or more times by $R^{10}$;

$R_7$ and $R_7'$ are each independently $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 3-6 membered heterocycle which is unsubstituted or substituted one or more times by $R^{12}$, or 4-7 membered heterocycle-alkyl which is unsubstituted or substituted one or more times by $R^{12}$; and $R_8$ and $R_8'$ are each independently $-NR_aR_b$, $-NR_aC(=O)NR_aR_b$, $-NR_bC(=O)R_a$, $-NR_dC(=NR_c)NR_aR_b$, $-NR_bC(=O)OR_a$, $-NR_bSO_2R_a$, $-NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In some embodiments, the compounds of this invention are represented in Table 1A. In certain embodiments, the variables used herein are as defined in the specific embodiments as shown in Table 1A.

In some embodiments, the compounds of this invention are represented in Table 1B. In certain embodiments, the variables used herein are as defined in the specific embodiments as shown in Table 1B.

In one embodiment in the compounds of the present invention $R_1$ is halogen, $-OR_a$, $-NR_aR_b$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, $-P(=O)OR_aOR_b$, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$.

In one embodiment of the compounds of the present invention, herein as valency allows in B, B', $R_a$-$R_d$, $R_1$, $R_2$, $R_2'$, $R_3$, $R_3'$, $R_4$, $R_4'$, $R^{10}$, $R^{11}$ and $R^{12}$ each of alkyl, alkenyl, alkynyl, alkoxy, aryl, aralkyl, heteroaryl, heteroaralkyl, heterocycle, or heterocycle-alkyl is independently unsubstituted or substituted one or more times by halogen, $-OR_a$, oxo, $-NR_aR_b$, $=NO-R_c$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_bC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$; wherein $R_a$-$R_d$ are each independently H, $C_{1-12}$ alkyl.

In one embodiment in the compounds of the present invention p is 0, 1 or 2.

In one embodiment in the compounds of the present invention p is 0 or 1.

In one embodiment in the compounds of the present invention p is 0.

In one embodiment in the compounds of the present invention p is 2.

In one embodiment in the compounds of the present invention $R_4$ and $R_4'$ are H.

In one embodiment in the compounds of the present invention $R_1$ is halogen, $C_{1-3}$ alkyl, hydroxyl, cyano, or $C_{1-3}$ alkoxy.

In one embodiment in the compounds of the present invention $R_1$ is chloro, fluoro, methyl, hydroxyl, cyano, or methoxy.

In one embodiment in the compounds of the present invention n $R_1$ is H.

In one embodiment in the compounds of the present invention $R^{10}$ is halogen, $-OR_a$, oxo, $-C(=O)OR_a$, $-C(O)NR_aR_b$, $-C(=O)OH$, $-C(=O)R_a$, $-OC(=O)NR_aR_b$, $-OC(=O)R_a$, $-OC(=O)OR_a$, hydroxyl, cyano, wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{11}$ is halogen, $-OR_a$, $-NR_aR_b$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, or $-NR_bSO_2NR_aR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{11}$ is halogen, $-OR_a$, $-NR_aR_b$, $-C(=O)OR_a$, $-C(O)NR_aR_b$, $-C(=O)OH$, $-C(=O)R_a$, $-NR_dC(=O)NR_aR_b$, $-NR_bC(=O)R_a$, $-NR_bC(=O)OR_a$, $-OC(=O)NR_aR_b$, $-OC(=O)R_a$, $-OC(=O)OR_a$, hydroxyl, cyano, $-SO_2NR_aR_b$, $-NR_bSO_2R_a$, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{11}$ is halogen, $-OR_a$, $-NR_aR_b$, $-C(O)NR_aR_b$, $-C(=O)OH$, $-C(=O)R_a$, $-NR_dC(=O)NR_aR_b$, $-NR_bC(=O)R_a$, $-NR_bC(=O)OR_a$, $-OC(=O)NR_aR_b$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{11}$ is halogen, $-OR_a$, $-NR_aR_b$, hydroxyl, cyano, $C_{1-6}$ alkyl, wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{12}$ is halogen, $-OR_a$, oxo, $-NR_aR_b$, $=NO-R_c$, $-C(=O)OR_a$, $-C(O)NR_aR_b$, $-C(=O)OH$, $-C(=O)R_a$, $-C(=NOR)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{12}$ is halogen, $-OR_a$, oxo, $-NR_aR_b$, $-C(=O)OR_a$, $-C(O)NR_aR_b$, $-C(=O)OH$, $-C(=O)R_a$, $-NR_dC(=O)NR_aR_b$, $-NR_bC(=O)R_a$, $-NR_dC(=O)OR_a$, $-OC(=O)NR_aR_b$, $-OC(=O)R_a$, $-OC(=O)OR_a$, hydroxyl, cyano, $-SO_2NR_aR_b$, $-NR_bSO_2R_a$, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{12}$ is halogen, $-OR_a$, oxo, $-NR_aR_b$, $-C(O)NR_aR_b$, $-C(=O)OH$, $-C(=O)R_a$, $-NR_dC(=O)NR_aR_b$, $-NR_bC(=O)R_a$, $-NR_bC(=O)OR_a$, $-OC(=O)NR_aR_b$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{12}$ is halogen, $-OR_a$, oxo, $-NR_aR_b$, hydroxyl, cyano, $C_{1-6}$ alkyl, wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention wherein as valency allows in B, B', $R_a$-$R_d$, $R_1$, $R_2$, $R_2'$, $R_3$, $R_3'$, $R_4$, $R_4'$, $R^{10}$, $R^{11}$ and $R^{12}$ each of alkyl, alkenyl, alkynyl, alkoxy, aryl, aralkyl, heteroaryl, heteroaralkyl, heterocycle, or heterocycle-alkyl is independently unsubstituted or substituted one or more times by halogen, $-OR_{a'}$—$NR_{a'}R_{b'}$, $C(=O)OR_{a'}$, $-C(O)NR_{a'}R_{b'}$, $-C(=O)OH$, hydroxyl, nitro, azido, cyano; wherein $R_{a'}$-$R_{d'}$ are each independently H, $C_{1-12}$ alkyl.

In one embodiment in the compounds of the present invention wherein as valency allows in B, B', $R_a$-$R_d$, $R_1$, $R_2$, $R_2'$, $R_3$, $R_3'$, $R_4$, $R_4'$, $R^{10}$, $R^{11}$ and $R^{12}$ each of alkyl, alkenyl, alkynyl, alkoxy, aryl, aralkyl, heteroaryl, heteroaralkyl, heterocycle, or heterocycle-alkyl is independently unsubstituted or substituted one time by halogen.

In one embodiment in the compounds of the present invention wherein as valency allows in B, B', $R_a$-$R_d$, $R_1$, $R_2$, $R_2'$, $R_3$, $R_3'$, $R_4$, $R_4'$, $R^{10}$, $R^{11}$ and $R^{12}$ each of alkyl, alkenyl, alkynyl, alkoxy, aryl, aralkyl, heteroaryl, heteroaralkyl, heterocycle, or heterocycle-alkyl is independently unsubstituted or substituted one time by fluoro.

In one embodiment, the compounds of the present invention are represented by a compound of formula (VI):

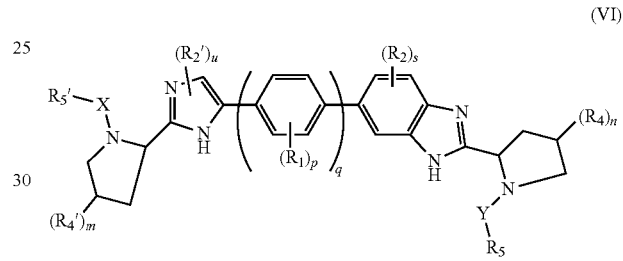

(VI)

or a pharmaceutically acceptable salt thereof, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R_1$ is halogen, $-OR_a$, $-NR_aR_b$, $-C(=O)OR_a$, $-C(O)NR_aR_b$, $-C(=O)OH$, $-C(=O)R_a$, $-C(=NOR_c)R^a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, $-P(=O)OR_aOR_b$, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, or any two occurrences of $R_1$ can be taken together with the atoms to which they are attached to form a 5-7 cycloalkyl which is unsubstituted or substituted one or more times by $R^{11}$ or a 5-7 membered heterocycle which is unsubstituted or substituted one or more times by $R^{12}$;

$R_{2'}$ is halogen, $C_{1-10}$ alkyl, $C_{1-6}$ halogenated alkyl, $-(CH_2)_{1-6}OH$, $-NR_bC(=O)R_a$, $C_{6-12}$ aryl, or 5-12 membered heteroaryl;

each $R_2$ is independently halogen, $C_{1-10}$ alkyl, $C_{1-6}$ halogenated alkyl, $-(CH_2)_{1-6}OH$, $-OR_a$, $-C(=O)OR_a$, $-NR_aR_b$, $-NR_bC(=O)R_a$, $-C(O)NR_aR_b$, $-S(O)_{0-3}R_a$, $C_{6-12}$ aryl, 5-12 membered heterocycle, or 5-12 membered heteroaryl;

$R_4$ and $R_4'$ are each independently $C_{1-6}$ alkyl;

X and Y are each independently

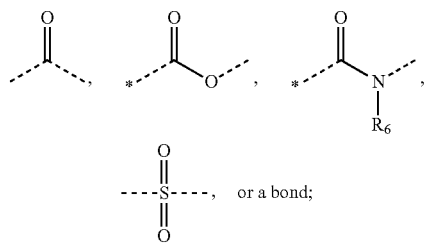

wherein the asterisk (*) indicates the point of attachment to the nitrogen of the pyroolidine ring;

$R_5$ and $R_5'$ are each independently H, $C_{1-18}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_6$ is H, $C_{1-6}$ alkyl, or halogenated $C_{1-6}$ alkyl;

m and n are each independently 0, 1 or 2, provided that at least one of m and n is 1;

p is 0, 1, 2, 3 or 4;

q is 1 or 2;

u is 0 or 1;

s is 0, 1, 2, 3 or 4;

$R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$;

$R^{11}$ is halogen, —$OR_a$, —$NR_aR_b$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O) $R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and $R^{12}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment, the compounds of the present invention are represented by a compound of formula (VI), wherein $R_1$ is halogen, $C_{1-4}$ alkyl which is unsubstituted or substituted one or more times by $R^{10}$, —C(=O)$OR_a$, —C(O)$NR_aR_b$, hydroxyl, cyano, or $C_{1-3}$ alkoxy.

In one embodiment, the compounds of the present invention are represented by a compound of formula (VI), wherein at least one of $R_4$ and $R_4'$ are methyl.

In one embodiment, the compounds of the present invention are represented by a compound of formula (VI), wherein $R_4$ and $R_4'$ are methyl.

In one embodiment, the compounds of the present invention are represented by a compound of formula (VI), wherein one of m and n is 1, and the other is 0.

In one embodiment, the compounds of the present invention are represented by a compound of formula (VI), wherein m and n are 1.

In one embodiment, the compounds of the present invention are represented by a compound of formula (VI), wherein X and Y are

In one embodiment, the compounds of the present invention are represented by a compound of formula (VI), wherein q is 2.

In one embodiment, the compounds of the present invention are represented by a compound of formula (VIA):

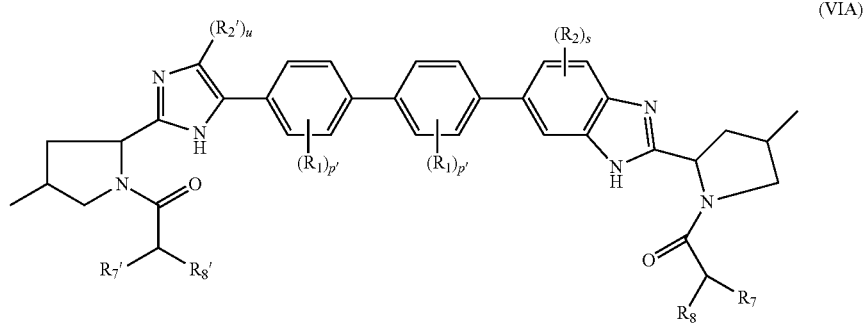

or a pharmaceutically acceptable salt thereof wherein each of the variables are as defined herein, and each p' is independently 0, 1 or 2;

$R_7$ and $R_7'$ are each independently $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 3-6 membered heterocycle which is unsubstituted or substituted one or more times by $R^{12}$, or 4-7 membered heterocycle-alkyl which is unsubstituted or substituted one or more times by $R^{12}$; and $R_8$ and $R_8'$ are each independently —$NR_aR_b$, —$NR_dC(=O)NR_aR_b$, —$NR_bC(=O)R_a$, —$NR_dC(=NR_c)NR_aR_b$, —$NR_bC(=O)OR_a$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment, the compounds of the present invention are represented by a compound of formula (VIB):

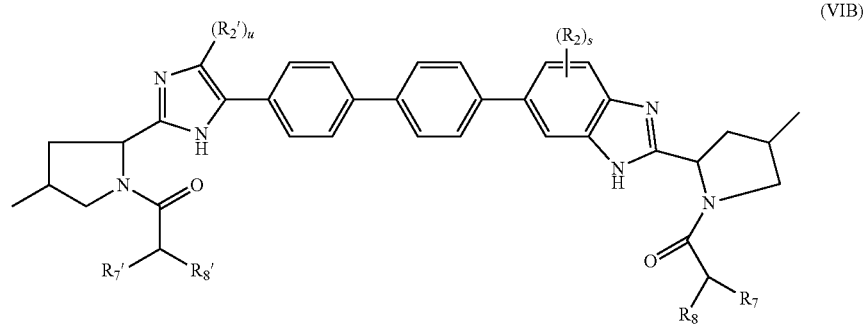

(VIB)

or a pharmaceutically acceptable salt thereof wherein each of the variables are as defined herein, and $R_7$ and $R_7'$ are each independently $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 3-6 membered heterocycle which is unsubstituted or substituted one or more times by $R^{12}$, or 4-7 membered heterocycle-alkyl which is unsubstituted or substituted one or more times by $R^{12}$; and $R_8$ and $R_8'$ are each independently —$NR_aR_b$, —$NR_dC(=O)NR_aR_b$, —$NR_bC(=O)R_a$, —$NR_dC(=NR_c)NR_aR_b$, —$NR_bC(=O)OR_a$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment, the compounds of the present invention are represented by a compound of formula (VIIA):

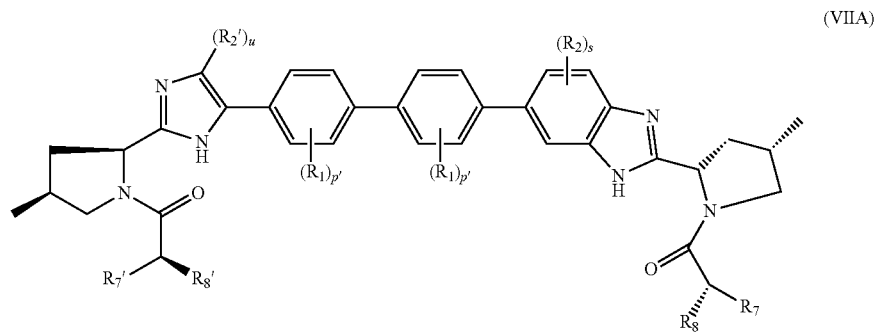

(VIIA)

or a pharmaceutically acceptable salt thereof wherein each of the variables are as defined herein, and each p' is independently 0, 1 or 2;

$R_7$ and $R_7'$ are each independently $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 3-6 membered heterocycle which is unsubstituted or substituted one or more times by $R^{12}$, or 4-7 membered heterocycle-alkyl which is unsubstituted or substituted one or more times by $R^{12}$; and $R_8$ and $R_8'$ are each independently —$NR_aR_b$, —$NR_dC(=O)NR_aR_b$, —$NR_bC(=O)R_a$, —$NR_dC(=NR_c)NR_aR_b$, —$NR_bC(=O)OR_a$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment, the compounds of the present invention are represented by a compound of formula (VIIB):

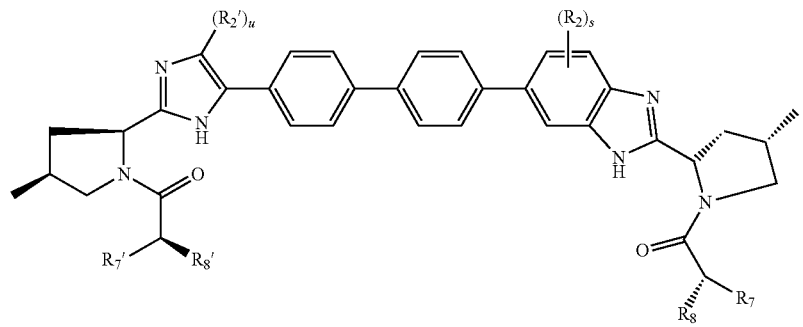

or a pharmaceutically acceptable salt thereof wherein each of the variables are as defined herein, and $R_7$ and $R_7'$ are each independently $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 3-6 membered heterocycle which is unsubstituted or substituted one or more times by $R^{12}$, or 4-7 membered heterocycle-alkyl which is unsubstituted or substituted one or more times by $R^{12}$; and $R_8$ and $R_8'$ are each independently —$NR_aR_b$, —$NR_dC(=O)NR_aR_b$, —$NR_bC(=O)R_a$, —$NR_dC(=NR_c)NR_aR_b$, —$NR_bC(=O)OR_a$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment, the compounds of the present invention are represented by a compound of formula (VIA), (VIB), (VIIA) or (VIIB), wherein $R_8$ and $R_8'$ are each independently —$NR_aR_b$, —$NR_bC(=O)R_a$, —$NR_bC(=O)OR_a$, wherein $R_a$-$R_b$ are each independently H, $C_{1-6}$ alkyl, phenyl, benzyl, 5-6 membered heteroaryl, 6-8 membered heteroaralkyl, 5-6 membered heterocycle, or 6-8 membered heterocycle-alkyl.

In one embodiment, the compounds of the present invention are represented by a compound of formula (VIA), (VIB), (VIIA) or (VIIB), wherein s and u are 0.

In one embodiment, the compounds of the present invention are represented by a compound of formula (VIA), (VIB), (VIIA) or (VIIB), wherein $R_8$ and $R_8'$ in formulas (IV), are each independently —$NR_bC(=O)OR_a$, wherein $R_a$-$R_b$ are each independently H, $C_{1-6}$ alkyl, phenyl, tetrahydrofuran, or benzyl.

In one embodiment, the compounds of the present invention are represented by a compound of formula (VIA), (VIB), (VIIA) or (VIIB), wherein $R_7$ and $R_7'$ are each independently phenyl which is unsubstituted or substituted one or more times by $R^{11}$.

In one embodiment, the compounds of the present invention are represented by a compound of formula (VIA), (VIB), (VIIA) or (VIIB), wherein $R_7$ and $R_7'$ are each independently, $C_{1-6}$ alkyl which is unsubstituted or substituted one or more times by $R^{10}$.

In one embodiment, the compounds of the present invention are represented by a compound of formula (VIA), (VIB), (VIIA) or (VIIB), wherein $R_7$ and $R_7'$ are each independently methyl, ethyl, propyl, isopropyl, methoxyisopropyl, butyl, sec-butyl, tert-butyl, pentyl, 2-methylbutane, 3-methylbutane, cyclopropyl, cyclobutyl, cyclopentyl, or cyclohexyl.

In one embodiment, the compounds of the present invention are represented by a compound of formula (VIA), (VIB), (VIIA) or (VIIB), wherein $R_7$ and $R_8$ or $R_{7'}$ and $R_{8'}$ together with the carbon to which they are attached are each independently:

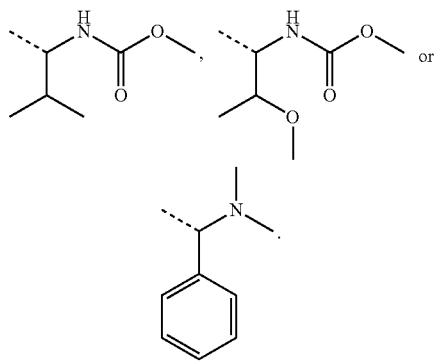

The use of a compound of the present invention for treating an Hepatitis C viral infection in a human. The use of a compound of the present invention further comprising administering at least one additional agent. The use of a compound of the present invention wherein said at least one additional agent is selected from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

The use of a compound of the present invention, wherein said at least one additional agent is selected from ribavirin and interferon-α.

The use of a compound of the present invention for the manufacture of a medicament.

A pharmaceutical formulation comprising at least one compound of the present invention and at least one pharmaceutically acceptable carrier or excipient.

The use of a compound of the present invention for treating an Hepatitis C viral infection in a human. The use of a compound of the present invention further comprising administering at least one additional agent. The use of a compound of the present invention wherein said at least one additional agent is selected from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES). The use of a compound of the present invention wherein said at least one additional agent is selected from ribavirin and interferon-α.

The use of a compound of the present invention for the manufacture of a medicament.

A pharmaceutical formulation comprising at least one compound of the present invention and at least one pharmaceutically acceptable carrier or excipient.

In one embodiment, the present invention provides a method of treating or preventing infection by a HCV virus, comprising contacting a biological sample or administering to a patient in need thereof a compound disclosed herein in an amount effective to treat or prevent the infection.

In one embodiment of the method, HCV is of genotype 1. In another embodiment, HCV is of genotype 1a, genotype 1b, or a combination thereof.

According to an aspect of the invention, the compounds of the invention are selected from Table 1A.

TABLE 1A

| Compound | # |
| --- | --- |
| | 1 |
| | 2 |

TABLE 1A-continued

| Compound | # |
|---|---|
| | 3 |
| | 4 |
| | 13 |
| | 18 |

TABLE 1A-continued

| Compound | # |
|---|---|
| [chemical structure] | 23 | and pharmaceutically acceptable salts thereof.

According to an aspect of the invention, the compounds of the invention are selected from Table 1B.

TABLE 1B

| Compound | # |
|---|---|
| [chemical structure] | 5 |
| [chemical structure] | 6 |
| [chemical structure] | 7 |

TABLE 1B-continued
| Compound | # |
|---|---|
| 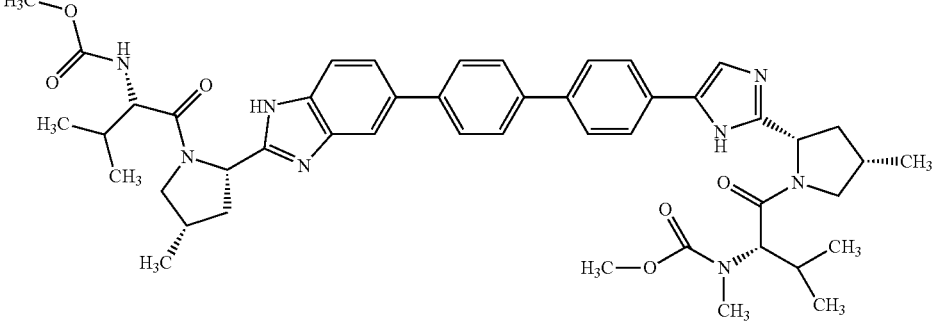 | 8 |
| 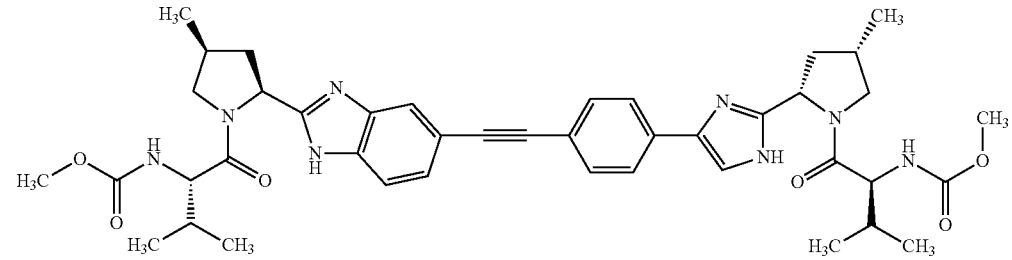 | 9 |
| 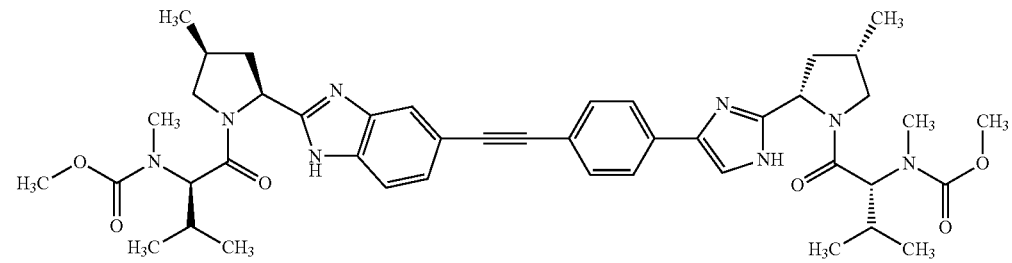 | 10 |
| 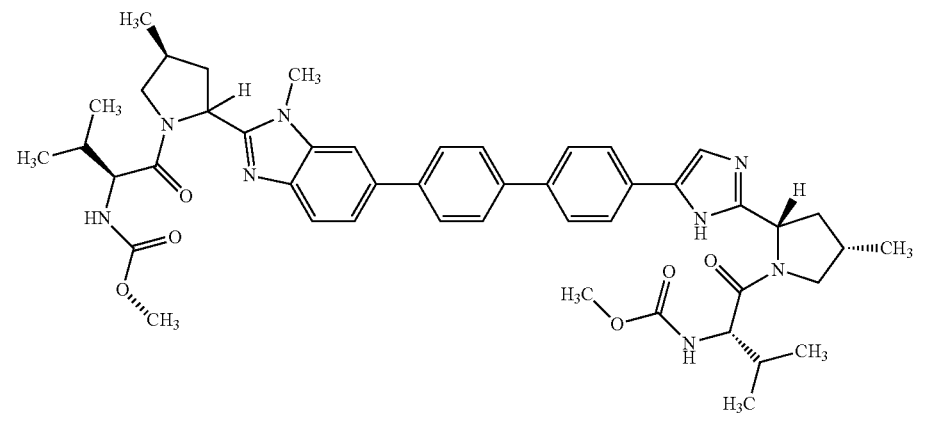 | 11 |
| 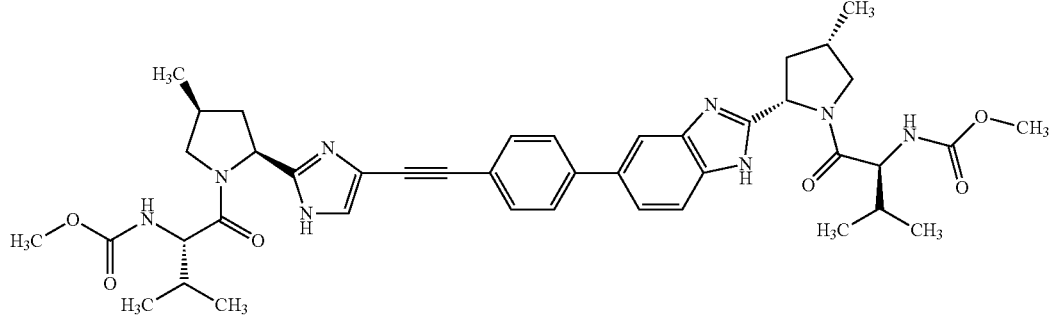 | 12 |

TABLE 1B-continued
| Compound | # |
|---|---|
| 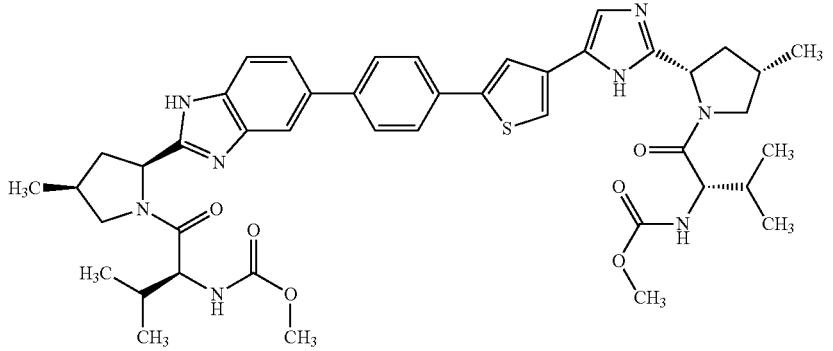 | 14 |
| 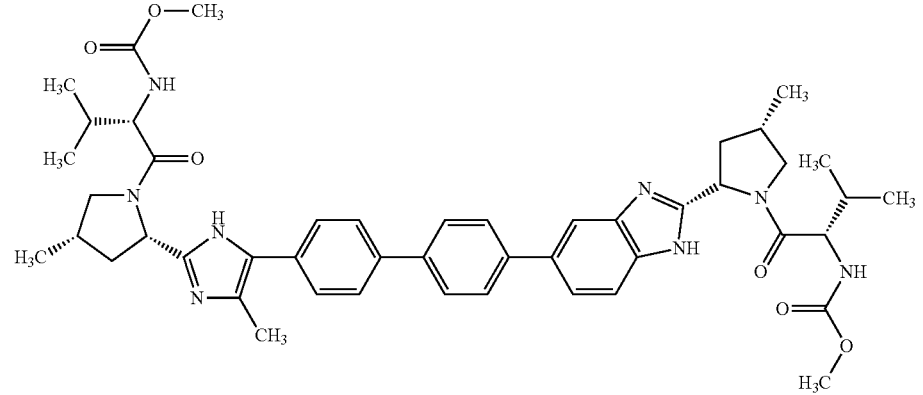 | 15 |
| 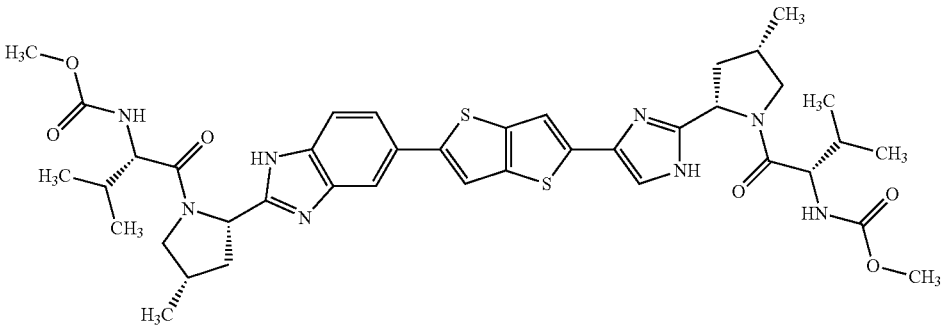 | 16 |
| 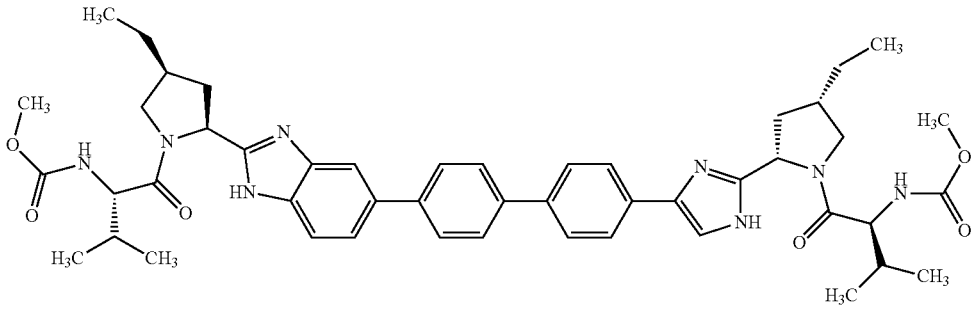 [SMILES: CC[C@H]1C[C@@H](c2nc(-c3ccc(-c4ccc(-c5ccc6[nH]c([C@@H]7C[C@H](CC)CN7C(=O)[C@@H](NC(=O)OC)C(C)C)nc6c5)cc4)cc3)c[nH]2)N(C(=O)[C@@H](NC(=O)OC)C(C)C)C1] | 17 |

TABLE 1B-continued

| Compound | # |
|---|---|
| (structure) | 19 |
| (structure) | 20 |
| (structure) | 21 |
| (structure) | 22 |

TABLE 1B-continued

| Compound | # |
|---|---|
| (structure) | 24 |
| (structure) | 25 |
| (structure) | 26 |

TABLE 1B-continued
| Compound | # |
|---|---|
| 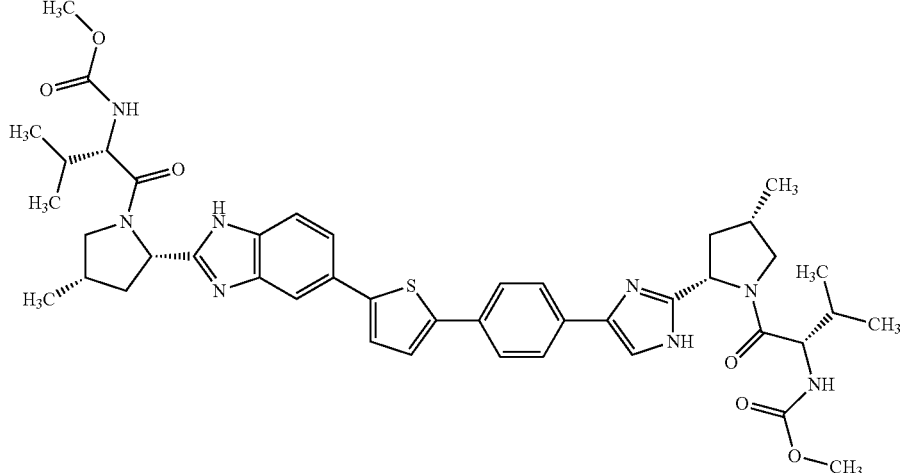 | 27 |
| 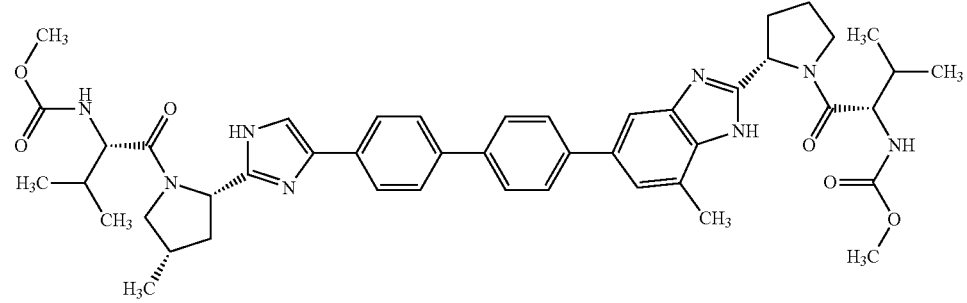 | 28 |
| 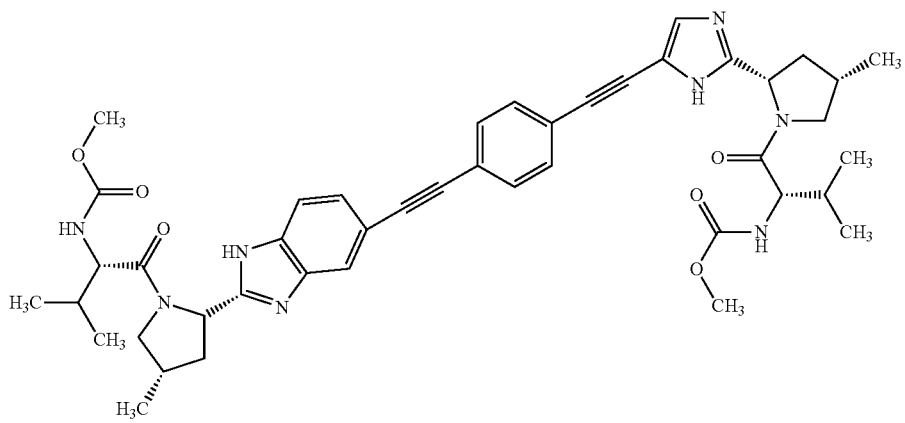 | 29 |
| 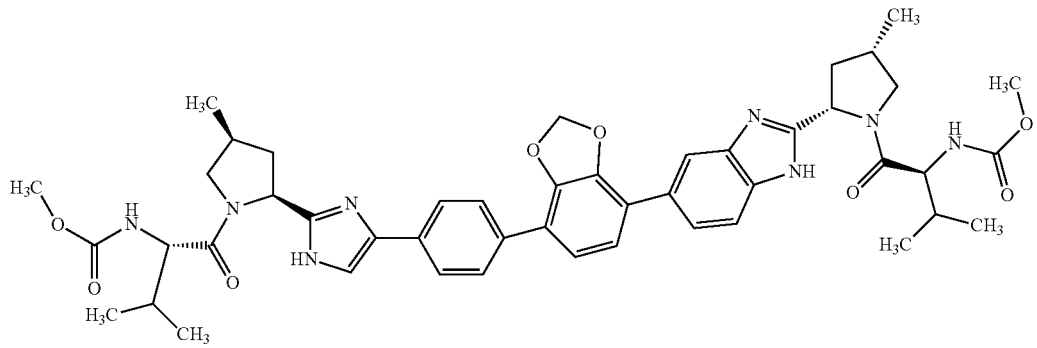 [SMILES: COC(=O)N[C@H](C(=O)N1C[C@@H](C)C[C@H]1c1nc(-c2ccc(-c3ccc(-c4ccc5[nH]c([C@@H]6C[C@H](C)CN6C(=O)[C@@H](NC(=O)OC)C(C)C)nc5c4)c4c3OCO4)cc2)c[nH]1)C(C)C] | 30 |

TABLE 1B-continued

| Compound | # |
|---|---|
| (structure) | 31 |
| (structure) | 32 |
| (structure) | 33 |
| (structure) | 34 |

TABLE 1B-continued
| Compound | # |
|---|---|
| 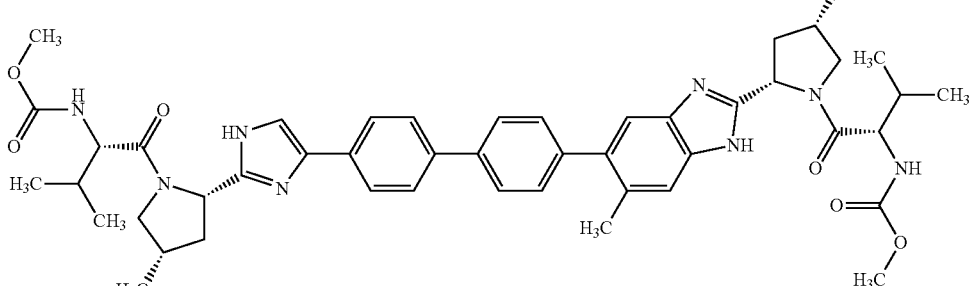 | 35 |
| 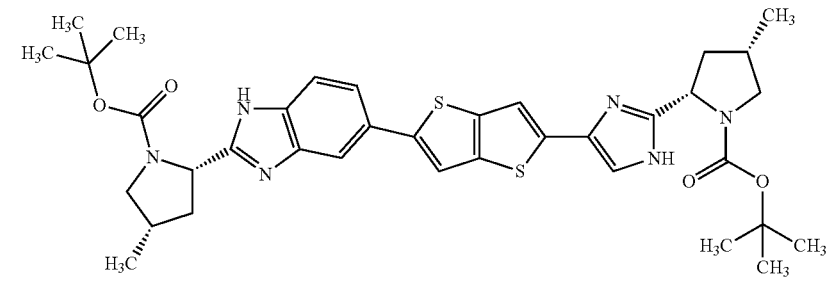 [SMILES: C[C@H]1C[C@@H](c2nc(-c3cc4sc(-c5ccc6[nH]c([C@@H]7C[C@H](C)CN7C(=O)OC(C)(C)C)nc6c5)cc4s3)c[nH]2)N(C(=O)OC(C)(C)C)C1] | 36 |
| 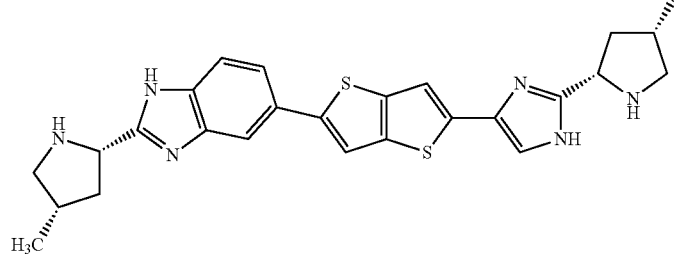 | 37 |
| 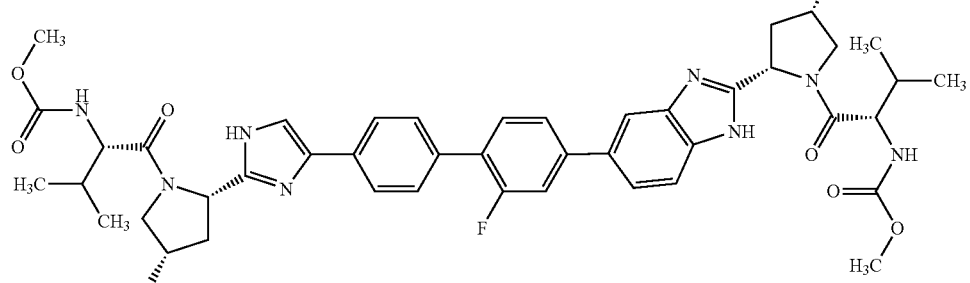 | 38 |
| 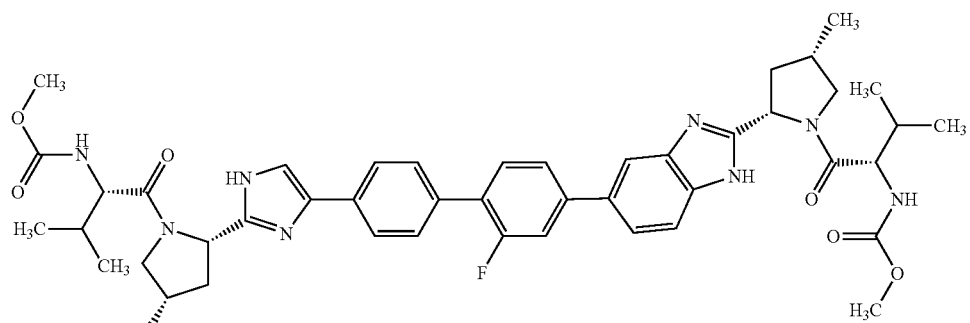 | 39 |

TABLE 1B-continued

| Compound | # |
|---|---|
| | 40 |
| | 41 |
| | 42 |
| | 43 |

TABLE 1B-continued
| Compound | # |
|---|---|
| 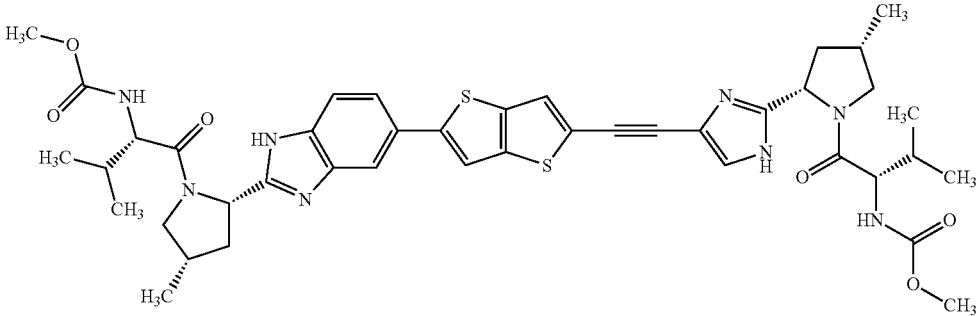 | 44 |
| 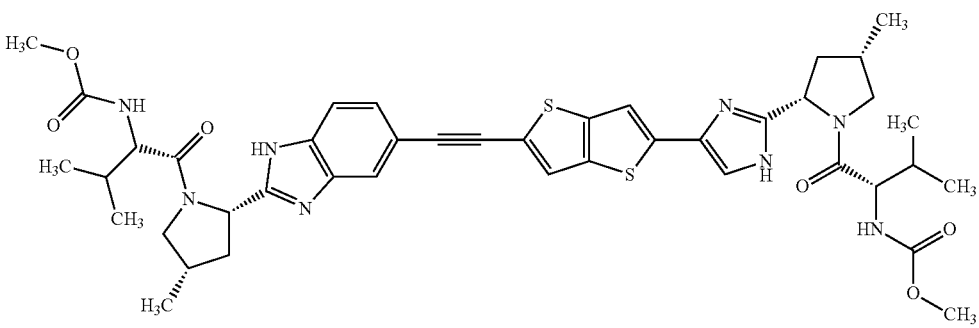 | 45 |
| 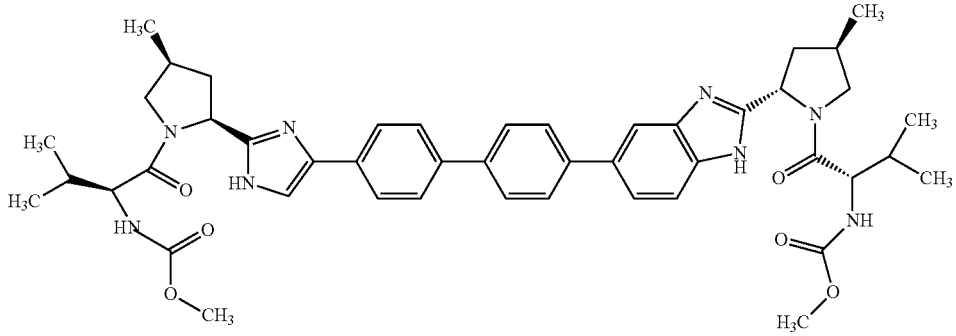 | 46 |
| 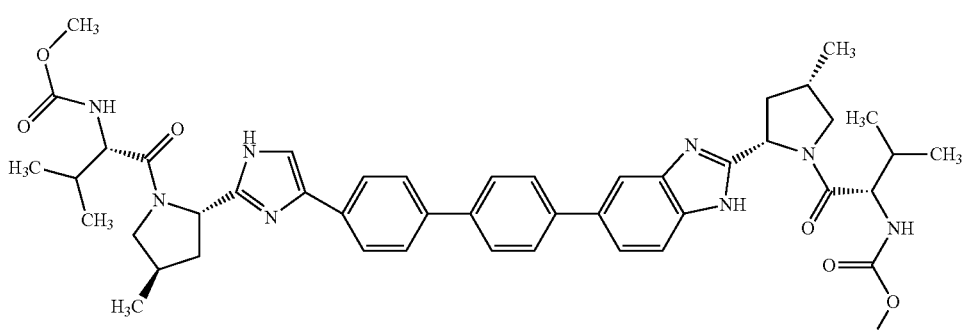 | 47 |

TABLE 1B-continued

| Compound | # |
|---|---|
| | 48 |
| | 49 |
| | 50 |
| | 51 |
| | 52 |

TABLE 1B-continued

| Compound | # |
|---|---|
| | 53 |
| | 54 |
| | 55 |
| | 56 |

TABLE 1B-continued

| Compound | # |
|---|---|
| (structure) | 57 | and pharmaceutically acceptable salts thereof.

In one embodiment, the present invention is one or more of the compounds of Table 1A or a pharmaceutically acceptable salt thereof.

In one embodiment, the present invention is one or more of the compounds of Table 1B or a pharmaceutically acceptable salt thereof.

In one embodiment, the present invention provides a compound according to the invention described herein for treating or preventing a Flaviviridae viral infection in a host.

In one embodiment, the present invention provides a pharmaceutical composition comprising at least one compound according to the invention described herein and at least one pharmaceutically acceptable carrier or excipient.

In one embodiment, the present invention provides a pharmaceutical composition comprising at least one compound according to the invention described herein and at least one pharmaceutically acceptable carrier or excipient, for treating or preventing a Flaviviridae viral infection in a host.

In one embodiment, the present invention provides a pharmaceutical composition comprising at least one compound according to the invention described herein, and further comprising administering at least one additional agent chosen from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

In another embodiment, there is provided a combination comprising a least one compound according to the invention described herein and one or more additional agents.

In another embodiment, there is provided a combination comprising a least one compound according to the invention described herein and one or more additional agents chosen from viral serine protease inhibitors, viral polymerase inhibitors, viral helicase inhibitors, immunomudulating agents, antioxidant agents, antibacterial agents, therapeutic vaccines, hepatoprotectant agents, antisense agent, inhibitors of HCV NS2/3 protease and inhibitors of internal ribosome entry site (IRES).

In one combination embodiment, the compound and additional agent are administered sequentially.

In another combination embodiment, the compound and additional agent are administered simultaneously.

The combinations referred to above may conveniently be presented for use in the form of a pharmaceutical formulation and thus pharmaceutical formulations comprising a combination as defined above together with a pharmaceutically acceptable carrier therefore comprise a further aspect of the invention.

The additional agents for the compositions and combinations include, for example, ribavirin, amantadine, merimepodib, Levovirin, Viramidine, and maxamine.

The term "viral serine protease inhibitor" as used herein means an agent that is effective to inhibit the function of the viral serine protease including HCV serine protease in a mammal. Inhibitors of HCV serine protease include, for example, those compounds described in WO 99/07733 (Boehringer Ingelheim), WO 99/07734 (Boehringer Ingelheim), WO 00/09558 (Boehringer Ingelheim), WO 00/09543 (Boehringer Ingelheim), WO 00/59929 (Boehringer Ingelheim), WO 02/060926 (BMS), WO 2006039488 (Vertex), WO 2005077969 (Vertex), WO 2005035525 (Vertex), WO 2005028502 (Vertex) WO 2005007681 (Vertex), WO 2004092162 (Vertex), WO 2004092161 (Vertex), WO 2003035060 (Vertex), of WO 03/087092 (Vertex), WO 02/18369 (Vertex), or WO98/17679 (Vertex).

In one embodiment, the present invention provides a pharmaceutical composition comprising at least one compound according to the invention described herein, and further comprising one or more additional agents chosen from viral serine protease inhibitors, viral polymerase inhibitors, viral helicase inhibitors, immunomudulating agents, antioxidant agents, antibacterial agents, therapeutic vaccines, hepatoprotectant agents, antisense agent, inhibitors of HCV NS2/3 protease and inhibitors of internal ribosome entry site (IRES).

In another embodiment, there is provided a combination therapy of at least one compound according to the invention described herein in combination with one or more additional agents chosen from viral serine protease inhibitors, viral polymerase inhibitors, viral helicase inhibitors, immunomudulating agents, antioxidant agents, antibacterial agents, therapeutic vaccines, hepatoprotectant agents, antisense agent, inhibitors of HCV NS2/3 protease and inhibitors of internal ribosome entry site (IRES).

The additional agents for the compositions and combinations include, for example, ribavirin, amantadine, merimepodib, Levovirin, Viramidine, and maxamine.

In one combination embodiment, the compound and additional agent are administered sequentially.

In another combination embodiment, the compound and additional agent are administered simultaneously. The combinations referred to above may conveniently be presented for use in the form of a pharmaceutical formulation and thus pharmaceutical formulations comprising a combination as defined above together with a pharmaceutically acceptable carrier therefore comprise a further aspect of the invention.

The term "viral serine protease inhibitor" as used herein means an agent that is effective to inhibit the function of the viral serine protease including HCV serine protease in a mammal. Inhibitors of HCV serine protease include, for example, those compounds described in WO 99/07733 (Boehringer Ingelheim), WO 99/07734 (Boehringer Ingelheim), WO 00/09558 (Boehringer Ingelheim), WO 00/09543 (Boehringer Ingelheim), WO 00/59929 (Boehringer Ingelheim), WO 02/060926 (BMS), WO 2006039488 (Vertex), WO 2005077969 (Vertex), WO 2005035525 (Vertex), WO 2005028502 (Vertex) WO 2005007681 (Vertex), WO 2004092162 (Vertex), WO 2004092161 (Vertex), WO 2003035060 (Vertex), of WO 03/087092 (Vertex), WO 02/18369 (Vertex), or WO98/17679 (Vertex).

Specific examples of viral serine protease inhibitors include Telaprevir (VX-950, Vertex), VX-500 (Vertex), TMC435350 (Tibotec/Medivir), MK-7009 (Merck), ITMN-191 (R7227, InterMune/Roche) and Boceprevir (SCH503034, Schering).

The term "viral polymerase inhibitors" as used herein means an agent that is effective to inhibit the function of a viral polymerase including an HCV polymerase in a mammal. Inhibitors of HCV polymerase include non-nucleosides, for example, those compounds described in:

WO 03/010140 (Boehringer Ingelheim), WO 03/026587 (Bristol Myers Squibb); WO 02/100846 A1, WO 02/100851 A2, WO 01/85172 A1 (GSK), WO 02/098424 A1 (GSK), WO 00/06529 (Merck), WO 02/06246 A1 (Merck), WO 01/47883 (Japan Tobacco), WO 03/000254 (Japan Tobacco) and EP 1 256 628 A2 (Agouron).

Furthermore other inhibitors of HCV polymerase also include nucleoside analogs, for example, those compounds described in: WO 01/90121 A2 (Idenix), WO 02/069903 A2 (Biocryst Pharmaceuticals Inc.), and WO 02/057287 A2(Merck/Isis) and WO 02/057425 A2 (Merck/Isis).

Specific examples of inhibitors of an HCV polymerase, include VCH-759 (ViroChem Pharma), VCH-916 (ViroChem Pharma), VCH-222 (ViroChem Pharma), R1626 (Roche), R7128 (Roche/Pharnnasset), PF-868554 (Pfizer), MK-0608 (Merck/Isis), MK-3281 (Merck), A-837093 (Abbott), GS 9190 (Gilead), ana598 (Anadys), HCV-796 (Viropharma) and GSK625433 (GlaxoSmithKline), R1479 (Roche), MK-0608 (Merck), R1656, (Roche-Pharmasset) and Valopicitabine (Idenix). Specific examples of inhibitors of an HCV polymerase, include JTK-002/003 and JTK-109 (Japan Tobacco), HCV-796 (Viropharma), GS-9190(Gilead), and PF-868,554 (Pfizer).

The term "viral helicase inhibitors" as used herein means an agent that is effective to inhibit the function of a viral helicase including a Flaviviridae helicase in a mammal.

"Immunomodulatory agent" as used herein means those agents that are effective to enhance or potentiate the immune system response in a mammal. Immunomodulatory agents include, for example, class I interferons (such as α-, β-, δ- and Ω-interferons, τ-interferons, consensus interferons and asialo-interferons), class II interferons (such as γ-interferons) and pegylated interferons.

Specific examples of Immunomodulatory agent as used herein include IL-29 (PEG-Interferon Lambda, ZymoGenetics), Belerofon (Nautilus Biotech) injectable or oral, Oral Interferon alpha (Amarillo Biosciences), BLX-883 (Locteron, Biolex Therapeutics/Octoplus), Omega Interferon (Intarcia Therapeutics), multiferon (Viragen), Albuferon (Human Genome Sciences), consensus Interferon (Infergen, Three Rivers Pharmaceuticals), Medusa Interferon (Flannel Technologies), NOV-205 (Novelos Therapeutics), Oglufanide disodium (Implicit Bioscience), SCV-07 (SciClone), Zadaxin® (thymalfasin, SciClone/Sigma-Tau), AB68 (XTL bio) and Civacir (NABI).

The term "viral polymerase inhibitors" as used herein means an agent that is effective to inhibit the function of a viral polymerase including an HCV polymerase in a mammal. Inhibitors of HCV polymerase include non-nucleosides, for example, those compounds described in: WO 03/010140 (Boehringer Ingelheim), WO 03/026587 (Bristol Myers Squibb); WO 02/100846 A1, WO 02/100851 A2, WO 01/85172 A1 (GSK), WO 02/098424 A1 (GSK), WO 00/06529 (Merck), WO 02/06246 A1 (Merck), WO 01/47883 (Japan Tobacco), WO 03/000254 (Japan Tobacco) and EP 1 256 628 A2 (Agouron).

Furthermore other inhibitors of HCV polymerase also include nucleoside analogs, for example, those compounds described in: WO 01/90121 A2 (Idenix), WO 02/069903 A2 (Biocryst Pharmaceuticals Inc.), and WO 02/057287 A2 (Merck/Isis) and WO 02/057425 A2 (Merck/Isis).

Specific examples of nucleoside inhibitors of an HCV polymerase, include R1626/R1479 (Roche), R7128 (Roche), MK-0608 (Merck), R1656, (Roche-Pharmasset) and Valopicitabine (Idenix). Specific examples of inhibitors of an HCV polymerase, include JTK-002/003 and JTK-109 (Japan Tobacco), HCV-796 (Viropharma), GS-9190(Gilead), and PF-868,554 (Pfizer).

The term "viral helicase inhibitors" as used herein means an agent that is effective to inhibit the function of a viral helicase including a Flaviviridae helicase in a mammal.

"Immunomodulatory agent" as used herein means those agents that are effective to enhance or potentiate the immune system response in a mammal. Immunomodulatory agents include, for example, class I interferons (such as alpha-, beta-, delta- and omega-interferons, x-interferons, consensus interferons and asialo-interferons), class II interferons (such as gamma-interferons) and pegylated interferons.

Exemplary immunomudulating agents, include, but are not limited to: thalidomide, IL-2, hematopoietins, IMPDH inhibitors, for example Merimepodib (Vertex Pharmaceuticals Inc.), interferon, including natural interferon (such as OMNIFERON, Viragen and SUMIFERON, Sumitomo, a blend of natural interferon's), natural interferon alpha (ALFERON, Hemispherx Biopharma, Inc.), interferon alpha n1 from lymphblastoid cells (WELLFERON, Glaxo Wellcome), oral alpha interferon, Peg-interferon, Peg-interferon alfa 2a (PEGASYS, Roche), recombinant interferon alpha 2a (ROFERON, Roche), inhaled interferon alpha 2b (AERX, Aradigm), Peg-interferon alpha 2b (ALBUFERON, Human Genome Sciences/Novartis, PEGINTRON, Schering), recombinant interferon alfa 2b (INTRON A, Schering), pegylated interferon alfa 2b (PEG-INTRON, Schering, VIRAFERONPEG, Schering), interferon beta-1a (REBIF, Serono, Inc. and Pfizer), consensus interferon alpha (INFERGEN, Valeant Pharmaceutical), interferon gamma-1b (ACTIMMUNE, Intermune, Inc.), un-pegylated interferon alpha, alpha interferon, and its analogs, and synthetic thymosin alpha 1 (ZADAXIN, SciClone Pharmaceuticals Inc.).

The term "class I interferon" as used herein means an interferon selected from a group of interferons that all bind to receptor type 1. This includes both naturally and synthetically produced class I interferons. Examples of class I interferons include α-, β-, δ- and Ω-interferons, τ-interferons, consensus interferons and asialo-interferons. The term "class II interferon" as used herein means an interferon selected from a group of interferons that all bind to receptor type II. Examples of class II interferons include γ-interferons.

Antisense agents include, for example, ISIS-14803.

Specific examples of inhibitors of HCV NS3 protease, include BILN-2061 (Boehringer Ingelheim) SCH-6 and SCH-503034/Boceprevir(Schering-Plough), VX-950/telaprevir(Vertex) and ITMN-B (InterMune), GS9132 (Gilead), TMC-435350(Tibotec/Medivir), ITMN-191 (InterMune), MK-7009 (Merck).

Inhibitors of internal ribosome entry site (IRES) include ISIS-14803 (ISIS Pharmaceuticals) and those compounds described in WO 2006019831 (PTC therapeutics).

In one embodiment, the additional agent is interferon α, ribavirin, silybum marianum, interleukine-12, amantadine, ribozyme, thymosin, N-acetyl cysteine or cyclosporin.

In one embodiment, the additional agent is interferon α, or ribavirin, silybum marianum, interleukine-12, amantadine, ribozyme, thymosin, N-acetyl cysteine or cyclosporin.

In one embodiment, the additional agent is interferon α 1A, interferon α 1B, interferon α 2A, or interferon α 2B.

Interferon is available in pegylated and non pegylated forms. Pegylated interferons include PEGASYS™ and Peg-intron™.

The recommended dose of PEGASYS™ monotherapy for chronic hepatitis C is 180 mg (1.0 mL vial or 0.5 mL prefilled syringe) once weekly for 48 weeks by subcutaneous administration in the abdomen or thigh.

The recommended dose of PEGASYS™ when used in combination with ribavirin for chronic hepatitis C is 180 mg (1.0 mL vial or 0.5 mL prefilled syringe) once weekly.

The recommended dose of PEG-Intron™ regimen is 1.0 mg/kg/week subcutaneously for one year. The dose should be administered on the same day of the week.

When administered in combination with ribavirin, the recommended dose of PEG-Intron is 1.5 micrograms/kg/week.

Ribavirin is typically administered orally, and tablet forms of ribavirin are currently commercially available. General standard, daily dose of ribavirin tablets (e.g., about 200 mg tablets) is about 800 mg to about 1200 mg. For example, ribavirn tablets are administered at about 1000 mg for subjects weighing less than 75 kg, or at about 1200 mg for subjects weighing more than or equal to 75 kg. Nevertheless, nothing herein limits the methods or combinations of this invention to any specific dosage forms or regime. Typically, ribavirin can be dosed according to the dosage regimens described in its commercial product labels.

In one embodiment, the additional agent is interferon α 1A, interferon α 1B, interferon α 2A (Roferon), PEG-interferon α 2A (Pegasys), interferon α 2B (Intron A) or PEG-interferon α 2B (Peg-Intron).

In one embodiment, the additional agent is standard or pegylated interferon α (Roferon, Pegasys, Intron A, Peg-Intron) in combination with ribavirin.

In one embodiment, the present invention provides a pharmaceutical composition comprising at least one compound according to the invention described herein, one or more additional agents select from non-nucleoside HCV polymerase inhibitors (e.g., HCV-796), nucleoside HCV polymerase inhibitors (e.g., R7128, R1626/R1479), HCV NS3 protease inhibitors (e.g., VX-950/telaprevir and ITMN-191), interferon and ribavirin, and at least one pharmaceutically acceptable carrier or excipient.

The combinations referred to above may conveniently be presented for use in the form of a pharmaceutical formulation and thus pharmaceutical formulations comprising a combination as defined above together with a pharmaceutically acceptable carrier therefore comprise a further aspect of the invention. The individual components for use in the method of the present invention or combinations of the present invention may be administered either sequentially or simultaneously in separate or combined pharmaceutical formulations.

In a further embodiment, the composition or combination according to the invention further comprises at least one compound according to the invention described herein; one or more additional agents select from non-nucleoside HCV polymerase inhibitors (e.g., HCV-796), nucleoside HCV polymerase inhibitors (e.g., R7128, R1626/R1479), and HCV NS3 protease inhibitors (e.g., VX-950/telaprevir and ITMN-191); and interferon and/or ribavirin.

In one embodiment, the additional agent is interferon α 1A, interferon α 1B, interferon α 2A, or interferon α 2B, and optionally ribavirin.

In one embodiment, the present invention provides a method for treating or preventing a HCV viral infection in a host comprising administering to the host a combined therapeutically effective amounts of at least one compound according to the invention described herein, and one or more additional agents select from non-nucleoside HCV polymerase inhibitors (e.g., HCV-796), nucleoside HCV polymerase inhibitors (e.g., R7128, R1626/R1479), HCV NS3 protease inhibitors (e.g., VX-950/telaprevir and ITMN-191), interferon and ribavirin.

In one combination embodiment, the compound and additional agent are administered sequentially.

In another combination embodiment, the compound and additional agent are administered simultaneously.

In one embodiment, there is provided a method for inhibiting or reducing the activity of HCV viral polymerase in a host comprising administering to the host a combined therapeutically effective amounts of at least one compound of the invention, and one or more additional agents select from non-nucleoside HCV polymerase inhibitors (e.g., HCV-796) and nucleoside HCV polymerase inhibitors (e.g., R7128, R1626/R1479), interferon and ribavirin.

In one embodiment, the present invention provides the use of at least one compound of the invention, in combination with the use of one or more additional agents select from non-nucleoside HCV polymerase inhibitors (e.g., HCV-796), nucleoside HCV polymerase inhibitors (e.g., R7128, R1626/R1479), HCV NS3 protease inhibitors (e.g., VX-950/telaprevir and ITMN-191), interferon and ribavirin, for the manufacture of a medicament for treating or preventing a HCV infection in a host.

When the compounds of the invention described herein are used in combination with at least one second therapeutic agent active against the same virus, the dose of each compound may be either the same as or differ from that when the compound is used alone. Appropriate doses will be readily appreciated by those skilled in the art.

The ratio of the amount of a compound according to the invention described herein administered relative to the amount of the additional agent (non-nucleoside HCV polymerase inhibitors (e.g., HCV-796), nucleoside HCV polymerase inhibitors (e.g., R7128, R1626/R1479), HCV NS3 protease inhibitors (e.g., VX-950/telaprevir and ITMN-191), interferon or ribavirin) will vary dependent on the selection of the compound and additional agent.

In one embodiment, the additional agent is chosen from A-831 (AZD0530, Arrow Therapeutics acquired by Astra-Zeneca), TLR9 agonist: IMO-2125 (Idera Pharmaceuticals), PYN17 (Phynova), Vavituximab (Tarvacin, Peregrine), DEBIO-025 (DEBIO), NIM-811 (Novartis), SCY635 (Scynexis), PF-03491390 (IDN-6556, Pfizer), Suvus (formerly BIVN-401, Virostat, Bioenvision), MX-3253 (Celgosivir, Migenix), Viramidine (Taribavirin, Valeant Pharmaceuticals), Hepaconda (Giaconda), TT033 (Benitec/Tacere Bio/Pfizer), SIRNA-034 (Sirna Therapeutics aquired by Merck) and EHC-18 (Enzo Biochem), ACH-1095 (Achillion/Gilead), JKB-022 (Jenkin), CTS-1027 (Conatus), MitoQ (mitoquinone, Antipodean Pharmaceuticals), Alinia (nitazoxanide, Romark Laboratories) and Bavituximab (Peregrine Pharm).

In one embodiment, the additional agent is a therapeutic vaccine chosen from CSL123 (Chiron/CSL), IC41 (Intercell Novartis), GI 5005 (Globeimmune), TG4040 (Transgene), Chronvac C (Tripep/Inovio), GNI-103 (GENimmune), HCV/MF59 (Chiron/Novartis), PeviPRO™ (Pevion biotect).

The recommended dose of PEGASYS™ monotherapy for chronic hepatitis C is 180 mg (1.0 mL vial or 0.5 mL prefilled syringe) once weekly for 48 weeks by subcutaneous administration in the abdomen or thigh.

In one embodiment, viral serine protease inhibitor is a flaviviridae serine protease inhibitor.

In one embodiment, viral polymerase inhibitor is a flaviviridae polymerase inhibitor.

In one embodiment, viral helicase inhibitor is a flaviviridae helicase inhibitor.

In further embodiments:
viral serine protease inhibitor is HCV serine protease inhibitor;
viral polymerase inhibitor is HCV polymerase inhibitor;
viral helicase inhibitor is HCV helicase inhibitor.

In one embodiment, the present invention provides a method for treating or preventing a Flaviviridae viral infection in a host comprising administering to the host a therapeutically effective amount of at least one compound according to formula (I), (II), (III), or (IV).

In one embodiment, the viral infection is chosen from Flavivirus infections.

In one embodiment, the Flavivirus infection is Hepatitis C virus (HCV), bovine viral diarrhea virus (BVDV), hog cholera virus, dengue fever virus, Japanese encephalitis virus or yellow fever virus.

In one embodiment, the Flaviviridea viral infection is hepatitis C viral infection (HCV).

In one embodiment, the host is human.

In one embodiment, the present invention provides a method for treating or preventing a Flaviviridae viral infection in a host comprising administering to the host a therapeutically effective amount of at least one compound according to the invention described herein, and further comprising administering at least one additional agent.

In one embodiment, the present invention provides a method for treating or preventing a Flaviviridae viral infection in a host comprising administering to the host a therapeutically effective amount of at least one compound according to the invention described herein, and further comprising administering at least one additional agent chosen from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

The combinations referred to above may conveniently be presented for use in the form of a pharmaceutical formulation and thus pharmaceutical formulations comprising a combination as defined above together with a pharmaceutically acceptable carrier therefore comprise a further aspect of the invention.

The individual components for use in the method of the present invention or combinations of the present invention may be administered either sequentially or simultaneously in separate or combined pharmaceutical formulations.

In one embodiment, the present invention provides the use of a compound according to the invention described herein for treating or preventing Flaviviridae viral infection in a host.

In one embodiment, the present invention provides the use of a compound according to the invention described herein and further comprising at least one additional agent chosen from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES). for treating or preventing Flaviviridae viral infection in a host.

In one embodiment, the present invention provides the use of a compound according to the invention described herein for the manufacture of a medicament.

In one embodiment, the present invention provides the use of a compound according to the invention described herein for the manufacture of a medicament for treating or preventing a viral Flaviviridae infection in a host.

In one embodiment, the present invention provides the use of a compound according to the invention described herein and further comprising at least one additional agent chosen from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES). for the manufacture of a medicament for treating or preventing a viral Flaviviridae infection in a host.

In one embodiment, the present invention provides a method of treating or preventing infection by a HCV virus, comprising contacting a biological sample or administering to a patient in need thereof a compound disclosed herein in an amount effective to treat or prevent the infection.

In one embodiment of the method, HCV is of genotype 1. In another embodiment, HCV is of genotype 1a, genotype 1b, or a combination thereof.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. The single optical isomer or enantiomer can be obtained by method well known in the art, such as chiral HPLC, enzymatic resolution and chiral auxiliary.

Unless otherwise stated, all tautomeric forms of the compounds of the invention are within the scope of the invention.

In one embodiment, the compounds of the present invention are provided in the form of a single stereoisomer at least 95%, at least 97% and at least 99% free of the corresponding stereoisomers.

In a further embodiment the compound of the present invention are in the form of a single stereoisomer at least 95% free of the corresponding stereoisomers.

In a further embodiment the compound of the present invention are in the form of a single stereoisomer at least 97% free of the corresponding stereoisomers.

In a further embodiment the compound of the present invention are in the form of a single stereoisomer at least 99% free of the corresponding stereoisomers.

There is also provided pharmaceutically acceptable salts of the compounds of the present invention. By the term pharmaceutically acceptable salts of compounds are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not themselves pharmaceutically acceptable, may be useful as intermediates in obtaining the compounds of the invention and their pharmaceutically acceptable acid addition salts.

Salts derived from amino acids are also included (e.g. L-arginine, L-Lysine).

Salts derived from appropriate bases include alkali metals (e.g. sodium, lithium, potassium) and alkaline earth metals (e.g. calcium, magnesium).

A reference hereinafter to a compound according to the invention includes that compound and its pharmaceutically acceptable salts.

With regards to pharmaceutically acceptable salts, see also the list of FDA approved commercially marketed salts listed in Table I of Berge et al., Pharmaceutical Salts, J. of Phar. Sci., vol. 66, no. 1, January 1977, pp. 1-19, the disclosure of which is incorporated herein by reference.

It will be appreciated by those skilled in the art that the compounds in accordance with the present invention can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

It will further be appreciated by those skilled in the art that the compounds in accordance with the present invention can exist in different solvate forms, for example hydrates. Solvates of the compounds of the invention may also form when solvent molecules are incorporated into the crystalline lattice structure of the compound molecule during the crystallization process.

In addition to the compounds of this invention, pharmaceutically acceptable derivatives or prodrugs, and esters, of the compounds of this invention may also be employed in compositions to treat or prevent the herein identified disorders. Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

In the formulas and drawings, a line transversing a ring and bonded to a group such as B, B', $R_1$, $R_4$ or $R_4'$ in formula (I)

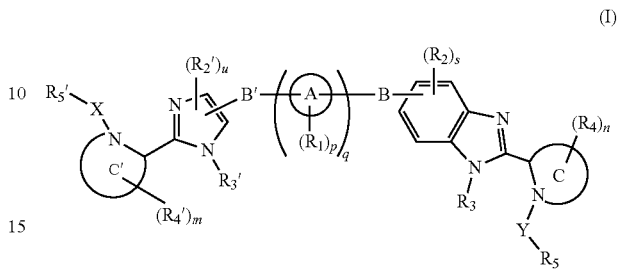

(I)

means that the group can be bonded to any carbon, or if applicable, heteroatom such as N, of that ring as valency allows.

The term "alkyl" represents a linear, branched or cyclic hydrocarbon moiety. The terms "alkenyl" and "alkynyl" represent a linear, branched or cyclic hydrocarbon moiety which has one or more double bonds or triple bonds in the chain. Examples of alkyl, alkenyl, and alkynyl groups include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, allyl, vinyl, acetylenyl, ethylenyl, propenyl, isopropenyl, butenyl, isobutenyl, hexenyl, butadienyl, pentenyl, pentadienyl, hexenyl, heptenyl, heptadienyl, heptatrienyl, octenyl, propynyl, butynyl, pentynyl, hexynyl, cyclopropyl, cyclobutyl, cyclohexenyl, cyclohexdienyl and cyclohexyl. The terms alkyl, alkenyl, and alkynyl, also include combinations of linear and branched groups, e.g., cyclopropylmethyl, cyclohexylethyl, etc. The term alkenyl also includes C1 alkenyl where the one carbon atom is attached to the remainder of the molecule via a double bond. Where indicated the "alkyl," "alkenyl," and "alkynyl" can be optionally substituted such as in the case of haloalkyls in which one or more hydrogen atom is replaced by a halogen, e.g., an alkylhalide. Examples of haloalkyls include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl. Aside from halogens, where indicated, the alkyl, alkenyl or alkynyl groups can also be optionally substituted by, for example, halogen, $-OR_a$, oxo, $-NR_aR_b$, $=NO-R_c$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, or $-P(=O)OR_aOR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

The terms "cycloalkyl", and "cycloalkenyl" represent a cyclic hydrocarbon alkyl or alkenyl, respectively, and are meant to include monocyclic (e.g., cyclopropyl, cyclobutyl, cyclohexyl), spiro (e.g., spiro[2.3]hexanyl), fused (e.g., bicyclo[4.4.0]decanyl), and bridged (e.g., bicyclo[2.2.1]heptanyl)hydrocarbon moieties.

The terms "alkoxy," "alkenyloxy," and "alkynyloxy" represent an alkyl, alkenyl or alkynyl moiety, respectively, which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, trifluoromethoxy and neohexyloxy. Like the alkyl, alkenyl and alkynyl groups, where indicated the alkoxy, alkenyloxy, and alkynyloxy groups can be optionally substituted by, for example, halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

The term "aryl" represents a carbocyclic moiety containing at least one benzenoid-type ring (i.e., may be monocyclic or polycyclic), and which where indicated may be optionally substituted with one or more substituents. Examples include but are not limited to phenyl, tolyl, dimethylphenyl, aminophenyl, anilinyl, naphthyl, anthryl, phenanthryl or biphenyl. The aryl groups can be optionally substituted where indicated by, for example, halogen, —$OR_a$, —$NR_aR_b$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

The term "aralkyl" represents an aryl group attached to the adjacent atom by an alkyl, alkenyl or alkynyl. Like the aryl groups, where indicated the aralkyl groups can also be optionally substituted. Examples include but are not limited to benzyl, benzhydryl, trityl, phenethyl, 3-phenylpropyl, 2-phenylpropyl, 4-phenylbutyl and naphthylmethyl. Where indicated, the aralkyl groups can be optionally substituted one or more times by, for example, halogen, —$OR_a$, —$NR_aR_b$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

The term "heterocycle" represents a non aromatic, saturated or partially saturated cyclic moiety wherein said cyclic moiety is interrupted by at least one heteroatom selected from oxygen (O), sulfur (S) or nitrogen (N). Heterocycles may be monocyclic or polycyclic rings. Examples include but are not limited to azetidinyl, dioxolanyl, morpholinyl, morpholino, oxetanyl, piperazinyl, piperidyl, piperidinyl, cyclopentapyrazolyl, cyclopentaoxazinyl, cyclopentafuranyl, tetrahydrofuranyl, thiazolinyl, oxazolinyl, pyranyl, aziridinyl, azepinyl, dioxazepinyl, diazepinyl, oxyranyl, oxazinyl, pyrrolidinyl, and thiopyranyl, thiolanyl, pyrazolidinyl, dioxanyl, and imidazolidinyl. Where indicated, the heterocyclic groups can be optionally substituted one or more times by, for example, halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

The term "heterocycle-alkyl" represents a heterocycle group attached to the adjacent atom by an alkyl, alkenyl or alkynyl group. It is understood that in, for example, a 4-18 member heterocycle-alkyl moiety, the 4-18 member represent the total of the ring atoms present in the heterocycle moiety and the carbon atoms present in the alkyl, alkenyl or alkynyl group. For example, the following groups are encompassed by a 7 member heterocycle-alkyl (* represents the attachment point):

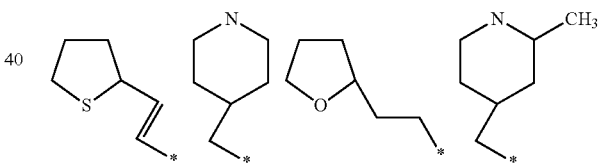

Where indicated the heterocycle-alkyl groups can be optionally substituted one or more times by, for example, halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

The term "heteroaryl" represents an aromatic cyclic moiety wherein said cyclic moiety is interrupted by at least one heteroatom selected from oxygen (O), sulfur (S) or nitrogen (N). Heteroaryls may be monocyclic or polycyclic rings wherein at least one ring in the polycyclic ring system is aromatic and at least one ring (not necessarily the same ring contains a heteroatom. Examples include but are not limited to dithiadiazinyl, furanyl, isooxazolyl, isothiazolyl, imidazolyl, oxadiazolyl, oxazolyl, pyrazinyl, pyridazinyl, pyrinnidinyl, pyridyl, pyrazolyl, pyrrolyl, thiatriazolyl, tetrazolyl, thiadiazolyl, triazolyl, thiazolyl, thienyl, tetrazinyl, thiadiazinyl, triazinyl, thiazinyl, furoisoxazolyl, imidazothiazolyl, thienoisothiazolyl, thienothiazolyl, imidazopyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, benzodioxolyl, dihydrobenzodioxinyl, benzothiadiazolyl, thienofuranyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, benzoxazinyl, benzothiazinyl, quinazolinyl, naphthyridinyl, quinolinyl, isoquinolinyl, benzopyranyl, pyridopyridazinyl, chromen, benzodiazinyl. Where indicated the heteroaryl groups can be optionally substituted one or more times by, for example, halogen, —OR$_a$, —NR$_a$R$_b$, —C(═O)OR$_a$, —C(O)NR$_a$R$_b$, —C(═O)OH, —C(═O)R$_a$, —C(═NOR$_c$)R$_a$, —C(═NR$_c$)NR$_a$R$_b$, —NR$_d$C(═O)NR$_a$R$_b$, —NR$_b$C(═O)R$_a$, —NR$_d$C(═NR$_c$)NR$_a$R$_b$, —NR$_b$C(═O)OR$_a$, —OC(═O)NR$_a$R$_b$, —OC(═O)R$_a$, —OC(═O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(═O)OR$_a$OR$_b$, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

The term "heteroaralkyl" represents an optionally substituted heteroaryl group attached to the adjacent atom by an alkyl, alkenyl or alkynyl group. Where indicated the heteroaralkyl groups can be optionally substituted one or more times by, for example, halogen, —OR$_a$, —NR$_a$R$_b$, —C(═O)OR$_a$, —C(O)NR$_a$R$_b$, —C(═O)OH, —C(═O)R$_a$, —C(═NOR$_c$)R$_a$, —C(═NR$_c$)NR$_a$R$_b$, —NR$_d$C(═O)NR$_a$R$_b$, —NR$_b$C(═O)R$_a$, —NR$_d$C(═NR$_c$)NR$_a$R$_b$, —NR$_b$C(═O)OR$_a$, —OC(═O)NR$_a$R$_b$, —OC(═O)R$_a$, —OC(═O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(═O)OR$_a$OR$_b$, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl. It is understood that in, for example, a 6-18 member heteroaralkyl moiety, the 6-18 member represents the total of the ring atoms present in the heterocycle moiety and the carbon atoms in the alkyl, alkenyl or alkynyl groups. For example, the following groups are encompassed by a 7 member heteroaralkyl (* represents the attachment point):

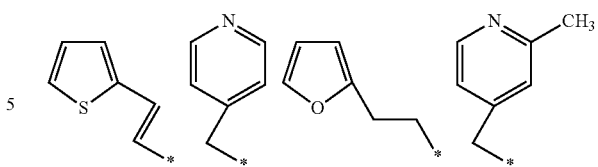

"Halogen atom or halo" is specifically a fluorine atom, chlorine atom, bromine atom or iodine atom.

The term "oxo" represents ═O.

A dash ("-") that is not between two letters or symbols is used to indicate a point of attachment for a substituent. For example, —CONR$_d$R$_e$ is attached through the carbon of the amide.

A dash line ("- - - - -") is used to indicate the point of attachment for the group. For example, A is attached through the carbon at position 1 and 4 in the following representation:

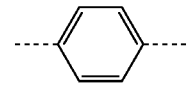

When there is a sulfur atom present, the sulfur atom can be at different oxidation levels, i.e., S, SO, or SO$_2$. All such oxidation levels are within the scope of the present invention.

The term "independently" means that a substituent can be the same or a different definition for each item.

In general, the term "substituted," whether preceded by the term "optionally" or not, refers to the replacement of hydrogen radicals on a carbon or nitrogen atom in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. For example, the language, "which is unsubstituted or substituted one or more times by R$^{10}$" means that when the group is substituted with more than one R$^{10}$ group, the R$^{10}$ groups can be different from each other. A ring substituent, such as a heterocycle, can be bound to another ring, such as a cycloalkyl, to form a spiro-bicyclic ring system, e.g., both rings share one common atom.

As one of ordinary skill in the art will recognize, combinations of substituents envisioned by this invention are those combinations that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. When two alkoxy groups are bound to the same atom or adjacent atoms, the two alkoxy groups can form a ring together with the atom(s) to which they are bound.

In certain embodiments, a compound represented by:

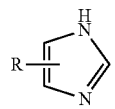

also includes where the R group replaces the H on the nitrogen atom.

Additionally, unless otherwise stated, structures depicted herein are also meant to include compounds that differ only in the presence of one or more isotopically enriched atoms. For example, compounds of this invention, wherein one or more hydrogen atoms are replaced deuterium or tritium, or one or more carbon atoms are replaced by a $^{13}$C- or $^{14}$C-enriched carbon are within the scope of this invention. Such compounds are useful, for example, as analytical tools, probes in biological assays, or antiviral compounds with improved therapeutic profile.

The terms "host" or "patient" mean human male or female, for example child, adolescent or adult.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, for example, in the range of 0.5 to 60 mg/kg/day, or, for example, in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 μM, about 2 to 50 μM, about 3 to about 30 μM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

When the compounds of the present invention or a pharmaceutically acceptable salts thereof is used in combination with a second therapeutic agent active against the same virus the dose of each compound may be either the same as or differ from that when the compound is used alone. Appropriate doses will be readily appreciated by those skilled in the art.

While it is possible that, for use in therapy, a compound of the invention may be administered as the raw chemical it is preferable to present the active ingredient as a pharmaceutical composition. The invention thus further provides a pharmaceutical composition comprising compounds of the present invention or a pharmaceutically acceptable derivative thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Compositions suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical compositions suitable for rectal administration wherein the carrier is a solid are for example presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Compositions suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilizing agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The following general schemes and examples are provided to illustrate various embodiments of the present invention and shall not be considered as limiting in scope. It will be appreciated by those of skill in the art that other compounds of the present invention can be obtained by substituting the generically or specifically described reactants and/or operating conditions used in the following examples.

In the foregoing and in the following examples, all temperatures are set forth uncorrected in degrees Celsius; and, unless otherwise indicated, all parts and percentages are by weight.

The following abbreviations may be used as follows:

| | |
|---|---|
| aq | aqueous |
| conc | concentrate |
| DCM | methylene chloride |
| DIPEA | Diisopropylethylamine |
| DMF | dimethylformamide |
| DMSO | Dimethylsulfoxide |
| EtOAc | Ethyl acetate |
| HATU | O-(7-Azabenzotriazol-1-yl)-N,N,N',N'-tetramethyl-uronium hexafluorophosphate |
| M | molar |
| MeOH | Methanol |
| MTBE | methyl ter-butyl ether |
| n-BuLi | n-butyl lithium |
| PdCl$_2$dppf | (1,1'-Bis-(diphenylphosphino)-ferrocene)palladium (II) dichloride |
| Pd(PPh$_3$)$_2$Cl$_2$ | trans-dichlorobis(triphenyl phosphine) Palladium (II) |
| RT | room temperature |
| TEA | Triethylamine |
| THF | Tetrahydrofuran |

The compounds of this invention may be prepared in light of the specification using steps generally known to those of ordinary skill in the art. Those compounds may be analyzed by known methods, including but not limited to LCMS (liquid chromatography mass spectrometry) HPLC (high performance liquid chromatography) and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following schemes are as defined herein. General Schemes:

Mass spec. samples were analyzed on a MicroMass Quattro Micro of MicroMass LCZ mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture. Method A: Column gradient conditions were 5%-100% acetonitrile-methanol over 3.5 mins gradient time and 4.8 mins run time on an ACE5C8 3.0×75 mm column. Flow rate was 1.2 ml/min. Method B: Column gradient were 5%-100% acetonitrile-methanol over 10 mins gradient time and 12 mins run time on a ACE5C8 4.6×150 mm column. Flow rate was 1.5 mL/min. As used herein, the term "Rt (min)" refers to the LCMS retention time, in minutes, associated with the compound. Unless otherwise indicated, the LCMS method utilized to obtain the reported retention time is as detailed above. If the Rt(min) is <5 min method A was used, if the Rt(min) is >5 min then method B was used.

1H-NMR spectra were recorded at 400 MHz using a Bruker DPX 400 or Varian instrument.

Purification by reverse phase HPLC is carried out under standard conditions using a Phenomenex Gemini C18 column, 21.2 mmID×250 mm, 5 µm, 110 Å. Elution is performed using a linear gradient 20 to 90% (CH$_3$CN in water or CH$_3$CN in water with 0.02% HCl) with a flow rate of 5.0 mL/minute.

EXAMPLES

Purification by reverse phase HPLC is carried out under standard conditions using a Phenomenex Gemini C18 column, 21.2 mmID×250 mm, 5 µm, 110 Å. Elution is performed using a linear gradient 20 to 90% (CH$_3$CN in water or CH$_3$CN in water with 0.02% HCl) with a flow rate of 5.0 mL/minute.

Example 1

((S)-1-{(2S,4S)-2-[5-(4'-{2-[(2S,4S)-1-((S)-2-Methoxycarbonylamino-3-methyl-butyryl)-4-methyl-pyrrolidin-2-yl]-1H-imidazol-4-yl}-biphenyl-4-yl)-1H-benzoimidazol-2-yl]-4-methyl-pyrrolidine-1-carbonyl}-2-methyl-propyl)-methyl-carbamic acid methyl ester (Compound 7)

-continued
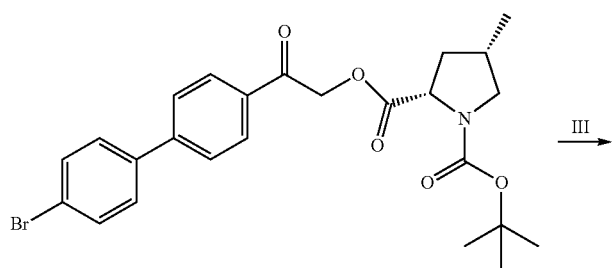 III →
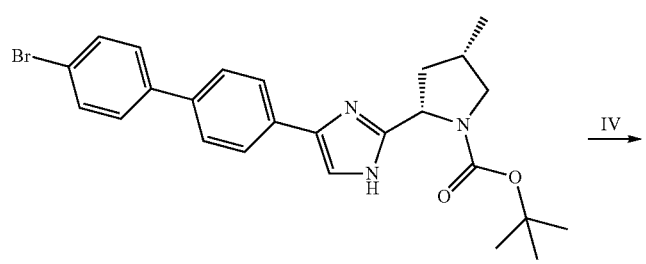 IV →
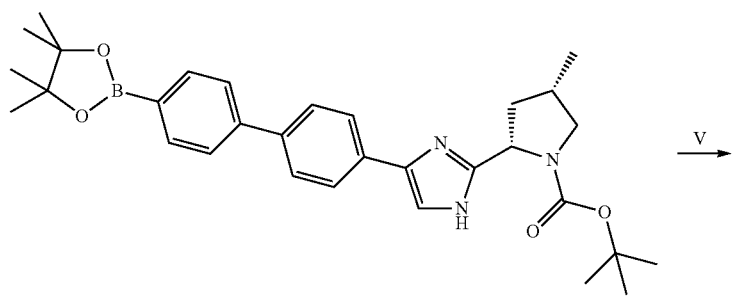 V →
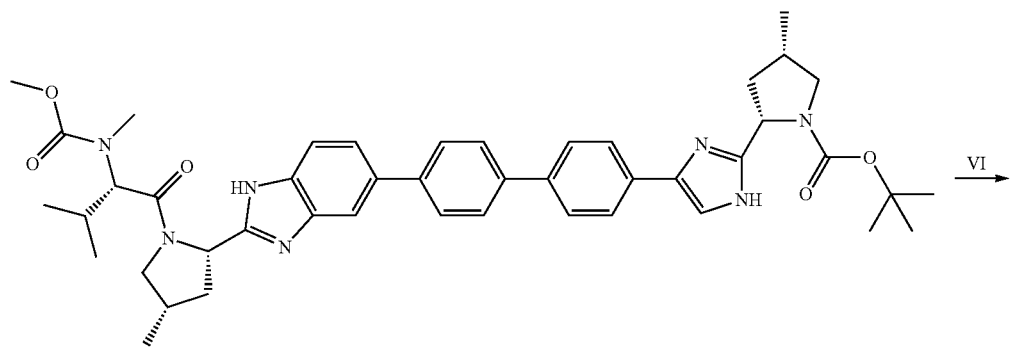 VI →
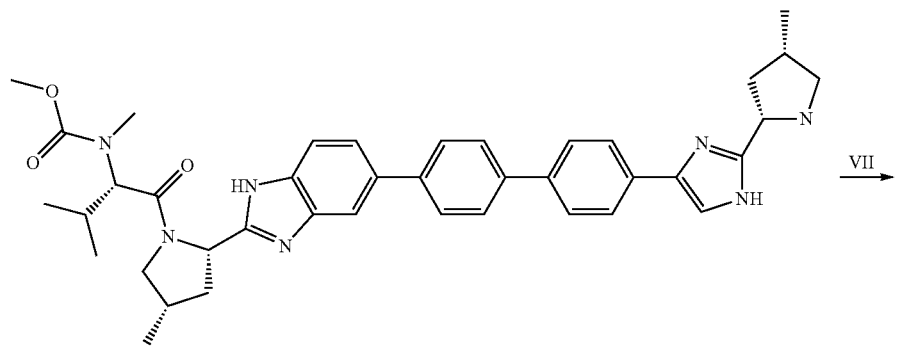 VII →

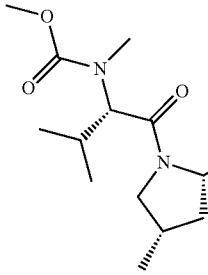

Step I

2-Bromo-1-[4-(4-bromophenyl)phenyl]ethanone

To a solution of 1-[4-(4-bromophenyl)phenyl]ethanone (5 g, 18.17 mmol) in CH$_2$Cl$_2$ (40 mL) is added bromine (983 µL, 19 mmol). The resulting mixture is stirred for 48 hours at room temperature. The mixture is diluted with dichloromethane, washed with saturated aqueous sodium bicarbonate, water, brine, dried over anhydrous sodium sulfate and concentrated. The crude solid is triturated with ether to give 2-bromo-1-[4-(4-bromophenyl)phenyl]ethanone (5.7 g, 88.6%) as a white solid.

Step II

(2S,4S)-2-(2-(4'-Bromobiphenyl-4-yl)-2-oxoethyl)1-tert-butyl 4-methylpyrrolidine-1,2-dicarboxylate To a solution of (2S,4S)-1-tert-butoxycarbonyl-4-methyl-pyrrolidine-2-carboxylic acid (437 mg, 1.905 mmol) in acetonitrile (6 mL) is added 2-bromo-1-[4-(4-bromophenyl)phenyl]ethanone (693 mg, 1.732 mmol) and DIPEA (0.332 mL, 1.905 mmol). The reaction mixture is stirred at room temperature for 4 hours and diluted with EtOAc and washed with brine (3×2 mL). The organic layer is concentrated to dryness, azeotroped with toluene (5 mL), and purified by flash column chromatography on silica gel (6 to 50% EtOAc in hexanes) to give (2S,4S)-2-(2-(4'-bromobiphenyl-4-yl)-2-oxoethyl)1-tert-butyl 4-methylpyrrolidine-1,2-dicarboxylate (870 mg, 1.732 mmol).

Step III

(2S,4S)-2-[4-(4'-Bromo-biphenyl-4-yl)-1H-imidazol-2-yl]-4-methyl-pyrrolidine-1-carboxylic acid tert-butyl ester To a solution of (2S,4S)-2-(2-(4'-bromobiphenyl-4-yl)-2-oxoethyl)1-tert-butyl 4-methylpyrrolidine-1,2-dicarboxylate (870 mg, 1.732 mmol) in toluene (8.7 mL) is added ammonium acetate (2.670 g, 34.64 mmol). The reaction mixture is stirred at 100° C. for 21 hours then cooled to rt and diluted with water (8.7 mL). The layers are separated and the aqueous layer is extracted with EtOAc (10 mL), and the combined organic layers are dried over Na$_2$SO$_4$, filtered, and concentrated to dryness. The residue is purified by flash column chromatography on silica gel (6 to 50% EtOAc in hexanes) to give (2S,4S)-2-[4-(4'-bromo-biphenyl-4-yl)-1H-imidazol-2-yl]-4-methyl-pyrrolidine-1-carboxylic acid tert-butyl ester (727 mg, 87% overall from step II).

$^1$H NMR (300 MHz, CDCl$_3$) δ 10.72 (s, 1H), 7.81 (s, 1H), 7.50 (dd, 6H), 7.26 (s, 1H), 4.93 (s, 1H), 3.77 (s, 1H), 2.86 (s, 1H), 2.60 (d, 2H), 2.26 (d, 1H), 1.48 (s, 9H), 1.11 (d, 3H).

LC/MS: m/z=481.97 (M+H$^+$).

Step IV

(2S,4S)-4-Methyl-2-{4-[4'-(4,4,5,5-tetramethyl-[1,3,2]dioxaborolan-2-yl)-biphenyl-4-yl]-1H-imidazol-2-yl}-pyrrolidine-1-carboxylic acid tert-butyl ester A solution of (2S,4S)-2-[4-(4'-bromo-biphenyl-4-yl)-1H-imidazol-2-yl]-4-methyl-pyrrolidine-1-carboxylic acid tert-butyl ester (725 mg, 1.503 mmol), 4,4,5,5-tetramethyl-2-(4,4,5,5-tetramethyl-1,3,2-dioxaborolan-2-yl)-1,3,2-dioxaborolane (1.145 g, 4.509 mmol), Pd(DPPF)(Cl)$_2$.CH$_2$Cl$_2$ (122.7 mg, 0.1503 mmol) and KOAc (737.5 mg, 7.515 mmol) in DMF (7.3 mL) is heated at 80° C. for 16 hours under nitrogen atmosphere. It is then cooled to RT and filtered over a bed of celite. The filtrate is diluted with water (15 mL) and the mixture is extracted with EtOAc (75 mL). The organic layer is washed with H$_2$O (3×15 mL) and concentrated to dryness. The residue is diluted with xylene (10 mL), evaporated to dryness and purified by flash column chromatography on silica gel (6 to 50% EtOAc in hexane) to give (2S,4S)-4-methyl-2-{4-[4'-(4,4,5,5-tetramethyl-[1,3,2]dioxaborolan-2-yl)-biphenyl-4-yl]-1H-imidazol-2-yl}-pyrrolidine-1-carboxylic acid tert-butyl ester (530 mg, 67%).

$^1$H NMR (300 MHz, CDCl3) δ 10.75 (br s, 1H), 8.00-7.49 (m, 8H), 7.30 (s, 1H), 4.98 (t, 1H), 3.88-3.71 (m, 1H), 2.90 (t, 1H), 2.77-2.42 (m, 2H), 2.29 (d, 1H), 1.56 (d, 9H), 1.38 (s, 12H), 1.15 (d, 3H).

Step V

(2S,4S)-2-{4-[4'-(2-[(2S,4S)-1-[(S)-2-(Methoxycarbonyl-methyl-amino)-3-methyl-butyryl]-4-methyl-pyrrolidin-2-yl}-1H-benzoimidazol-5-yl)-biphenyl-4-yl]-1H-imidazol-2-yl]-4-methyl-pyrrolidine-1-carboxylic acid tert-butyl ester To a suspension of (2S,4S)-4-methyl-2{-4-[4'-(4,4,5,5-tetramethyl-[1,3,2]dioxaborolan-2-yl)-biphenyl-4-yl]-1H-imidazol-2-yl}-pyrrolidine-1-carboxylic acid tert-butyl ester (211 mg, 0.3985 mmol), methyl N-[1-[(2S,4S)-2-(5-iodo-1H-benzimidazol-2-yl)-4-methyl-pyrrolidine-1-carbonyl]-2-methyl-propyl]-N-methyl-carbamate (198.6 mg, 0.3985 mmol), Pd(DPPF)(Cl)$_2$.CH$_2$Cl$_2$ (32.54 mg, 0.03985 mmol) in 2-propnaol (2.1 mL) is added 1M aqueous NaHCO$_3$ (2 mL, 2 mmol). The reaction mixture is stirred at 80° C. for 18 hours, cooled to RT, filtered on a bed of Celite and concentrated to dryness. The residue is purified by flash column chromatography on silica gel (12 to 100% EtOAc in hexanes) to give 2S,4S)-2-{4-[4'-(2-{(2S,4S)-1-[(S)-2-(methoxycarbonyl-methyl-amino)-3-methyl-butyryl]-4-methyl-pyrrolidin-2-yl}-1H-benzoimidazol-5-yl)-biphenyl-4-yl]-1H-imidazol-2-yl}-4-methyl-pyrrolidine-1-carboxylic acid tert-butyl ester (115 mg, 37%).

LC/MS: m/z=774.55 (M+H⁺).

Step VI

Methyl-{(S)-2-methyl-1-[(2S,4S)-4-methyl-2-(5-{4'-[2-((2S,4S)-4-methyl-pyrrolidin-2-yl)-1H-imidazol-4-yl]-biphenyl-4-yl}-1H-benzoimidazol-2-yl)-pyrrolidine-1-carbonyl]-propyl}-carbamic acid methyl ester hydrochloride To a solution of (2S,4S)-2-{4-[4'-(2-{(2S,4S)-1-[(S)-2-(methoxycarbonyl-methyl-amino)-3-methyl-butyryl]-4-methyl-pyrrolidin-2-yl}-1H-benzoimidazol-5-yl)-biphenyl-4-yl]-1H-imidazol-2-yl}-4-methyl-pyrrolidine-1-carboxylic acid tert-butyl ester (115 mg, 0.1486 mmol) in methanol is added 4M HCl in dioxane (0.632 mL, 2.526 mmol). The reaction mixture is stirred at room temperature for 1 hour and concentrated to dryness. The title product is used as such in the next step.

Step VII ((S)-1-{(2S,4S)-2-[5-(4'-{2-[(2S,4S)-1-((S)-2-Methoxycarbonylamino-3-methyl-butyryl)-4-methyl-pyrrolidin-2-yl]-1H-imidazol-4-yl}-biphenyl-4-yl)-1H-benzoimidazol-2-yl]-4-methyl-pyrrolidine-1-carbonyl}-2-methyl-propyl)-methyl-carbamic acid methyl ester To a solution of methyl-{(S)-2-methyl-1-[(2S,4S)-4-methyl-2-(5-{4'-[2-((2S,4S)-4-methyl-pyrrolidin-2-yl)-1H-imidazol-4-yl]-biphenyl-4-yl}-1H-benzoimidazol-2-yl)-pyrrolidine-1-carbonyl]-propyl}-carbamic acid methyl ester hydrochloride (50.2 mg, 0.707 mmol) in DMF (2 mL) cooled in an ice bath is sequentially added HATU (28.3 mg, 0.0744 mmol) and DIPEA (0.037 mL, 0.212 mmol) under nitrogen atmosphere. The reaction mixture is stirred at room temperature for 17 hours and diluted with saturated aqueous NaHCO₃ (2 mL). The mixture is extracted with EtOAc (5×3 mL), and the combined organic layers are washed with H₂O (3×3 mL), dried over Na₂SO₄, filtered, and concentrated to dryness. The residue is purified by preparative HPLC to give ((S)-1-{(2S,4S)-2-[5-(4'-{2-[(2S,4S)-1-((S)-2-methoxycarbonylamino-3-methyl-butyryl)-4-methyl-pyrrolidin-2-yl]-1H-imidazol-4-yl}-biphenyl-4-yl)-1H-benzoimidazol-2-yl]-4-methyl-pyrrolidine-1-carbonyl}-2-methyl-propyl)-methyl-carbamic acid methyl ester (29.1 mg, 47%).

¹H NMR (400 MHz, dmso-d6) δ 8.13 (s, 1H), 7.86 (m, 11H), 7.25 (d, 1H, J=7.9 Hz), 5.14 (m, 1H), 5.06 (m, 1H), 4.38 (m, 1H), 4.08 (m, 3H), 3.66 (m, 3H), 3.51 (s, 3H), 3.35 (m, 2H), 2.72 (m, 3H), 2.45 (m, 4H), 1.95 (m, 4H), 1.11 (m, 6H), 0.79 (d, 3H, J=6.7 Hz), 0.73 (m, 9H).

LC/MS: m/z=831.67 (M+H⁺).

Example 2

Methyl N-[(1S)-1-[(2S,4S)-2-[4-[4-[4-[2-[(2S,4S)-1-[(2S)-2-[methoxycarbonyl(methyl)amino]-3-methyl-butanoyl]-4-methyl-pyrrolidin-2-yl]-1H-benzimidazol-5-yl]phenyl]phenyl]-1H-imidazol-2-yl]-4-methyl-pyrrolidine-1-carbonyl]-2-methyl-propyl]-N-methyl-carbamate (Compound 6)

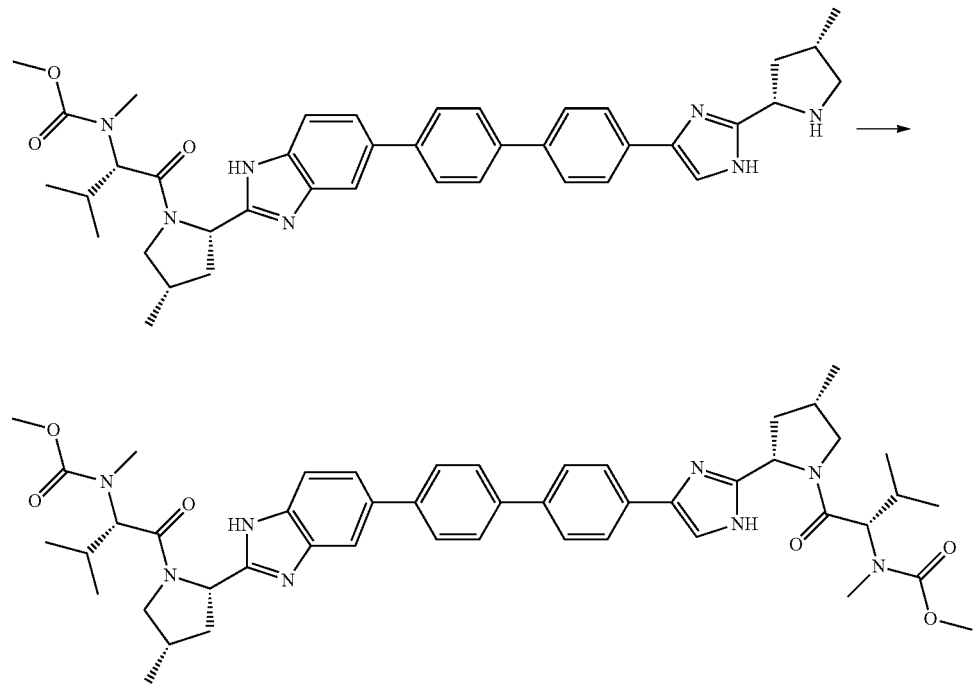

To a solution of (2S)-2-[methoxycarbonyl(methyl)amino]-3-methyl-butanoic acid (12.8 mg, 0.06765 mmol) and methyl methyl((S)-3-methyl-1-((2S,4S)-4-methyl-2-(6-(4'-(2-((2S,4S)-4-methylpyrrolidin-2-yl)-1H-imidazol-5-yl)[1,1'-biphenyl]-4-yl)-1H-benzo[d]imidazol-2-yl)pyrrolidin-1-yl)-1-oxobutan-2-yl)carbamate hydrochloride (48.1 mg, 0.0677 mmol) in DMF (2 mL) cooled in an ice bath is sequentially added HATU (28.3 mg, 0.0744 mmol) and DIPEA (0.035 mL, 0.203 mmol) under nitrogen atmosphere. The reaction mixture is stirred at room temperature for 19 hours and diluted with saturated aqueous NaHCO₃ (2 mL). The mixture is extracted with EtOAc (5×3 mL), and the combined organic layers are washed with H₂O (3×3 mL), dried over Na₂SO₄, filtered, and concentrated to dryness. The residue is purified by reverse phase preparative HPLC to give methyl N-[(1S)-1-[(2S,4S)-2-[4-[4-[4-[2-[(2S,4S)-1-[(2S)-2-[methoxycarbonyl(methyl)amino]-3-methyl-butanoyl]-4-methyl-pyrrolidin-2-yl]-1H-benzimidazol-5-yl]phenyl]phenyl]-1H-imidazol-2-yl]-4-methyl-pyrrolidine-1-carbonyl]-2-methyl-propyl]-N-methyl-carbamate (24.4 mg, 41%).

¹H NMR (400 MHz, dmso-d6) δ 7.84 (m, 12H), 5.06 (m, 2H), 4.45 (t, 2H), 4.28 (m, 1H), 4.14 (m, 1H), 4.07 (m, 1H), 3.64 (s, 6H), 3.36 (m, 2H), 2.73 (m, 6H), 2.43 (m, 4H), 1.96 (m, 2H), 1.87 (m, 2H), 1.11 (m, 6H), 0.74 (m, 12H).

LC/MS: m/z=845.57 (M+H⁺).

Example 3

Methyl ((S)-1-((2S,4S)-2-(4-(4'-(2-((2S,4S)-1-((S)-2-((methoxycarbonyl)amino)-3-methylbutanoyl)-4-methylpyrrolidin-2-yl)-3H-benzo[d]imidazol-6-yl)-[1,1'-biphenyl]-4-yl)-1H-imidazol-2-yl)-4-methylpyrrolidin-1-yl)-3-methyl-1-oxobutan-2-yl)(methyl)carbamate (Compound 8)

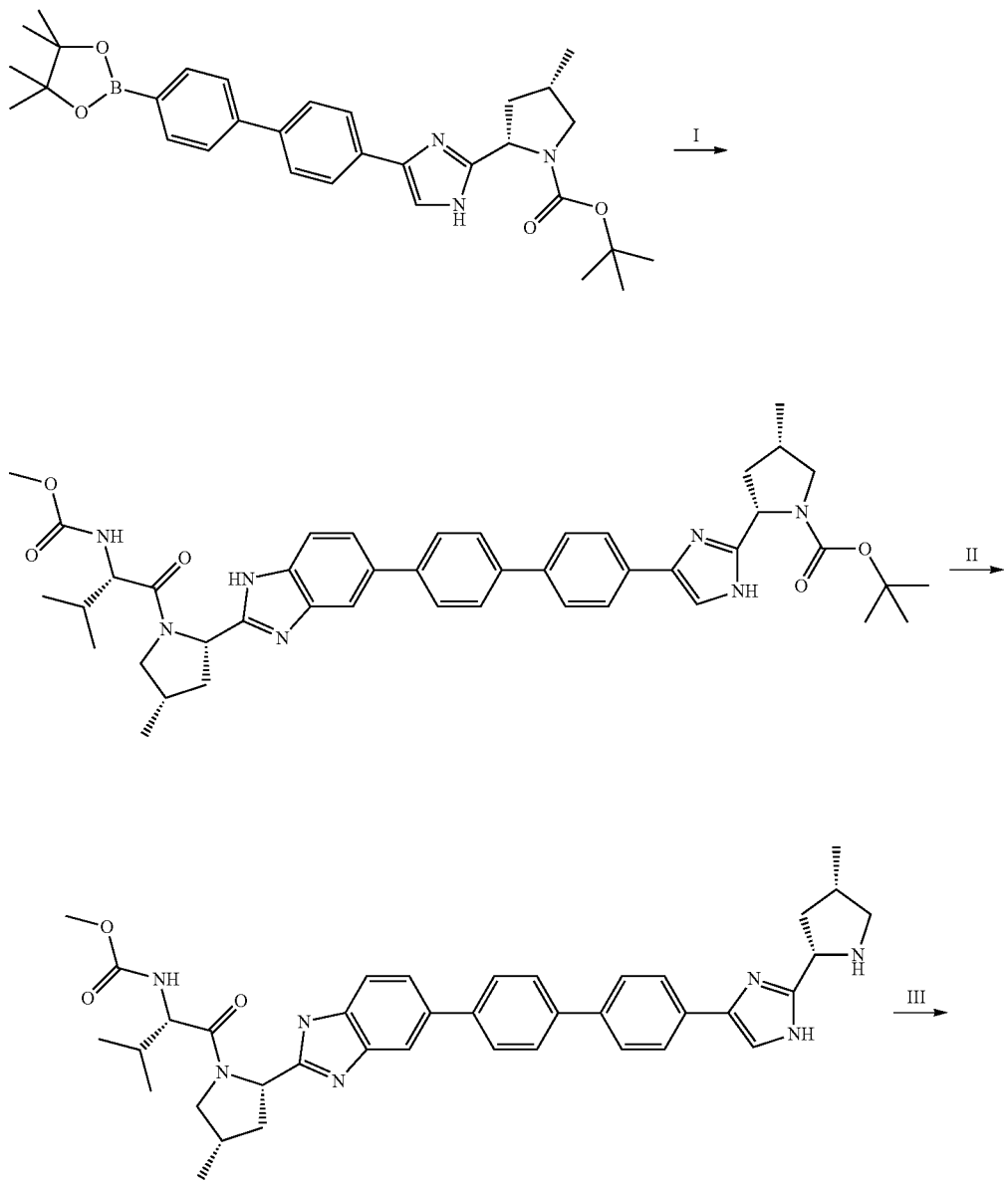

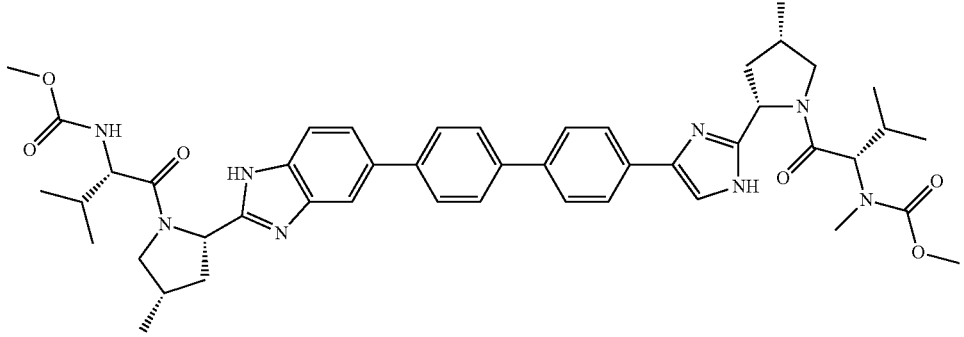

Step I

(2S,4S)-2-[4-(4'-{2-[(2S,4S)-1-((S)-2-Methoxycarbonylamino-3-methyl-butyryl)-4-methyl-pyrrolidin-2-yl]-1H-benzoimidazol-5-yl}-biphenyl-4-yl)-1H-imidazol-2-yl]-4-methyl-pyrrolidine-1-carboxylic acid tert-butyl ester To a suspension of (2S,4S)-4-methyl-2-{4-[4'-(4,4,5,5-tetramethyl-[1,3,2]dioxaborolan-2-yl)-biphenyl-4-yl]-1H-imidazol-2-yl}-pyrrolidine-1-carboxylic acid tert-butyl ester (138 mg, 0.2606 mmol), methyl ((S)-1-((2S,4S)-2-(5-iodo-1H-benzo[d]imidazol-2-yl)-4-methylpyrrolidin-1-yl)-3-methyl-1-oxobutan-2-yl)carbamate (126.2 mg, 0.2606 mmol), Pd(DPPF)(Cl)$_2$·CH$_2$Cl$_2$ (21.3 mg, 0.02606 mmol) in 2-propanol (1.4 mL) is added 1M aqueous NaHCO$_3$ (1.3 mL, 1.3 mmol). The reaction mixture is heated at 80° C. for 19 hours, cooled to RT, and extracted with dichloromethane (2×10 mL). The organic layer is dried over Na$_2$SO$_4$, filtered, and concentrated to dryness. The residue is purified by flash column chromatography on silica gel (50 to 100% EtOAc in hexanes) to give (2S,4S)-2-[4-(4'-{2-[(2S,4S)-1-((S)-2-methoxycarbonylamino-3-methyl-butyryl)-4-methyl-pyrrolidin-2-yl]-1H-benzoimidazol-5-yl}-biphenyl-4-yl)-1H-imidazol-2-yl]-4-methyl-pyrrolidine-1-carboxylic acid tert-butyl ester (75 mg, 38%). HPLC: Waters symmetry shield RP18 3.5 μm 4.6 mm×50 mm, solvent A: 0.01% TFA in acetonitrile, solvent B: 0.01% TFA in water, gradient: 15:85 A:B to 90:10 A:B over 10 minutes, RT=4.87 min.

Step II

{(S)-2-Methyl-1-[(2S,4S)-4-methyl-2-(5-{4'-[2-((2S,4S)-4-methyl-pyrrolidin-2-yl)-1H-imidazol-4-yl]-biphenyl-4-yl}-1H-benzoimidazol-2-yl)-pyrrolidine-1-carbonyl]-propyl}-carbamic acid methyl ester hydrochloride (2S,4S)-2-[4-(4'-{2-[(2S,4S)-1-((S)-2-Methoxycarbonylamino-3-methyl-butyryl)-4-methyl-pyrrolidin-2-yl]-1H-benzoimidazol-5-yl}-biphenyl-4-yl)-1H-imidazol-2-yl]-4-methyl-pyrrolidine-1-carboxylic acid tert-butyl ester (75 mg, 0.0987 mmol) is stirred with 4M HCl in dioxane (4 mL, 16 mmol). The reaction mixture is stirred at room temperature for 0.5 hour and concentrated to dryness. The product {(S)-2-methyl-1-[(2S,4S)-4-methyl-2-(5-{4'-[2-((2S,4S)-4-methyl-pyrrolidin-2-yl)-1H-imidazol-4-yl]-biphenyl-4-yl}-1H-benzoimidazol-2-yl)-pyrrolidine-1-carbonyl]-propyl}-carbamic acid methyl ester hydrochloride is used as such in the next step.

Step III

Methyl ((S)-1-((2S,4S)-2-(4-(4'-(2-((2S,4S)-1-((S)-2-((methoxycarbonyl)amino)-3-methylbutanoyl)-4-methylpyrrolidin-2-yl)-3H-benzo[d]imidazol-6-yl)-[1,1'-biphenyl]-4-yl)-1H-imidazol-2-yl)-4-methylpyrrolidin-1-yl)-3-methyl-1-oxobutan-2-yl)(methyl)carbamate To a solution of methyl {(S)-2-methyl-1-[(2S,4S)-4-methyl-2-(5-{4'-[2-((2S,4S)-4-methyl-pyrrolidin-2-yl)-1H-imidazol-4-yl]-biphenyl-4-yl}-1H-benzoimidazol-2-yl)-pyrrolidine-1-carbonyl]-propyl}-carbamic acid methyl ester hydrochloride (68.7 mg, 0.0987 mmol) and (2S)-2-[methoxycarbonyl(methyl)amino]-3-methyl-butanoic acid (18.67 mg, 0.09867 mmol) in DMF (2 mL), cooled in an ice bath is sequentially added HATU (41.25 mg, 0.1085 mmol) and DIPEA (38.26 mg, 51.56 μL, 0.2960 mmol) under nitrogen atmosphere. The reaction mixture is stirred at room temperature for 5 hours, and diluted with water (6 mL). The mixture is extracted with EtOAc (5×6 mL), and the combined organic layers are washed with H$_2$O (3×3 mL), dried over Na$_2$SO$_4$, filtered, and concentrated to dryness. The residue is purified by flash column chromatography on silica gel (0 to 10% methanol in CH$_2$Cl$_2$) and is further purified by reverse phase preparative HPLC to give methyl ((S)-1-((2S,4S)-2-(4-(4'-(2-((2S,4S)-1-((S)-2-((methoxycarbonyl)amino)-3-methylbutanoyl)-4-methylpyrrolidin-2-yl)-3H-benzo[d]imidazol-6-yl)-[1,1'-biphenyl]-4-yl)-1H-imidazol-2-yl)-4-methylpyrrolidin-1-yl)-3-methyl-1-oxobutan-2-yl)(methyl)carbamate (36 mg, 41%).

$^1$H NMR (400 MHz, dmso-d6) δ 8.13 (s, 1H), 7.88 (m, 11H), 7.25 (d, 1H, J=8.3 Hz), 5.14 (m, 1H), 5.08 (m, 1H), 4.37 (m, 1H), 4.13 (m, 2H), 3.64 (s, 3H), 3.51 (s, 3H), 3.40 (m, 3H), 2.72 (s, 3H), 2.48 (m, 4H), 1.93 (m, 4H), 1.11 (m, 6H), 0.76 (m, 12H).

LC/MS: m/z=831.61 (M+H$^+$).

Example 4

((S)-1-{(2S,4S)-2-[5-(4'-{2-[(2S,4S)-1-((S)-2-Methoxycarbonylamino-3-methyl-butyryl)-4-methyl-pyrrolidin-2-yl]-1H-imidazol-4-yl}-biphenyl-4-yl)-1H-benzoimidazol-2-yl]-4-methyl-pyrrolidine-1-carbonyl}-2-methyl-propyl)-carbamic acid methyl ester (Compound 5)

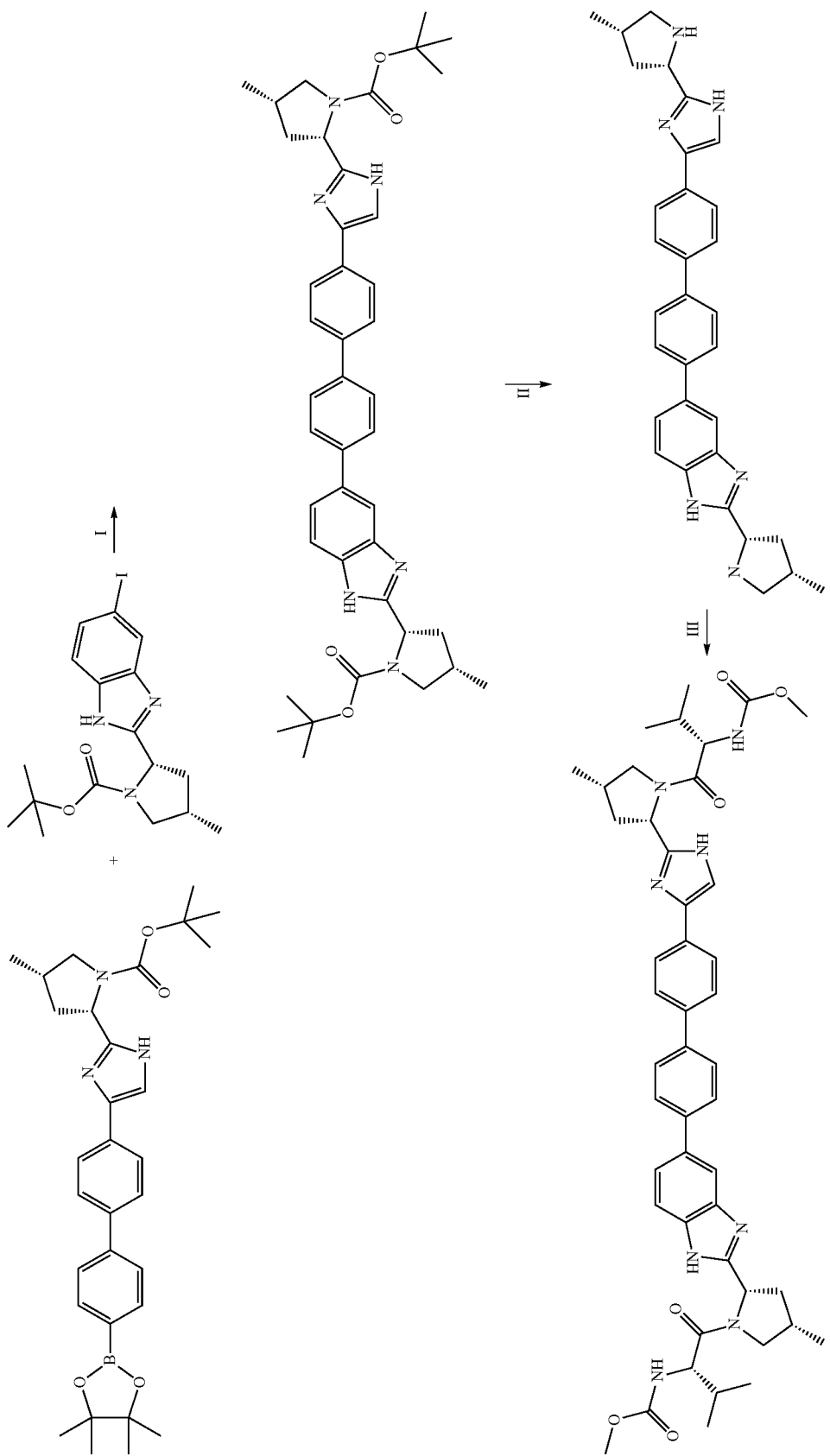

Step I (2S,4S)-tert-Butyl 2-(6-(4'-(2-((2S,4S)-1-(tert-butoxycarbonyl)-4-methylpyrrolidin-2-yl)-1H-imidazol-4-yl)-[1,1'-biphenyl]-4-yl)-3H-benzo[d]imidazol-2-yl)-4-methylpyrrolidine-1-carboxylate A solution of tert-butyl (2S,4S)-2-(5-iodo-1H-benzimidazol-2-yl)-4-methyl-pyrrolidine-1-carboxylate (2.0 g, 4.681 mmol), tert-butyl (2S,4S)-4-methyl-2-[4-[4-[4-(4,4,5,5-tetramethyl-1,3,2-dioxaborolan-2-yl)phenyl]phenyl]-1H-imidazol-2-yl]pyrrolidine-1-carboxylate (2.478 g, 4.681 mmol), and [3-(2-dicyclohexylphosphanylphenyl)-2,4-dimethoxyphenyl]sulfonyloxysodium (VPHOS) (183.7 mg, 0.3745 mmol) is prepared in isopropanol (31.2 mL)/NaHCO$_3$ (23.4 mL of 1 M in H$_2$O, 23.40 mmol) and then degassed under a stream of N$_2$ for 15 min. After diacetoxypalladium (21.02 mg, 0.09362 mmol) is added, the solution is heated to 100° C. under a reflux condenser for 8 hours. The reaction mixture is cooled to room temperature and then diluted with EtOAc (10 mL). The phases are separated and the aqueous layer is extracted with EtOAc (2×10 mL). The combined organic phases are dried over Na$_2$SO$_4$, filtered, and concentrated. The crude residue is purified by silica column (50-100% EtOAc/hexanes to afford (2S,4S)-tert-butyl 2-(6-(4'-(2-((2S,4S)-1-(tert-butoxycarbonyl)-4-methylpyrrolidin-2-yl)-1H-imidazol-4-yl)-[1,1'-biphenyl]-4-yl)-3H-benzo[d]imidazol-2-yl)-4-methylpyrrolidine-1-carboxylate (2.55 g), R$_f$=0.3 (EtOAc).

$^1$H NMR (300 MHz, Acetone-d6) δ 11.40 (s, 1H), 11.09 (s, 1H), 8.00-7.41 (m, 12H), 5.05 (s, 1H), 4.90 (s, 1H), 3.86 (s, 2H), 2.99 (d, 2H), 2.39 (ddt, 5H), 1.90-1.75 (m, 1H), 1.45 (s, 9H), 1.29-1.16 (m, 9H), 1.11 (d, 6H).
LC/MS: m/z=703.62 (M+H$^+$).

Step II 2-((2S,4S)-4-Methylpyrrolidin-2-yl)-6-(4'-(2-((2S,4S)-4-methylpyrrolidin-2-yl)-1H-imidazol-4-yl)-[1,1'-biphenyl]-4-yl)-3H-benzo[d]imidazole In a 100 mL flask, (2S,4S)-tert-butyl 2-(6-(4'-(2-((2S,4S)-1-(tert-butoxycarbonyl)-4-methylpyrrolidin-2-yl)-1H-imidazol-4-yl)-[1,1'-biphenyl]-4-yl)-3H-benzo[d]imidazol-2-yl)-4-methylpyrrolidine-1-carboxylate (2.55 g, 3.628 mmol) is dissolved in CH$_2$Cl$_2$ (10 mL). The solution is cooled to 0° C. and HCl (18.14 mL of 2.0 M, 36.28 mmol) is added. The reaction mixture is then stirred vigorously for 30 min at rt. The solution is concentrated and then dried under high vacuum. The yellow salt (2.353 g) is used in the next reaction without further purification.

Step III ((S)-1-{(2S,4S)-2-[5-(4'-{2-[(2S,4S)-1-((S)-2-Methoxycarbonylamino-3-methyl-butyryl)-4-methyl-pyrrolidin-2-yl]-1H-imidazol-4-yl}-biphenyl-4-yl)-1H-benzoimidazol-2-yl]-4-methyl-pyrrolidine-1-carbonyl}-2-methyl-propyl)-carbamic acid methyl ester In a 100 mL round bottom flask, 2-((2S,4S)-4-methylpyrrolidin-2-yl)-6-(4'-(2-((2S,4S)-4-methylpyrrolidin-2-yl)-1H-imidazol-4-yl)-[1,1'-biphenyl]-4-yl)-3H-benzo[d]imidazole (2.353 g, 3.628 mmol), (2S)-2-(methoxycarbonylamino)-3-methyl-butanoic acid (1.589 g, 9.070 mmol), and HATU (4.966 g, 13.06 mmol) are combined in DMF (25.95 mL) and then cooled to 0° C. DIPEA (4.689 g, 6.319 mL, 36.28 mmol) is added and the reaction is stirred at rt for 8 hours. The reaction mixture is concentrated and the resulting residue is diluted with EtOAc (50 mL). The organics are washed with sat. aq. NaHCO$_3$ (20 mL) and water (20 mL). The aqueous layer is back-extracted with EtOAc (20 mL), washed with water (10 mL), and the combined organics are dried over Na$_2$SO$_4$, filtered, and concentrated. The crude residue is purified by silica chromatography (0-5% MeOH/EtOAc, R$_f$=0.5, 10% MeOH/CH$_2$Cl$_2$) to afford ((S)-1-{(2S,4S)-2-[5-(4'-{2-[(2S,4S)-1-((S)-2-methoxycarbonylamino-3-methyl-butyryl)-4-methyl-pyrrolidin-2-yl]-1H-imidazol-4-yl}-biphenyl-4-yl)-1H-benzoimidazol-2-yl]-4-methyl-pyrrolidine-1-carbonyl}-2-methyl-propyl)-carbamic acid methyl ester (905 mg, 30%) as a yellow solid.

$^1$H NMR (400 MHz, dmso-d6) δ 12.29 (m, 1H), 12.02 (m, 1H), 7.73 (m, 12H), 7.23 (m, 2H), 5.02 (m, 1H), 4.91 (m, 1H), 4.10 (m, 4H), 3.51 (br. s, 6H), 3.28 (m, 2H), 3.15 (d, 2H), 2.38 (m, 4H), 1.81 (m, 4H), 1.09 (m, 6H), 0.80 (m, 12H).
LC/MS: m/z=816.99 (M+H$^+$).

Example 4 (Alternative Route)

((S)-1-{(2S,4S)-2-[5-(4'-{2-[(2S,4S)-1-((S)-2-Methoxycarbonylamino-3-methyl-butyryl)-4-methyl-pyrrolidin-2-yl]-1H-imidazol-4-yl}-biphenyl-4-yl)-1H-benzoimidazol-2-yl]-4-methyl-pyrrolidine-1-carbonyl}-2-methyl-propyl)-carbamic acid methyl ester (Compound 5)

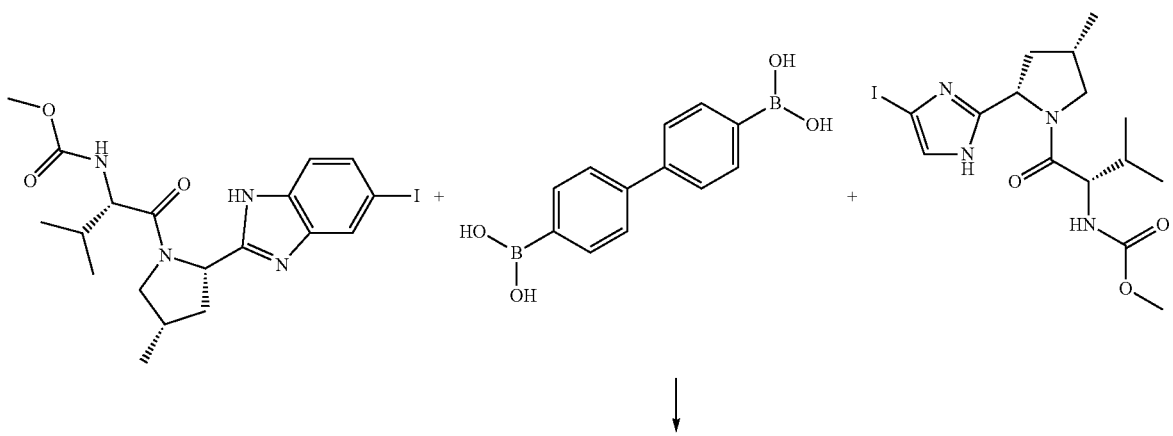

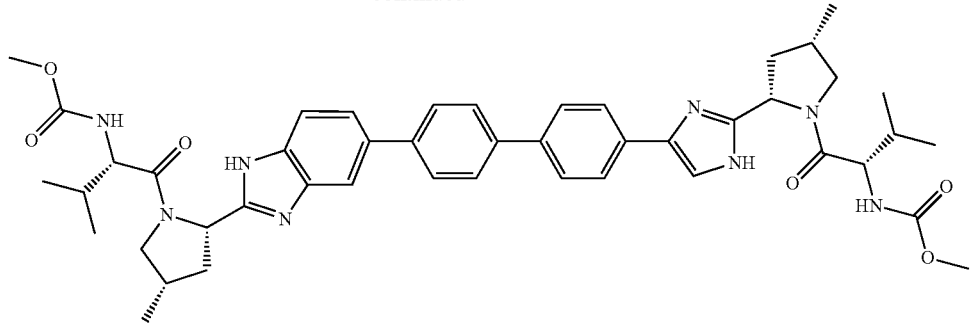

To a suspension of methyl N-[(1S)-1-[(2S,4S)-2-(5-iodo-1H-benzimidazol-2-yl)-4-methyl-pyrrolidine-1-carbonyl]-2-methyl-propyl]carbamate (52.40 mg, 0.1082 mmol), methyl ((S)-1-((2S,4S)-2-(4-iodo-1H-imidazol-2-yl)-4-methylpyrrolidin-1-yl)-3-methyl-1-oxobutan-2-yl)carbamate (47 mg, 0.1082 mmol), [1,1'-biphenyl]-4,4'-diyldiboronic acid (26.17 mg, 0.1082 mmol), Pd(DPPF)(Cl)$_2$·CH$_2$Cl$_2$ (4.418 mg, 0.005410 mmol) and 1 mL of 2-propanol in a microwave vial is added 1M aqueous NaHCO$_3$ (541.0 µL, 0.5410 mmol). The reaction mixture is stirred for 3 minutes at room temperature and is heated to 150° C. in the microwave for 10 minutes. The reaction mixture is concentrated to dryness. The residue is purified by flash column chromatography on silica gel (0 to 10% methanol in CH$_2$Cl$_2$) and is further purified by reverse phase preparative HPLC to give ((S)-1-{(2S,4S)-2-[5-(4'-{2-[(2S,4S)-1-((S)-2-methoxycarbonylamino-3-methyl-butyryl)-4-methyl-pyrrolidin-2-yl]-1H-imidazol-4-yl}-biphenyl-4-yl)-1H-benzoimidazol-2-yl]-4-methyl-pyrrolidine-1-carbonyl}-2-methyl-propyl)-carbamic acid methyl ester (12 mg, 25%).

LC/MS: m/z=817.62 (M+H$^+$).

Example 5

((S)-1-{(S)-2-[5-(4'-{2-[(S)-1-((S)-2-Methoxycarbonylamino-3-methyl-butyryl)-pyrrolidin-2-yl]-3H-benzoimidazol-5-yl}-biphenyl-4-yl)-1H-imidazol-2-yl]-pyrrolidine-1-carbonyl}-2-methyl-propyl)-carbamic acid methyl ester (Compound 4)

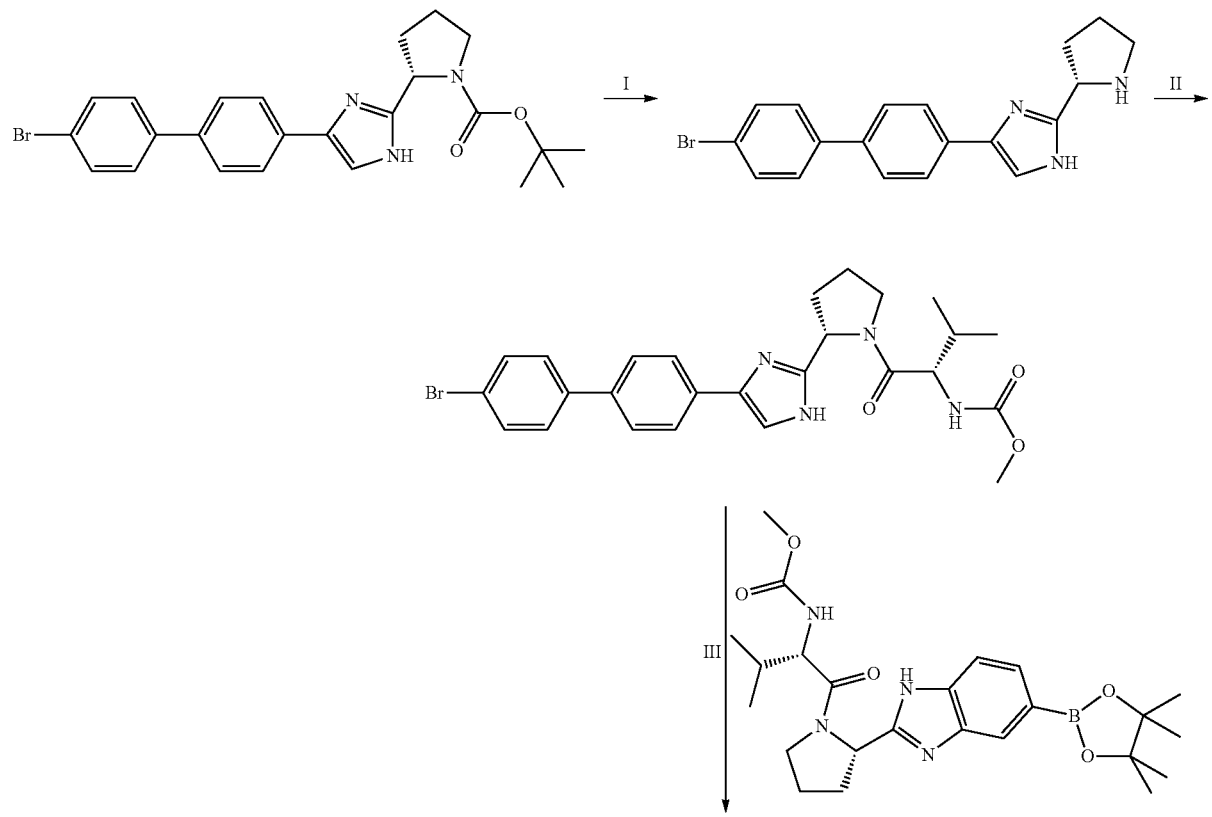

-continued

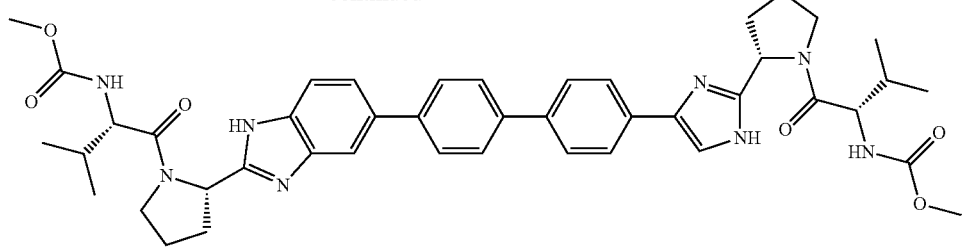

Step I

(S)-4-(4'-bromo-[1,1'-biphenyl]-4-yl)-2-(pyrrolidin-2-yl)-1H-imidazole

A suspension of (S)-tert-butyl 2-(4-(4'-bromo-[1,1'-biphenyl]-4-yl)-1H-imidazol-2-yl)pyrrolidine-1-carboxylate (505 mg, 1.078 mmol) in HCl (4M in dioxane 5.4 mL, 21.6 mmol) is stirred at room temperature for 2 hours and diluted with diethyl ether (2 mL). The suspension is cooled in an ice bath and the product is collected by filtration to give (S)-4-(4'-bromo-[1,1'-biphenyl]-4-yl)-2-(pyrrolidin-2-yl)-1H-imidazole hydrochloride (436 mg, 99%).

Step II

Methyl ((S)-1-((S)-2-(4-(4'-bromo-[1,1'-biphenyl]-4-yl)-1H-imidazol-2-yl)pyrrolidin-1-yl)-3-methyl-1-oxobutan-2-yl)carbamate To a solution of (S)-4-(4'-bromo-[1,1'-biphenyl]-4-yl)-2-(pyrrolidin-2-yl)-1H-imidazole hydrochloride (423 mg, 1.045 mmol) in DMF (5 mL) is sequentially added (2S)-2-(methoxycarbonylamino)-3-methyl-butanoic acid (201.5 mg, 1.150 mmol), DIPEA (405.2 mg, 546.1 μL, 3.135 mmol) and HATU (596.2 mg, 1.568 mmol) under nitrogen atmosphere. The reaction mixture is stirred at room temperature for 2 hours and diluted with saturated aqueous NaHCO₃ (10 mL). The reaction mixture is extracted with EtOAc (5×10 mL), and the combined organic layer are washed with H₂O (3×10 mL), and concentrated to dryness. The residue is purified by flash column chromatography on silica gel (2 to 20% methanol in CH₂Cl₂) to give methyl ((S)-1-((S)-2-(4-(4'-bromo-[1,1'-biphenyl]-4-yl)-1H-imidazol-2-yl)pyrrolidin-1-yl)-3-methyl-1-oxobutan-2-yl)carbamate (462 mg, 84%).

Step III

((S)-1-{(S)-2-[5-(4'-{2-[(S)-1-((S)-2-Methoxycarbonylamino-3-methyl-butyryl)-pyrrolidin-2-yl]-3H-benzoimidazol-5-yl}-biphenyl-4-yl)-1H-imidazol-2-yl]-pyrrolidine-1-carbonyl}-2-methyl-propyl)-carbamic acid methyl ester To a suspension of methyl ((S)-1-((S)-2-(4-(4'-bromo-[1,1'-biphenyl]-4-yl)-1H-imidazol-2-yl)pyrrolidin-1-yl)-3-methyl-1-oxobutan-2-yl)carbamate (99.6 mg, 0.1896 mmol), methyl ((S)-3-methyl-1-oxo-1-((S)-2-(6-(4,4,5,5-tetramethyl-1,3,2-dioxaborolan-2-yl)-3H-benzo[d]imidazol-2-yl)pyrrolidin-1-yl)butan-2-yl)carbamate and Pd(DPPF)(Cl)₂.CH₂Cl₂ (15.48 mg, 0.01896 mmol) in acetonitrile (2 mL) is added aqueous 1M NaHCO₃ (0.284 mL, 0.569 mmol). The reaction mixture is heated in a microwave oven at 130° C. for 10 minutes, cooled to rt, and diluted with water (10 mL). The reaction mixture is extracted by CH₂Cl₂ (5×10 mL), and the combined organic layers are dried over Na₂SO₄, filtered, and concentrated to dryness. The residue is purified by flash column chromatography on silica gel (2 to 20% methanol in CH₂Cl₂) and is further purified by reverse phase preparative HPLC to give ((S)-1-[(S)-2-[5-(4'-{2-[(S)-1-((S)-2-methoxycarbonylamino-3-methyl-butyryl)-pyrrolidin-2-yl]-3H-benzoimidazol-5-yl]-biphenyl-4-yl)-1H-imidazol-2-yl]-pyrrolidine-1-carbonyl}-2-methyl-propyl)-carbamic acid methyl ester (30 mg, 19%).

$^1$H NMR (400 MHz, dmso-d6) δ 8.13 (s, 1H), 7.89 (m, 11H), 7.32 (m, 2H), 5.25 (m, 1H), 5.15 (m, 1H), 4.11 (q, 2H, J=8.2 Hz), 3.93 (m, 2H), 3.85 (m, 2H), 3.52 (s, 6H), 2.42 (m, 2H), 2.16 (m, 4H), 2.04 (m, 4H), 0.82 (d, 6H, J=6.8 Hz), 0.76 (d, 6H, J=6.8 Hz).

Example 6

Methyl N-[(1S)-1-[(2S,4S)-2-[5-[4-[4-[2-[(2S,4S)-1-[(2S)-2-(methoxycarbonylamino)-3-methyl-butanoyl]-4-methyl-pyrrolidin-2-yl]-1H-benzimidazol-5-yl]phenyl]phenyl]-4-methyl-1H-imidazol-2-yl]-4-methyl-pyrrolidine-1-carbonyl]-2-methyl-propyl] carbamate (Compound 15)

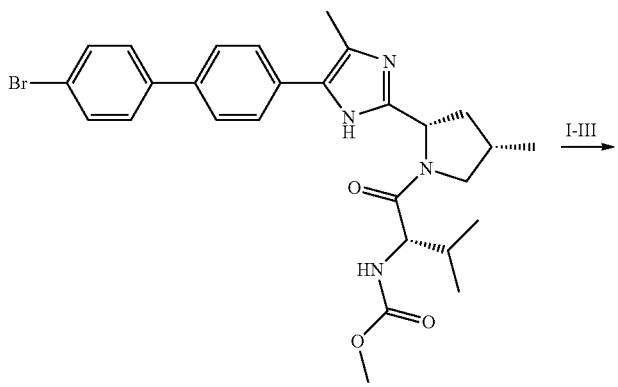

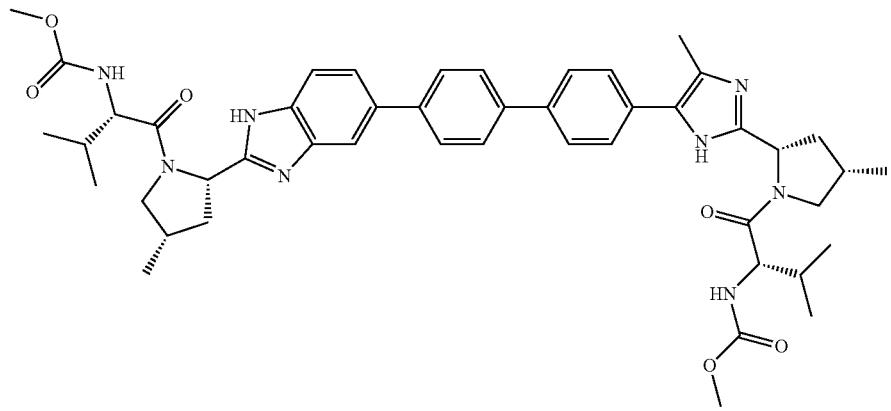

Procedure is same as described for ((S)-1-{(2S,4S)-2-[5-(4'-{2-[(2S,4S)-1-((S)-2-methoxycarbonylamino-3-methyl-butyryl)-4-methyl-pyrrolidin-2-yl]-1H-imidazol-4-yl}-biphenyl-4-yl)-1H-benzoimidazol-2-yl]-4-methyl-pyrrolidine-1-carbonyl}-2-methyl-propyl)-carbamic acid methyl ester, Example 4.

$^1$H NMR (400 MHz, CD$_3$OD) δ 7.97-7.70 (m, 11H), 7.69-7.62 (m, 2H), 5.35 (m, 1H), 5.13 (m, 1H), 4.35 (m, 2H), 4.10 (m, 2H), 3.64 (s, 6H), 3.45 (m, 2H), 2.67-2.40 (m, 4H), 2.40 (s, 3H), 2.05-1.80 (m, 4H), 1.37 (m, 6H), 0.95 (m 6H), 0.78 (m, 6H).

LC/MS: m/z=831.46 (M+H$^+$).

Intermediate (2S,4S)-tert-Butyl 2-(5-(4'-bromo-[1,1'-biphenyl]-4-yl)-4-methyl-1H-imidazol-2-yl)-4-methylpyrrolidine-1-carboxylate

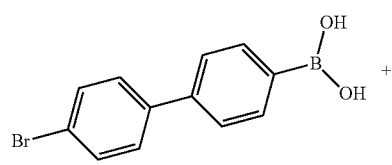 +

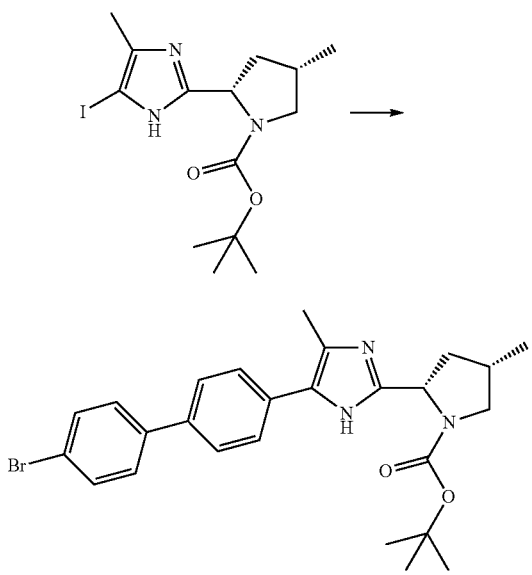

To a solution of tert-butyl (2S,4S)-2-(5-iodo-4-methyl-1H-imidazol-2-yl)-4-methyl-pyrrolidine-1-carboxylate (289 mg, 0.7387 mmol) in 6 mL of 5:1 toluene:methanol is sequentially added [4-(4-bromophenyl)phenyl]boronic acid (346.7 mg, 1.252 mmol), K$_3$PO$_4$ (199.3 mg, 0.9389 mmol) and Pd(PPh$_3$)$_4$ (71.85 mg, 0.06218 mmol). The reaction mixture is heated at 75° C. for 3 hours. The reaction mixture is concentrated, diluted with ethyl acetate, and washed with water and brine. The organic layer is concentrated to dryness. The residue is dissolved in dichloromethane and purified by flash column chromatography on silica gel (0-10% methanol/dichloromethane) to give (2S,4S)-tert-butyl 2-(5-(4'-bromo-[1,1'-biphenyl]-4-yl)-4-methyl-1H-imidazol-2-yl)-4-methylpyrrolidine-1-carboxylate (160 mg, 0.322 mmol).

LC-MS: m/z=497.91 (M+H$^+$).

Example 7

Methyl N-[(1S)-1-[(2S)-2-[4-[4-[2-[(2S)-1-[(2S)-2-(methoxycarbonylamino)-3-methyl-butanoyl]pyrrolidin-2-yl]-1H-benzimidazol-5-yl]phenyl]-1H-imidazol-2-yl]pyrrolidine-1-carbonyl]-2-methyl-propyl]carbamate (Compound 3)

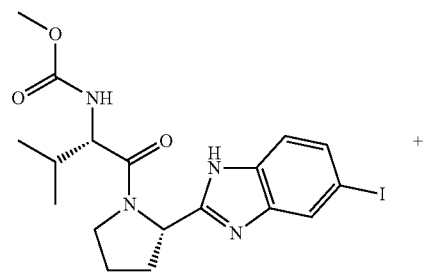

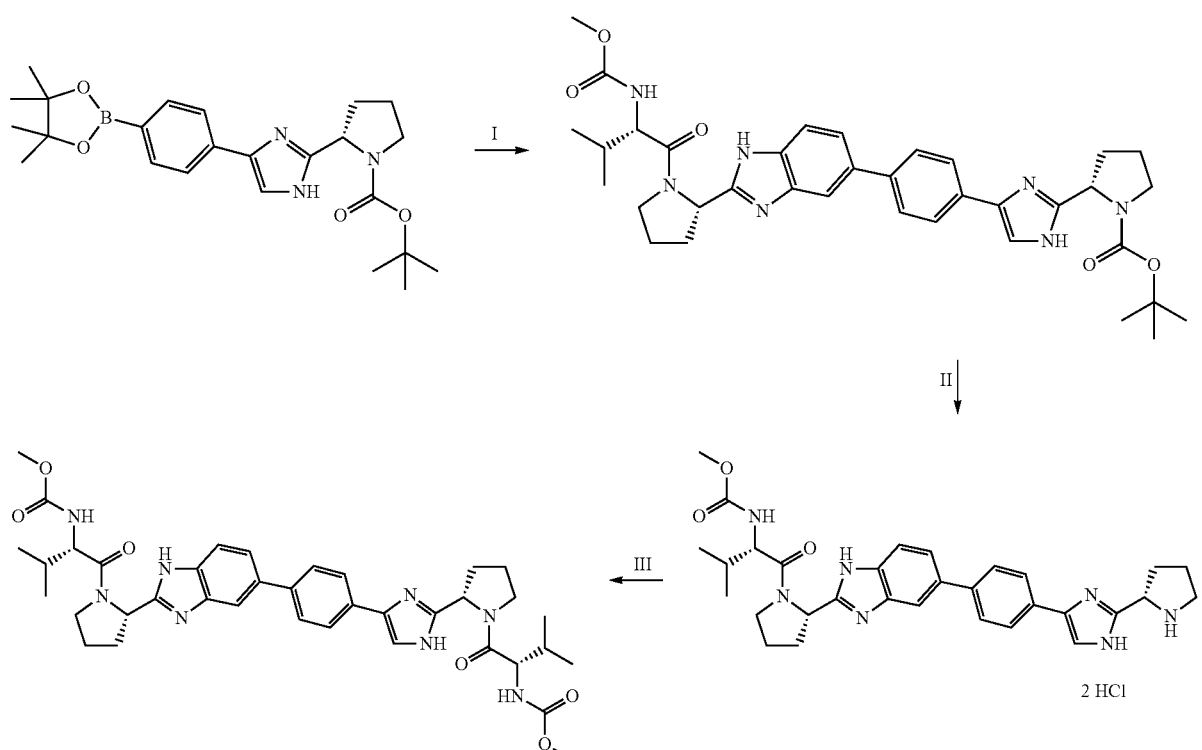

Step I tert-Butyl (2S)-2-[4-[4-[2-[(2S)-1-[(2S)-2-(methoxycarbonylamino)-3-methyl-butanoyl]pyrrolidin-2-yl]-1H-benzimidazol-5-yl]phenyl]-1H-imidazol-2-yl]pyrrolidine-1-carboxylate To a solution of tert-butyl (2S)-2-[4-[4-(4,4,5,5-tetramethyl-1,3,2-dioxaborolan-2-yl)phenyl]-1H-imidazol-2-yl]pyrrolidine-1-carboxylate (169 mg, 0.3847 mmol) (Ref. WO 2008/021923), methyl ((S)-1-((S)-2-(5-iodo-1H-benzo[d]imidazol-2-yl)pyrrolidin-1-yl)-3-methyl-1-oxobutan-2-yl)carbamate (180.9 mg, 0.3847 mmol) and Pd(dppf)Cl$_2$—CH$_2$Cl$_2$ (47.13 mg, 0.05771 mmol) in acetonitrile (4 mL) in a sealed tube (25 mL) under nitrogen atmosphere is added aq. sodium bicarbonate (961.8 µL of 1 M, 0.9618 mmol). The resultant suspension is heated in oil bath at 100° C. for 16 hours, concentrated, diluted with water and CH$_2$Cl$_2$, organic solution is separated, aqueous solution is extracted with dichloromethane, combined extracts are washed with brine and dried (Na$_2$SO$_4$). Purification of the residue on 25+M biotage silica gel cartridge using MeOH-ethyl acetate (0:100 to 15:85) as eluent afforded tert-butyl (2S)-2-[4-[4-[2-[(2S)-1-[(2S)-2-(methoxycarbonylamino)-3-methyl-butanoyl]pyrrolidin-2-yl]-1H-benzimidazol-5-yl]phenyl]-1H-imidazol-2-yl]pyrrolidine-1-carboxylate (101 mg, 0.1491 mmol, 38.75%) as light brown solid.

LC/MS: m/z=656.55 (M+H$^+$).

Step II 4-(4-(2-((S)-1-((S)-2-((Methoxycarbonyl)amino)-3-methylbutanoyl)pyrrolidin-2-yl)-1H-benzo[d]imidazol-5-yl)phenyl)-2-((S)-pyrrolidin-1-ium-2-yl)-1H-imidazol-3-ium chloride To a solution of tert-butyl (2S)-2-[4-[4-[2-[(2S)-1-[(2S)-2-(methoxycarbonylamino)-3-methyl-butanoyl]pyrrolidin-2-yl]-1H-benzimidazol-5-yl]phenyl]-1H-imidazol-2-yl]pyrrolidine-1-carboxylate (100 mg, 0.1525 mmol) in MeOH (0.15 mL) is added HCl in dioxane (381.2 µL of 4 M, 1.525 mmol), stirred at rt overnight, then concentrated to afford 4-(4-(2-((S)-1-((S)-2-((methoxycarbonyl)amino)-3-methylbutanoyl) pyrrolidin-2-yl]-1H-benzo[d]imidazol-5-yl)phenyl)-2-((S)-pyrrolidin-1-ium-2-yl)-1H-imidazol-3-ium chloride (100 mg, 0.1529 mmol, 100.3%) as a light brown solid. LC-MS shows presence of desired compound which is used as such in the next step without further purification.

LC/MS: m/z=556.33 (M+H$^+$).

Step III

Methyl N-[(1S)-1-[(2S)-2-[4-[4-[2-[(2S)-1-[(2S)-2-(methoxycarbonylamino)-3-methyl-butanoyl]pyrrolidin-2-yl]-1H-benzimidazol-5-yl]phenyl]-1H-imidazol-2-yl]pyrrolidine-1-carbonyl]-2-methyl-propyl] carbamate To a cold (0-4° C.) stirred light suspension of 4-(4-(2-((S)-1-((S)-2-((methoxycarbonyl)amino)-3-methylbutanoyl)pyrrolidin-2-yl]-1H-benzo[d]imidazol-5-yl)phenyl)-2-((S)-pyrrolidin-1-ium-2-yl)-1H-imidazol-3-ium chloride (98.09 mg, 0.15 mmol) and (2S)-2-(methoxycarbonylamino)-3-methyl-butanoic acid (28.91 mg, 0.1650 mmol) in DMF (1.5 mL) is sequentially added HATU (85.55 mg, 0.2250 mmol) and DIPEA (116.3 mg, 156.7 µL, 0.9000 mmol). The resulting mixture is slowly warmed up to rt, stirred overnight, then diluted with water (5 mL), extracted with ethyl acetate (3×6 mL). The combined extracts are washed with saturated bicarbonate solution, brine, dried (Na$_2$SO$_4$) and concentrated. Residue purified on 25+M biotage SiO$_2$ cartridge using MeOH-EtOAc (0:100, 15:85) as eluent to afford methyl N-[(1S)-1-[(2S)-2-[4-[4-[2-[(2S)-1-[(2S)-2-(methoxycarbonylamino)-3-methyl-butanoyl]pyrrolidin-2-yl]-1H-benzimidazol-5-yl]phenyl]-1H-imidazol-2-yl]pyrrolidine-1-carbonyl]-2-methyl-propyl]carbamate (45.8 mg, 0.06007 mmol, 37.45%) as white solid. This product is repurified by reverse phase HPLC to give methyl N-[(1S)-1-[(2S)-2-[4-[4-[2-[(2S)-1-[(2S)-2-(methoxycarbonylamino)-3-methyl-butanoyl]pyrrolidin-2-yl]-1H-benzimidazol-5-yl]phenyl]-1H-imidazol-2-yl]pyrrolidine-1-carbonyl]-2-methyl-propyl]carbamate (29.6 mg) as white solid.

$^1$H NMR (400 MHz, CD$_3$OD) δ 7.87-7.20 (m, 10H), 5.27 (dd, 1H), 5.17 (dd, 1H), 4.3-4.2 (m, 2H), 4.12-3.8 (m, 5H), 3.65 (s, 6H), 3.55-3.45 (m, 1H), 2.51-1.92 (m, 10H), 1.02-0.80 (doublets, 12H).

LC/MS: m/z=713.6 (M+H$^+$).

Example 8

Methyl N-[(1S)-1-[(2S,5S)-2-[4-[4-[2-[(2S,5S)-1-[2-(methoxycarbonylamino)-3-methyl-butanoyl]-5-methyl-pyrrolidin-2-yl]-1H-benzimidazol-5-yl]phenyl]phenyl]-1H-imidazol-2-yl]-5-methyl-pyrrolidine-1-carbonyl]-2-methyl-propyl]carbamate
(Compound 13)

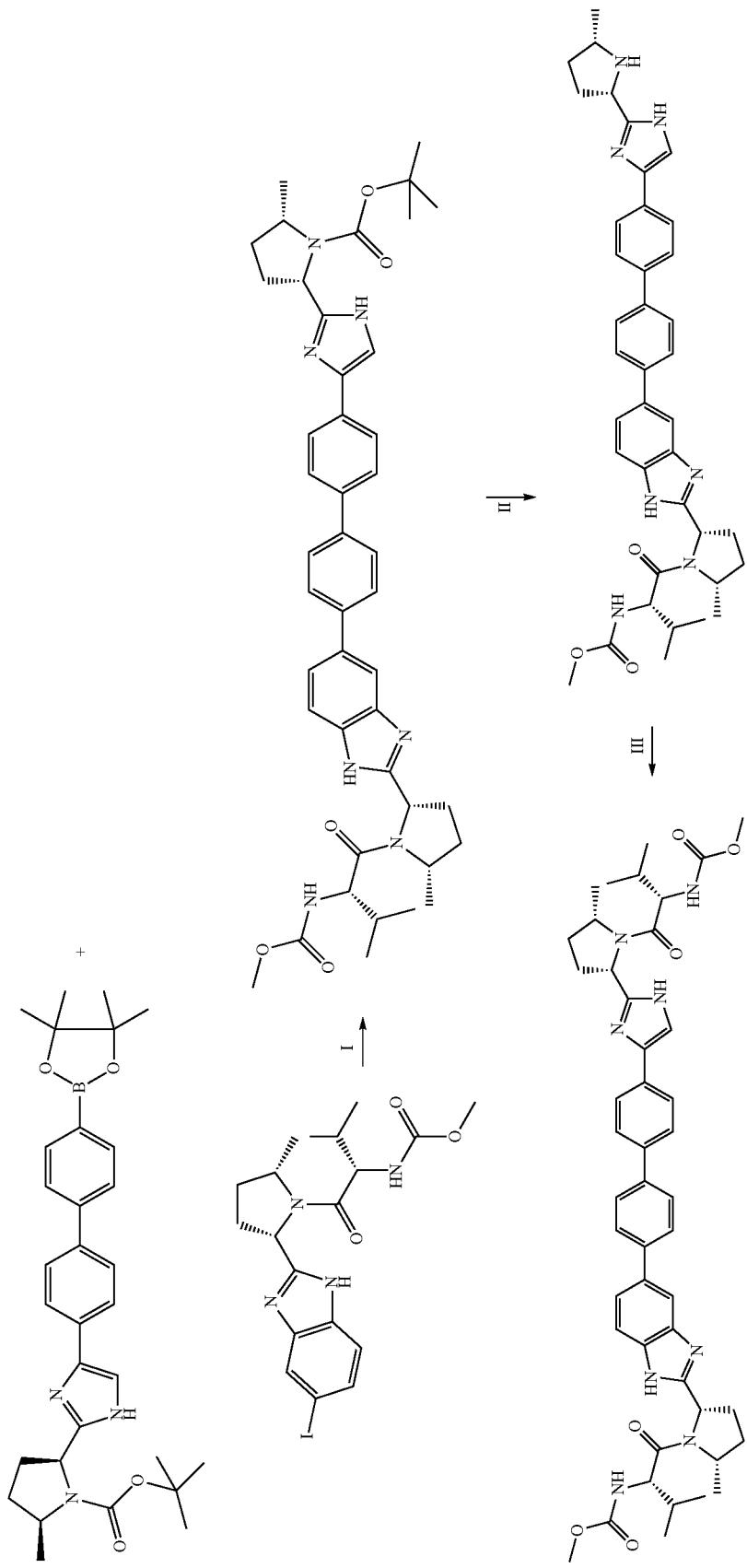

Step I tert-Butyl (2S,5S)-2-[4-[4-[4-[2-[(2S,5S)-1-[2-(methoxycarbonylamino)-3-methyl-butanoyl]-5-methyl-pyrrolidin-2-yl]-1H-benzimidazol-5-yl]phenyl]phenyl]-1H-imidazol-2-yl]-5-methyl-pyrrolidine-1-carboxylate To a mixture of tert-butyl (2S,5S)-2-methyl-5-[4-[4-[4-(4,4,5,5-tetramethyl-1,3,2-dioxaborolan-2-yl)phenyl]phenyl]-1H-imidazol-2-yl]pyrrolidine-1-carboxylate (180 mg, 0.34 mmol), methyl N-[(1S)-1-[(2S,5S)-2-(5-iodo-1H-benzimidazol-2-yl)-5-methyl-pyrrolidine-1-carbonyl]-2-methyl-propyl]carbamate (164.7 mg, 0.34 mmol), Pd(dppf)(Cl)$_2$.CH$_2$Cl$_2$ (27.77 mg, 0.034 mmol) in 2-propanol (2 ml) is added aq NaHCO$_3$ (1.7 mL of 1 M, 1.7 mmol). The reaction mixture is purged with N$_2$, heated at 80° C. overnight, diluted with EtOAc, washed with H$_2$O and brine. The organic phase is dried over Na$_2$SO$_4$, filtered and concentrated. The residue is purified by flash column chromatography on silica gel (1 to 30% MeOH in CH$_2$Cl$_2$) to afford the tert-butyl (2S,5S)-2-[4-[4-[4-[2-[(2S,5S)-1-[2-(methoxycarbonylamino)-3-methyl-butanoyl]-5-methyl-pyrrolidin-2-yl]-1H-benzimidazol-5-yl]phenyl]phenyl]-1H-imidazol-2-yl]-5-methyl-pyrrolidine-1-carboxylate (97 mg, 37.5%) as a beige solid.

LC/MS: m/z=760.5 (M+H$^+$).

Step II

Methyl N-[2-methyl-1-[(2S,5S)-2-methyl-5-[4-[4-[4-[2-[(2S,5S)-5-methylpyrrolidin-2-yl]-1H-imidazol-5-yl]phenyl]phenyl]-1H-benzimidazol-2-yl]pyrrolidine-1-carbonyl]propyl]-carbamate To a solution of tert-butyl (2S,5S)-2-[4-[4-[4-[2-[(2S,5S)-1-[2-(methoxycarbonylamino)-3-methyl-butanoyl]-5-methyl-pyrrolidin-2-yl]-1H-benzimidazol-5-yl]phenyl]phenyl]-1H-imidazol-2-yl]-5-methyl-pyrrolidine-1-carboxylate (97 mg, 0.12 mmol) in MeOH (1 ml) is added HCl (638.0 µL of 4 M in dioxane, 2.5 mmol). The reaction mixture is stirred at rt for 3 hours, concentrated, co-evaporated with toluene and dried to afford the methyl N-[2-methyl-1-[(2S,5S)-2-methyl-5-[4-[4-[4-[2-[(2S,5S)-5-methylpyrrolidin-2-yl]-1H-imidazol-5-yl]phenyl]phenyl]-1H-benzimidazol-2-yl]pyrrolidine-1-carbonyl]propyl]-carbamate as a pale yellow residue and used in the next step without further purification.

Step III

Methyl N-[(1S)-1-[(2S,5S)-2-[4-[4-[4-[2-[(2S,5S)-1-[2-(methoxycarbonylamino)-3-methyl-butanoyl]-5-methyl-pyrrolidin-2-yl]-1H-benzimidazol-5-yl]phenyl]phenyl]-1H-imidazol-2-yl]-5-methyl-pyrrolidine-1-carbonyl]-2-methyl-propyl]carbamate To a mixture of methyl N-[2-methyl-1-[(2S,5S)-2-methyl-5-[4-[4-[4-[2-[(2S,5S)-5-methylpyrrolidin-2-yl]-1H-imidazol-5-yl]phenyl]phenyl]-1H-benzimidazol-2-yl]pyrrolidine-1-carbonyl]propyl]carbamate (88 mg, 0.126 mmol), (2S)-2-(methoxycarbonylamino)-3-methyl-butanoic acid (22 mg, 0.126 mmol) and 2,4,6-collidine (50.11 µl, 0.38 mmol) in DMF (3.5 ml) is added HATU (52.8 mg, 0.14 mmol) at 0° C. The reaction mixture is stirred at rt for 5 hours, diluted with EtOAc, washed with H$_2$O and brine. The organic phase is dried over Na$_2$SO$_4$, filtered and concentrated. The residue is purified by flash column chromatography on silica gel (1 to 20% MeOH in CH$_2$Cl$_2$) and repurified by reverse phase HPLC using a gradient of CH$_3$CN/water to afford the methyl N-[(1S)-1-[(2S,5S)-2-[4-[4-[4-[2-[(2S,5S)-1-[2-(methoxycarbonylamino)-3-methyl-butanoyl]-5-methyl-pyrrolidin-2-yl]-1H-benzimidazol-5-yl]phenyl]phenyl]-1H-imidazol-2-yl]-5-methyl-pyrrolidine-1-carbonyl]-2-methyl-propyl]carbamate (22 mg, 19.9%) as a white fluffy powder.

$^1$H NMR (400 MHz, CD$_3$OD): δ [ppm] 7.95-7.71 (m, 11H), 7.33-7.26 (m, 1H), 5.21 (m, 1H), 5.12 (m, 1H), 4.13-4.07 (m, 2H), 3.62 (s, 6H), 2.5 (m, 2H), 2.3-2.25 (m, 4H), 2.01-1.96 (m, 4H), 1.54 (m, 6H), 1.24-1.2 (m, 2H), 0.97 (m, 6H), 0.85 (m, 6H).

LC/MS: m/z=817.5 (M+H$^+$).

Intermediates

Methyl N-[(1S)-1-[(2S,5S)-2-(5-iodo-1H-benzimidazol-2-yl)-5-methyl-pyrrolidine-1-carbonyl]-2-methyl-propyl]carbamate

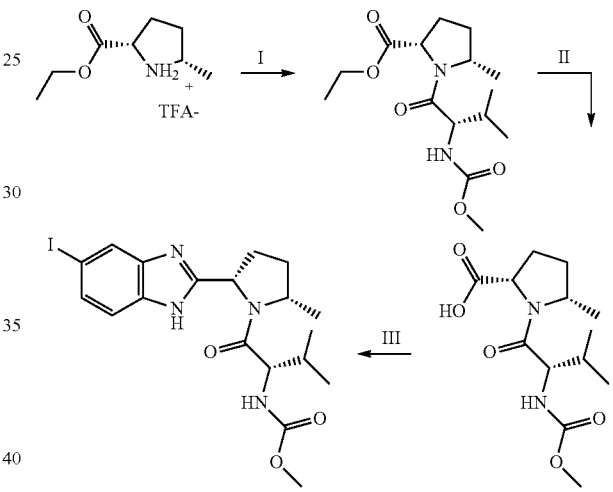

Step I

Ethyl (2S,5S)-1-[(2S)-2-(methoxycarbonylamino)-3-methyl-butanoyl]-5-methyl-pyrrolidine-2-carboxylate To a cold (0-4° C.) stirred solution of ethyl (2S,5S)-5-methylpyrrolidin-1-ium-2-carboxylate (7 g, 24.4 mmol) (J. Med. Chem. 2006, 49, 3520-3535), (2S)-2-(methoxycarbonylamino)-3-methyl-butanoic acid (4.5 g, 25.6 mmol), and HATU (9.7 g, 25.6 mmol) in DMF (66 ml) is added DIPEA (12.7 ml, 73.3 mmol). The resultant mixture is slowly warmed up to rt and stirred for 20 hours. The reaction mixture is diluted with water and extracted with ethyl acetate. The combined extracts are washed with sodium bicarbonate, brine, dried (Na$_2$SO$_4$) and concentrated. The residue is purified by flash column chromatography on silica gel using ethyl acetate-hexanes (3:7 to 4:6) as eluent to afford ethyl (2S,5S)-1-[(2S)-2-(methoxycarbonylamino)-3-methyl-butanoyl]-5-methyl-pyrrolidine-2-carboxylate (5.6 g, 73%) as a white solid.

LC/MS: m/z=314.9 (M+H$^+$).

Step II

(2S,5S)-1-[(2S)-2-(Methoxycarbonylamino)-3-methyl-butanoyl]-5-methyl-pyrrolidine-2-carboxylic acid To an ice-cold stirred solution of ethyl (2S,5S)-1-[(2S)-2-(methoxycarbonylamino)-3-methyl-butanoyl]-5-methyl-pyrrolidine-2-carboxylate (5.6 g, 17.8 mmol) in ethanol (18 ml) is added a solution of lithium hydroxide monohydrate (17.8 mL of 1.7 M, 30.3 mmol). The reaction mixture is stirred for 5 hours at rt. The reaction mixture is concentrated, diluted with water, washed with ether. The aqueous solution is acidified with aq. 1N HCl, extracted with $CH_2Cl_2$. The combined extracts are washed with brine, dried ($Na_2SO_4$), concentrated to afford (2S,5S)-1-[(2S)-2-(methoxycarbonylamino)-3-methyl-butanoyl]-5-methyl-pyrrolidine-2-carboxylic acid (5 g, 94%) as a white solid.
LC/MS: m/z=286.8 (M+H+).

Step III

Methyl N-[(1S)-1-[(2S,5S)-2-(5-iodo-1H-benzimidazol-2-yl)-5-methyl-pyrrolidine-1-carbonyl]-2-methyl-propyl]carbamate To a cold (0-4° C.) stirred solution of 4-iodobenzene-1,2-diamine (1.3 g, 5.3 mmol) and (2S,5S)-1-[(2S)-2-(methoxycarbonylamino)-3-methyl-butanoyl]-5-methyl-pyrrolidine-2-carboxylic acid (1.52 g, 4.99 mmol) in DMF (23.8 ml) is sequentially added HATU (2.321 g, 6.103 mmol) and 2,4,6-collidine (1.052 ml, 7.964 mmol). The reaction mixture is stirred at rt overnight, diluted with water, extracted with ethyl acetate. Combined extracts are washed with water, saturated bicarbonate solution, brine, dried ($Na_2SO_4$), concentrated and dried under high vacuum to afford crude amide. The resulting residue dissolved in acetic acid (28 ml) is heated at 60° C. for 8 hours. Acetic acid is removed, the residue neutralized with sat. $NaHCO_3$ solution, and diluted with ethyl acetate (20 ml). The aqueous solution is extracted with ethyl acetate, combined organic extracts are washed with aq. $NaHCO_3$ solution, brine, dried ($Na_2SO_4$), and concentrated. The concentrate is purified by flash column chromatography on silica gel using ethyl acetate-hexanes (1:1 to 7:3) as eluent afforded methyl N-[(1S)-1-[(2S,5S)-2-(5-iodo-1H-benzimidazol-2-yl)-5-methyl-pyrrolidine-1-carbonyl]-2-methyl-propyl]carbamate (2.3 g, 2.28 mmol, 92%).

$^1$H NMR (400 MHz, $CD_3OD$, 2:1 mixture of rotamers), For major rotamer δ 8.0-7.2 (m, 3H), 5.13 (dd, 1H), 4.78-4.70 (m, 1H), 4.2-4.1 (m, 1H), 3.64 (s, 3H), 2.8-1.8 (m, 5H), 1.49 (d, 3H), 0.93 (d, J=6.7 Hz, 3H), 0.80 (d, J=6.8 Hz, 3H). Selected peaks for minor rotamers. 5.48 (m, 1H), 3.58 (s, 3H), 1.205 (d, 3H), 0.99 (t, 6H).

LC/MS: m/z=484.9 (M+H+).

Intermediate tert-Butyl (2S,5S)-2-methyl-5-[4-[4-[4-(4,4,5,5-tetramethyl-1,3,2-dioxaborolan-2-yl)phenyl]phenyl]-1H-imidazol-2-yl]pyrrolidine-1-carboxylate

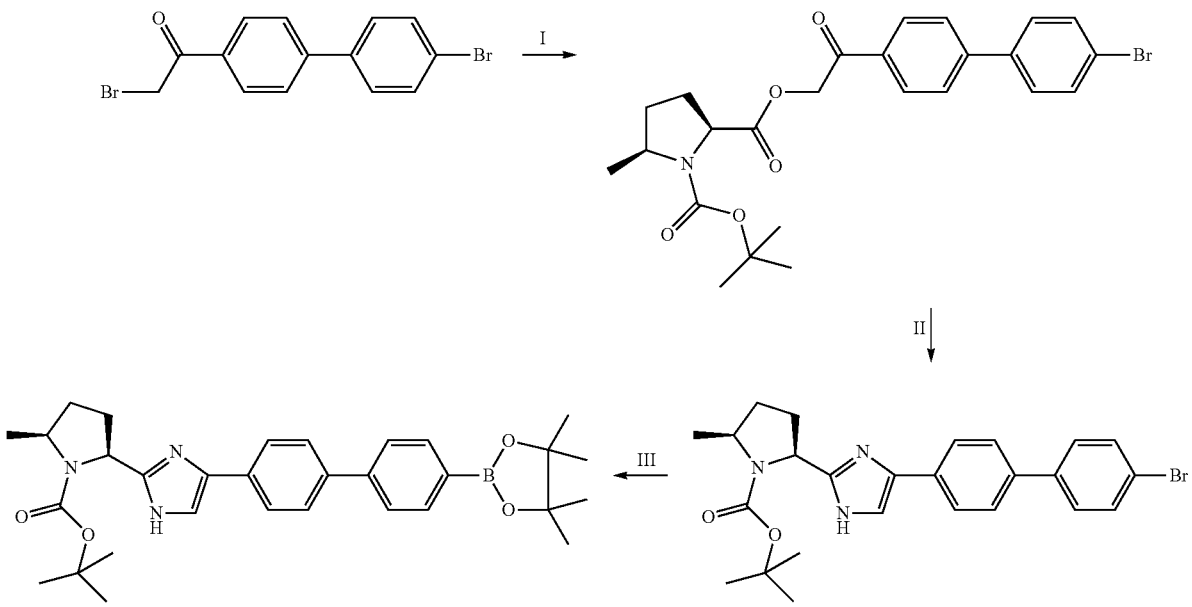

Step I

2-[2-[4-(4-Bromophenyl)phenyl]-2-oxo-ethyl]-1-tert-butyl-(2S,5S)-5-methylpyrrolidine-1,2-dicarboxylate To a mixture of 2-bromo-1-[4-(4-bromophenyl)phenyl]ethanone (735.3 mg, 2 mmol), (2S,5S)-1-tert-butoxycarbonyl-5-methyl-pyrrolidine-2-carboxylic acid (500 mg, 2.18 mmol) in acetonitrile (10 ml) (suspension) is added DIPEA (380 μL, 2.18 mmol). The reaction mixture is stirred at rt for 3 hours, diluted with EtOAc and $H_2O$. The organic phase is washed with brine, dried over Na$_2$SO$_4$, filtered and concentrated. The residue is purified by flash column chromatography on silica gel (0 to 30% EtOAc in Hexanes) to afford 2-[2-[4-(4-bromophenyl)phenyl]-2-oxo-ethyl]-1-tert-butyl-(2S,5S)-5-methylpyrrolidine-1,2-dicarboxylate (0.8 g, 76.7%) as a white solid.

Step II tert-Butyl (2S,5S)-2-[4-[4-(4-bromophenyl)phenyl]-1H-imidazol-2-yl]-5-methyl-pyrrolidine-1-carboxylate To 2-[2-[4-(4-bromophenyl)phenyl]-2-oxo-ethyl]1-tert-butyl (2S,5S)-5-methylpyrrolidine-1,2-dicarboxylate (620 mg, 1.23 mmol) in toluene (5.8 ml) is added ammonium acetate (1.9 g, 24.7 mmol). The reaction mixture is heated at 100° C. overnight, then diluted with EtOAc and H$_2$O. The organic phase is washed with brine, dried over Na$_2$SO$_4$, filtered and concentrated. The residue is purified by flash column chromatography on silica gel (5 to 50% EtOAc in Hexanes) to afford the tert-butyl (2S,5S)-2-[4-[4-(4-bromophenyl)phenyl]-1H-imidazol-2-yl]-5-methyl-pyrrolidine-1-carboxylate (430 mg, 72.2%).
LC/MS: m/z=483.9 (M+H$^+$).

Step III tert-Butyl (2S,5S)-2-methyl-5-[4-[4-[4-(4,4,5,5-tetramethyl-1,3,2-dioxaborolan-2-yl)phenyl]phenyl]-1H-imidazol-2-yl]pyrrolidine-1-carboxylate To a mixture of tert-butyl (2S,5S)-2-[4-[4-(4-bromophenyl)phenyl]-1H-imidazol-2-yl]-5-methyl-pyrrolidine-1-carboxylate (180 mg, 0.37 mmol), 4,4,5,5-tetramethyl-2-(4,4,5,5-tetramethyl-1,3,2-dioxaborolan-2-yl)-1,3,2-dioxaborolane (284 mg, 1.11 mmol) and Pd(DPPF)(Cl)$_2$.CH$_2$Cl$_2$ (30.47 mg, 0.03731 mmol) in DMF (1.800 ml) is added KOAc (183.1 mg, 1.866 mmol). The reaction mixture is stirred at 85° C. overnight, diluted with EtOAc and H$_2$O, and filtered through celite. The organic phase is washed with brine, dried over Na$_2$SO$_4$, filtered and concentrated. The residue is purified by flash column chromatography on silica gel (5 to 50% EtOAc in hexanes) to afford the tert-butyl (2S,5S)-2-methyl-5-[4-[4-[4-(4,4,5,5-tetramethyl-1,3,2-dioxaborolan-2-yl)phenyl]phenyl]-1H-imidazol-2-yl]pyrrolidine-1-carboxylate (180 mg, 91%) as a yellow oil.

LC/MS: m/z=530.1 (M+H$^+$).

Example 9

Methyl N-[(1S)-1-[(2S,4S)-2-[4-[4-[2-[2-[(2S,4S)-1-[(2S)-2-(methoxycarbonylamino)-3-methyl-butanoyl]-4-methyl-pyrrolidin-2-yl]-1H-benzimidazol-5-yl]ethynyl]phenyl]-1H-imidazol-2-yl]-4-methyl-pyrrolidine-1-carbonyl]-2-methyl-propyl]carbamate (Compound 9)

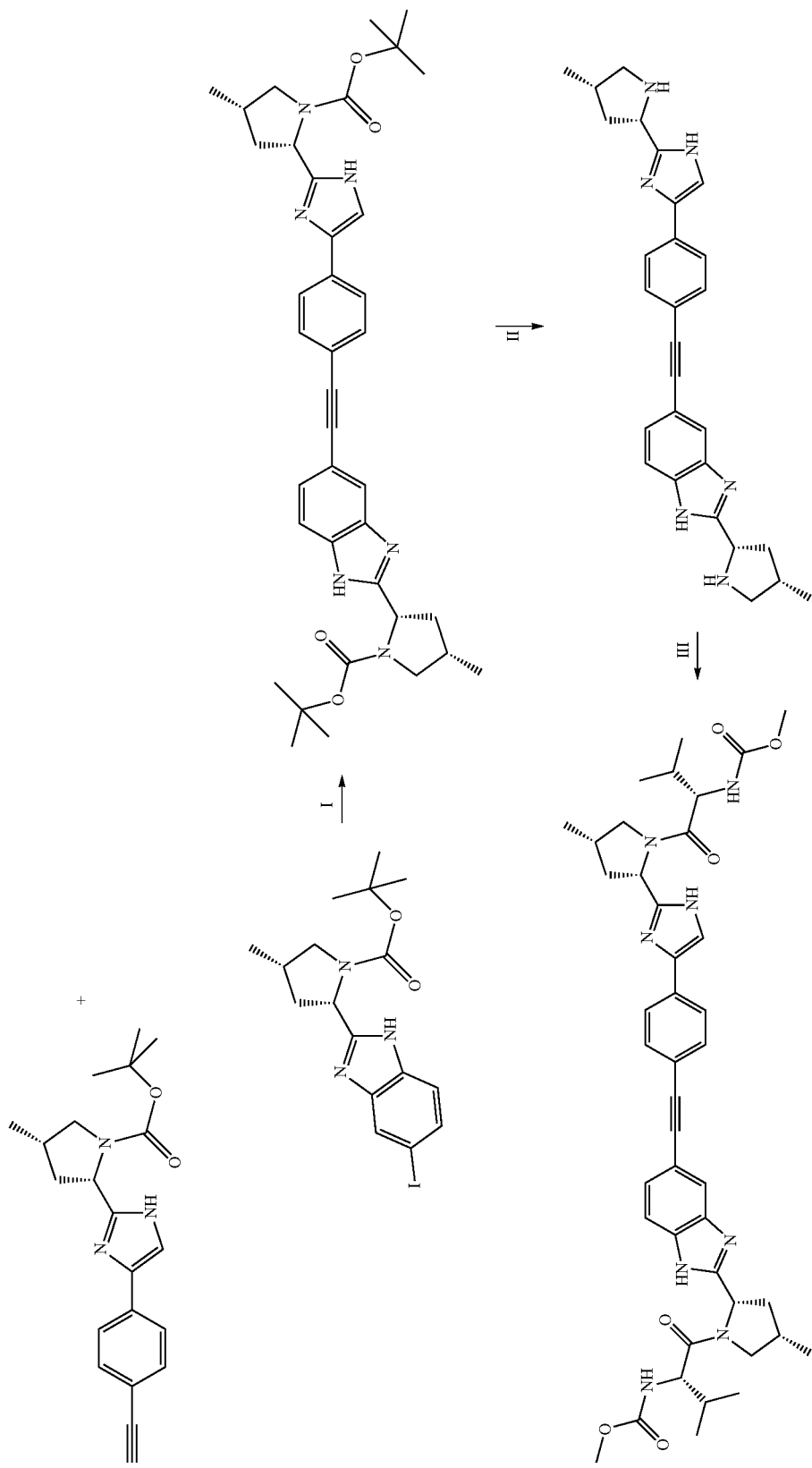

105

Step I tert-Butyl (2S,4S)-2-[4-[4-[2-[2-[(2S,4S)-1-tert-butoxycarbonyl-4-methyl-pyrrolidin-2-yl]-1H-benzimidazol-5-yl]ethynyl]phenyl]-1H-imidazol-2-yl]-4-methyl-pyrrolidine-1-carboxylate To a solution of tert-butyl (2S,4S)-2-(5-iodo-1H-benzimidazol-2-yl)-4-methyl-pyrrolidine-1-carboxylate (68.5 mg, 0.16 mmol) in DMF (3 mL) are sequentially added tert-butyl (2S,4S)-2-[4-(4-ethynylphenyl)-1H-imidazol-2-yl]-4-methyl-pyrrolidine-1-carboxylate (47 mg, 0.13 mmol), Pd(DPPF)(Cl)$_2$·CH$_2$Cl$_2$ (5.4 mg, 0.0067 mmol). The mixture is degassed well under vacuum and to it is added TEA (37 uL, 0.27 mmol), followed by CuI (1.2 mg, 0.0067 mmol). Then the reaction mixture is stirred under nitrogen at rt overnight. After removal of the solvent, the crude is purified by flash column chromatography on silica gel using methanol/CH$_2$Cl$_2$ 0-5% to obtain tert-butyl (2S,4S)-2-[4-[4-[2-[2-[(2S,4S)-1-tert-butoxycarbonyl-4-methyl-pyrrolidin-2-yl]-1H-benzimidazol-5-yl]ethynyl]phenyl]-1H-imidazol-2-yl]-4-methyl-pyrrolidine-1-carboxylate (56 mg, 64%).

LC/MS: m/z=651.41 (M+H$^+$).

Step II

2-[(2S,4S)-4-Methylpyrrolidin-2-yl]-5-[2-[4-[2-[(2S,4S)-4-methylpyrrolidin-2-yl]-1H-imidazol-4-yl]phenyl]ethynyl]-1H-benzimidazole HCl salt To a solution of tert-butyl (2S,4S)-2-[4-[4-[2-[2-[(2S,4S)-1-tert-butoxycarbonyl-4-methyl-pyrrolidin-2-yl]-1H-benzimidazol-5-yl]ethynyl]phenyl]-1H-imidazol-2-yl]-4-methyl-pyrrolidine-1-carboxylate (56 mg, 0.086 mmol) in methanol (2 mL) is added 4M HCl/dioxane (430 uL, 1.72 mmol). The mixture is stirred at rt for 3 hours. Removal of the solvent under vacuum gives 2-[(2S,4S)-4-methylpyrrolidin-2-yl]-5-[2-[4-[2-[(2S,4S)-4-methylpyrrolidin-2-yl]-1H-imidazol-4-yl]phenyl]ethynyl]-1H-benzimidazole HCl salt. The crude is used directly in the next step.

Step III

Methyl N-[(1S)-1-[(2S,4S)-2-[4-[4-[2-[2-[(2S,4S)-1-[(2S)-2-(methoxycarbonylamino)-3-methyl-butanoyl]-4-methyl-pyrrolidin-2-yl]-1H-benzimidazol-5-yl]ethynyl]phenyl]-1H-imidazol-2-yl]-4-methyl-pyrrolidine-1-carbonyl]-2-methyl-propyl]carbamate To a solution of 2-[(2S,4S)-4-methylpyrrolidin-2-yl]-5-[2-[4-[2-[(2S,4S)-4-methylpyrrolidin-2-yl]-1H-imidazol-4-yl]phenyl]ethynyl]-1H-benzimidazole HCl salt (25 mg, 0.042 mmol) in DMF (3 mL) is sequentially added (2S)-2-(methoxycarbonylamino)-3-methyl-butanoic acid (17.6 mg, 0.10 mmol), HATU (39.8 mg, 0.10 mmol) and DIPEA (73 uL, 0.42 mmol). The mixture is stirred at rt overnight. After removal of the solvent under reduced pressure, the residue is purified by flash column chromatography on silica gel using 0-7% MeOH/CH$_2$Cl$_2$, and the major fraction is further purified by reverse-phase prep-HPLC to obtain methyl N-[(1S)-1-[(2S,4S)-2-[4-[4-[2-[2-[(2S,4S)-1-[(2S)-2-(methoxycarbonylamino)-3-methyl-butanoyl]-4-methyl-pyrrolidin-2-yl]-1H-benzimidazol-5-yl]ethynyl]phenyl]-1H-imidazol-2-yl]-4-methyl-pyrrolidine-1-carbonyl]-2-methyl-propyl]carbamate (19 mg, 58.9%).

$^1$H NMR (CD$_3$OD, 400 MHz): 7.33-7.66 (m, 8H), 5.03-5.11 (m, 2H), 4.20 (m, 4H), 3.62 (s, 6H), 3.41 (m, 2H), 2.46 (m, 4H), 1.96 (m, 4H), 1.20 (m, 6H), 0.84 (m, 12H).

LC/MS: m/z=651.41 (M+H$^+$).

Intermediate tert-Butyl (2S,4S)-2-[4-(4-ethynylphenyl)-1H-imidazol-2-yl]-4-methyl-pyrrolidine-1-carboxylate

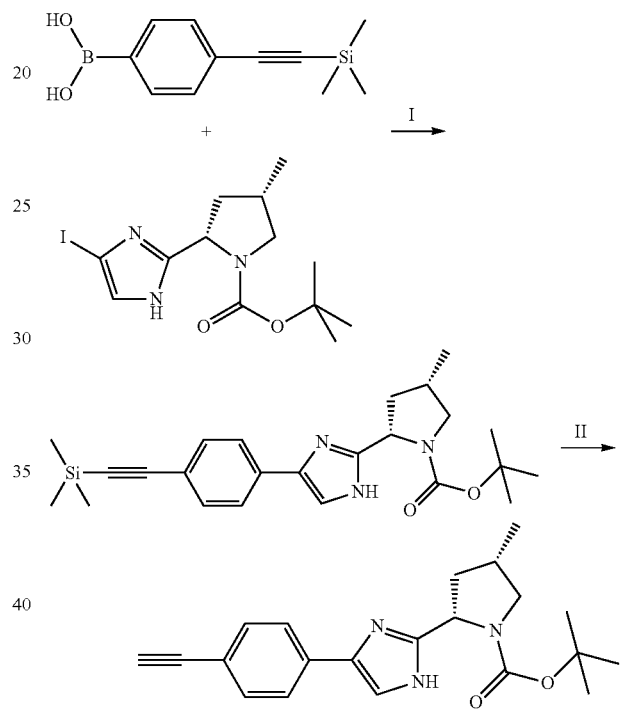

Step I tert-Butyl (2S,4S)-4-methyl-2-[4-[4-(2-trimethylsilylethynyl)phenyl]-1H-imidazol-2-yl]pyrrolidine-1-carboxylate To a solution of tert-butyl (2S,4S)-2-(4-iodo-1H-imidazol-2-yl)-4-methyl-pyrrolidine-1-carboxylate (150 mg, 0.3976 mmol) and ([4-(2-trimethylsilylethynyl)phenyl]boronic acid (130 mg, 0.6 mmol) in isopropanol (3 mL) are added sequentially Pd(DPPF)(Cl)$_2$·CH$_2$Cl$_2$ (16 mg, 0.02 mmol), and 2 M NaHCO$_3$ (600 uL, 1.2 mmol). The mixture is heated to 85° C. in a sealed tube overnight. After reaction, the solvent is removed under reduced pressure and the residue is purified by flash column chromatography on silica gel using methanol/CH$_2$Cl$_2$ 0-5% to provide tert-butyl (2S,4S)-4-methyl-2-[4-[4-(2-trimethylsilylethynyl)phenyl]-1H-imidazol-2-yl]pyrrolidine-1-carboxylate (168 mg, 95%).

LC/MS: m/z=423.98 (M+H$^+$).

Step II tert-Butyl (2S,4S)-2-[4-(4-ethynylphenyl)-1H-imidazol-2-yl]-4-methyl-pyrrolidine-1-carboxylate

To a solution of tert-butyl (2S,4S)-4-methyl-2-[4-[4-(2-trimethylsilylethynyl)phenyl]-1H-imidazol-2-yl]pyrrolidine-1-carboxylate (57 mg, 0.1346 mmol) in MeOH (2 mL) is added K$_2$CO$_3$ (37.2 mg, 0.27 mmol). The mixture is stirred at rt for 2 hours. After removal of the solvent under reduced pressure, the residue is purified by flash column chromatography on silica gel using 0-5% MeOH/CH$_2$Cl$_2$ to provide tert-butyl (2S,4S)-2-[4-(4-ethynylphenyl)-1H-imidazol-2-yl]-4-methyl-pyrrolidine-1-carboxylate (47 mg, 99%).

$^1$H NMR (CD$_3$OD, 400 MHz): 7.33-7.66 (m, 5H), 4.79 (m, 1H), 3.79 (m, 1H), 3.46 (s, 1H), 3.14 (m, 1H), 2.29-2.46 (m, 2H), 1.70 (m, 1H), 1.09-1.40 (m, 12H).

To a solution of 2-[(2S,4S)-4-methylpyrrolidin-2-yl]-5-[2-[4-[2-[(2S,4S)-4-methylpyrrolidin-2-yl]-1H-imidazol-4-yl]phenyl]ethynyl]-1H-benzimidazole HCl salt (32 mg, 0.053 mmol) in DMF (3 mL) are sequentially added (2S)-2-[methoxycarbonyl(methyl)amino]-3-methyl-butanoic acid (24.3 mg, 0.13 mmol), HATU (51 mg, 0.13 mmol) and DIPEA (93 uL, 0.53 mmol). The mixture is stirred at rt overnight. After removal of the solvent under reduced pressure, the residue is purified by flash column chromatography on silica gel using 0-7% MeOH/CH$_2$Cl$_2$, and the major fraction is further purified by reverse-phase prep-HPLC to obtain methyl N-[(1S)-1-[(2S,4S)-2-[4-[4-[2-[2-[(2S,4S)-1-[(2S)-2-[methoxycarbonyl(methyl)amino]-3-methyl-butanoyl]-4-methyl-pyrrolidin-2-yl]-1H-benzimidazol-5-yl]ethynyl]phenyl]-1H-imidazol-2-yl]-4-methyl-pyrrolidine-1-carbonyl]-2-methyl-propyl]-N-methyl-carbamate (20 mg, 45.4%).

$^1$H NMR (CD$_3$OD, 400 MHz): 7.33-7.66 (m, 8H), 4.91-5.09 (m, 2H), 4.20-4.57 (m, 4H), 3.62 (s, 6H), 3.41 (m, 2H), 2.83 (m, 6H), 1.84-2.60 (m, 8H), 1.20 (m, 6H), 0.84 (m, 12H).

LC/MS: m/z=793.38 (M+H$^+$).

Example 10

Methyl N-[(1S)-1-[(2S,4S)-2-[4-[4-[2-[2-[(2S,4S)-1-[(2S)-2-[methoxycarbonyl-(methyl)amino]-3-methyl-butanoyl]-4-methyl-pyrrolidin-2-yl]-1H-benzimidazol-5-yl]ethynyl]phenyl]-1H-imidazol-2-yl]-4-methyl-pyrrolidine-1-carbonyl]-2-methyl-propyl]-N-methyl-carbamate (Compound 10)

Example 11

Methyl N-[(1S)-1-[(2S,4S)-2-[4-[2-[4-[2-[(2S,4S)-1-[(2S)-2-(methoxycarbonylamino)-3-methyl-butanoyl]-4-methyl-pyrrolidin-2-yl]-1H-benzimidazol-5-yl]phenyl]ethynyl]-1H-imidazol-2-yl]-4-methyl-pyrrolidine-1-carbonyl]-2-methyl-propyl]carbamate (Compound 12)

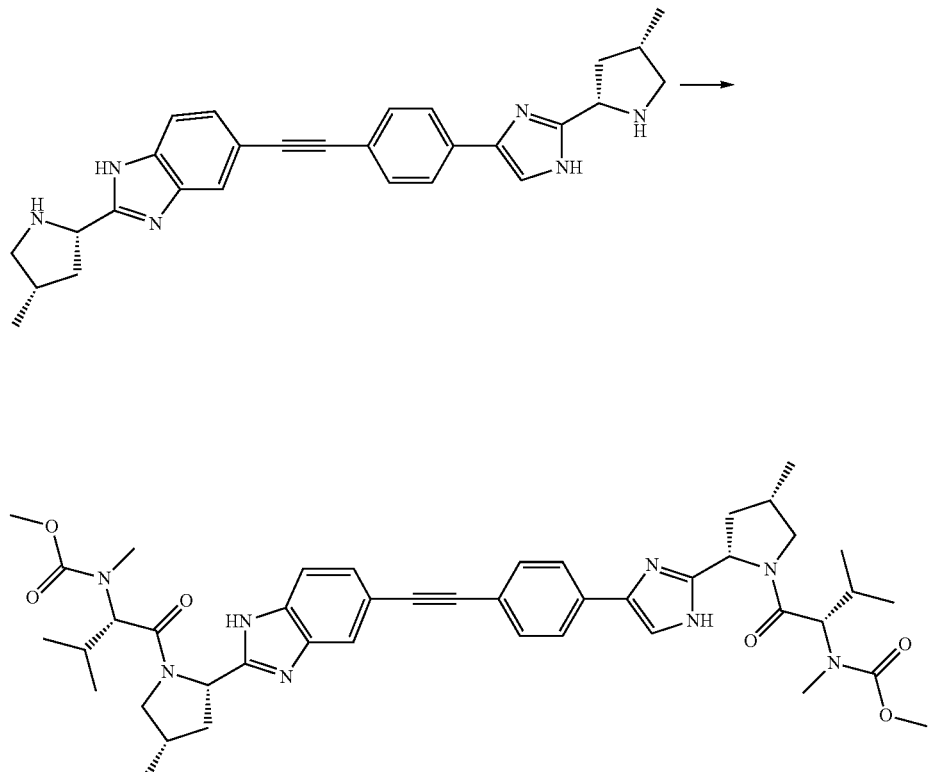

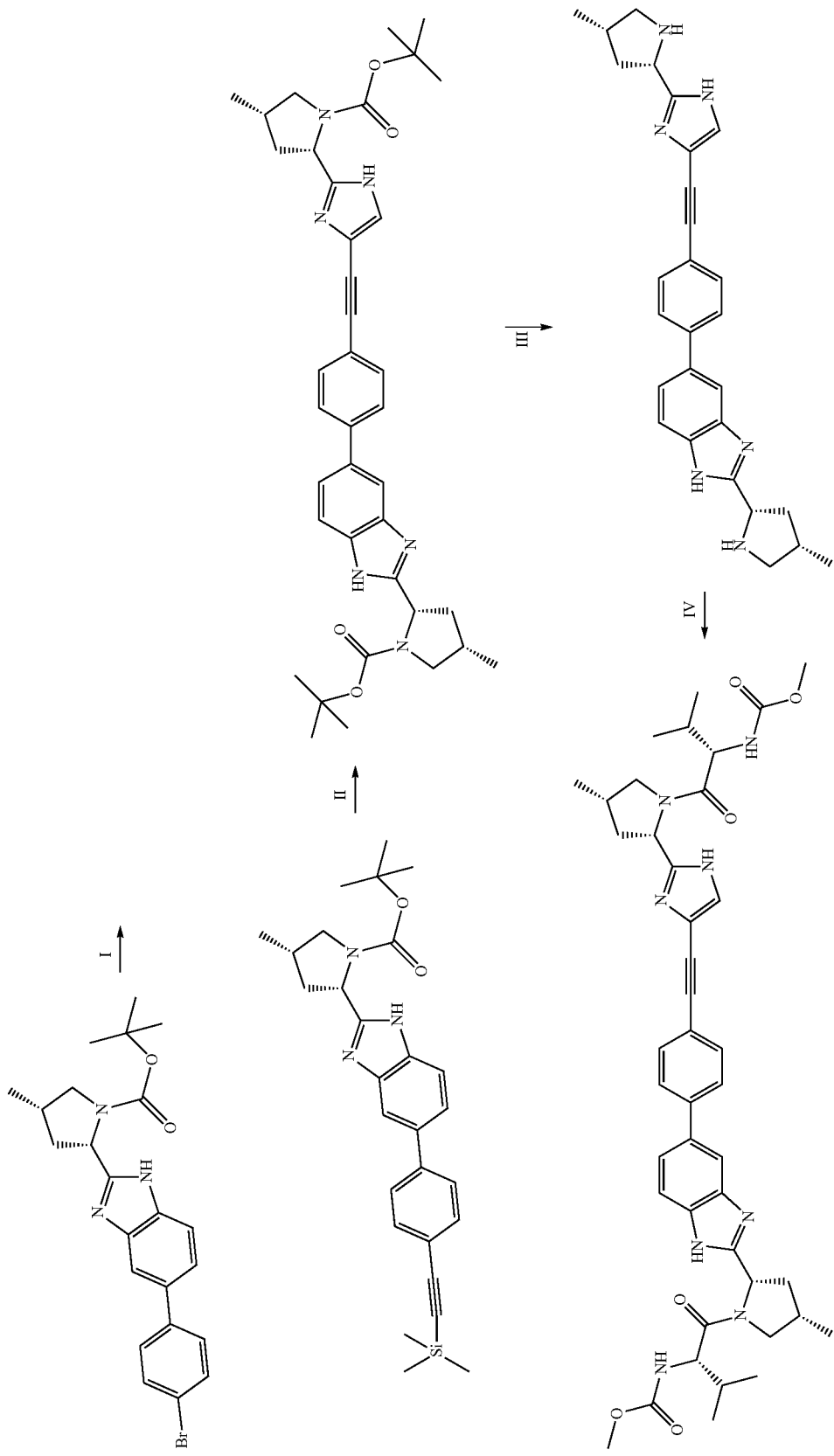

Step I tert-Butyl (2S,4S)-4-methyl-2-[5-[4-(2-trimethylsilylethynyl)phenyl]-1H-benzimidazol-2-yl]pyrrolidine-1-carboxylate Ethynyl-trimethyl-silane (34.44 mg, 49.55 µL, 0.3506 mmol), tert-butyl (2S,4S)-2-[5-(4-bromophenyl)-1H-benzimidazol-2-yl]-4-methyl-pyrrolidine-1-carboxylate (80 mg, 0.1753 mmol), Pd(DPPF)(Cl)$_2$·CH$_2$Cl$_2$ (14.32 mg, 0.01753 mmol), TEA (35.48 mg, 48.87 µL, 0.3506 mmol) and CuI (3.339 mg, 0.01753 mmol) are dissolved to dry DMF (2 mL). The mixture is stirred at 70° C. under N$_2$ overnight. After removal of the solvent under reduced pressure, the residue is purified by flash column chromatography on silica gel SP1 25M using methanol/CH$_2$Cl$_2$ (0-5%) in 20 cv to provide tert-butyl (2S,4S)-4-methyl-2-[5-[4-(2-trimethylsilylethynyl)phenyl]-1H-benzimidazol-2-yl]pyrrolidine-1-carboxylate (40 mg).

LC/MS: m/z=474.15 (M+H$^+$).

Step II tert-Butyl (2S,4S)-2-[4-[2-[4-[2-[(2S,4S)-1-tert-butoxycarbonyl-4-methyl-pyrrolidin-2-yl]-1H-benzimidazol-5-yl]phenyl]ethynyl]-1H-imidazol-2-yl]-4-methyl-pyrrolidine-1-carboxylate The well-degassed solution of tert-butyl (2S,4S)-2-(4-iodo-1H-imidazol-2-yl)-4-methyl-pyrrolidine-1-carboxylate (38.21 mg, 0.1013 mmol), tert-butyl (2S,4S)-4-methyl-2-[5-[4-(2-trimethylsilylethynyl)phenyl]-1H-benzimidazol-2-yl]pyrrolidine-1-carboxylate (40 mg, 0.08444 mmol), Pd(DPPF)(Cl)$_2$·CH$_2$Cl$_2$ (6.896 mg, 0.008444 mmol), CuI (3.217 mg, 0.01689 mmol), DBU (128.5 mg, 126.2 µL, 0.8444 mmol), and water (4.563 mg, 4.563 µL, 0.2533 mmol) in DMF (3 mL) is stirred at 70° C. under N$_2$ overnight. After removal of the solvent under reduced pressure, the residue is purified by flash column chromatography on silica gel using methanol/CH$_2$Cl$_2$ (0-6%) to provide the desired tert-butyl (2S,4S)-2-[4-[2-[4-[2-[(2S,4S)-1-tert-butoxycarbonyl-4-methyl-pyrrolidin-2-yl]-1H-benzimidazol-5-yl]phenyl]ethynyl]-1H-imidazol-2-yl]-4-methyl-pyrrolidine-1-carboxylate (34 mg, 61.8% yield). LC/MS: m/z=651.42 (M+H$^+$).

Step III

2-[(2S,4S)-4-Methylpyrrolidin-2-yl]-5-[4-[2-[2-[(2S,4S)-4-methylpyrrolidin-2-yl]-1H-imidazol-4-yl]ethynyl]phenyl]-1H-benzimidazole tert-Butyl (2S,4S)-2-[4-[2-[4-[2-[(2S,4S)-1-tert-butoxycarbonyl-4-methyl-pyrrolidin-2-yl]-1H-benzimidazol-5-yl]phenyl]ethynyl]-1H-imidazol-2-yl]-4-methyl-pyrrolidine-1-carboxylate (28 mg, 0.04302 mmol) is dissolved in methanol (2 mL) and then to it is added HCl (107.6 µL of 4 M, 0.4302 mmol). The mixture is stirred at rt overnight. After removal of the solvent under reduced pressure, 2-[(2S,4S)-4-methylpyrrolidin-2-yl]-5-[4-[2-[2-[(2S,4S)-4-methylpyrrolidin-2-yl]-1H-imidazol-4-yl]ethynyl]phenyl]-1H-benzimidazole is used as such in the next step.

Step IV

Methyl N-[(1S)-1-[(2S,4S)-2-[4-[2-[4-[2-[(2S,4S)-1-[(2S)-2-(methoxycarbonylamino)-3-methyl-butanoyl]-4-methyl-pyrrolidin-2-yl]-1H-benzimidazol-5-yl]phenyl]ethynyl]-1H-imidazol-2-yl]-4-methyl-pyrrolidine-1-carbonyl]-2-methyl-propyl]carbamate The solution of (2S)-2-(methoxycarbonylamino)-3-methyl-butanoic acid (19.09 mg, 0.1090 mmol), 2-[(2S,4S)-4-methylpyrrolidin-2-yl]-5-[4-[2-[2-[(2S,4S)-4-methylpyrrolidin-2-yl]-1H-imidazol-4-yl]ethynyl]phenyl]-1H-benzimidazole (26 mg, 0.04359 mmol), HATU (41.45 mg, 0.1090 mmol), and DIPEA (56.34 mg, 75.93 µL, 0.4359 mmol) in DMF (2 mL) is stirred at rt overnight. After removal of the solvent, the crude is purified by flash column chromatography on silica gel using methanol/CH$_2$Cl$_2$ 0-6%. The major fraction is further purified on reverse-phase prep HPLC to obtain methyl N-[(1S)-1-[(2S,4S)-2-[4-[2-[4-[2-[(2S,4S)-1-[(2S)-2-(methoxycarbonylamino)-3-methyl-butanoyl]-4-methyl-pyrrolidin-2-yl]-1H-benzimidazol-5-yl]phenyl]ethynyl]-1H-imidazol-2-yl]-4-methyl-pyrrolidine-1-carbonyl]-2-methyl-propyl]carbamate (18 mg, 53% yield) as a white solid.

$^1$H NMR (CD$_3$OD, 400 MHz): 7.51-7.66 (m, 8H), 4.92-5.15 (m, 2H), 4.20 (m, 4H), 3.62 (s, 6H), 3.41 (m, 2H), 2.46 (m, 4H), 1.96 (m, 4H), 1.20 (m, 6H), 0.84 (m, 12H).

LC/MS: m/z=765.53 (M+H$^+$).

Example 12

Methyl N-[(1S)-1-[(2S,4S)-2-[4-[5-[2-[(2S,4S)-1-[(2S)-2-(methoxycarbonylamino)-3-methyl-butanoyl]-4-methyl-pyrrolidin-2-yl]-1H-benzimidazol-5-yl]thieno[3,2-b]thiophen-2-yl]-1H-imidazol-2-yl]-4-methyl-pyrrolidine-1-carbonyl]-2-methyl-propyl]carbamate (Compound 16)

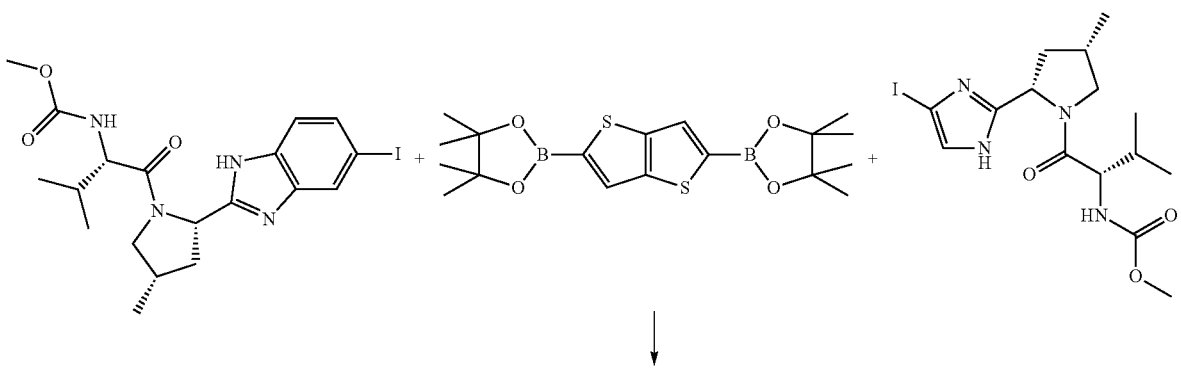

-continued

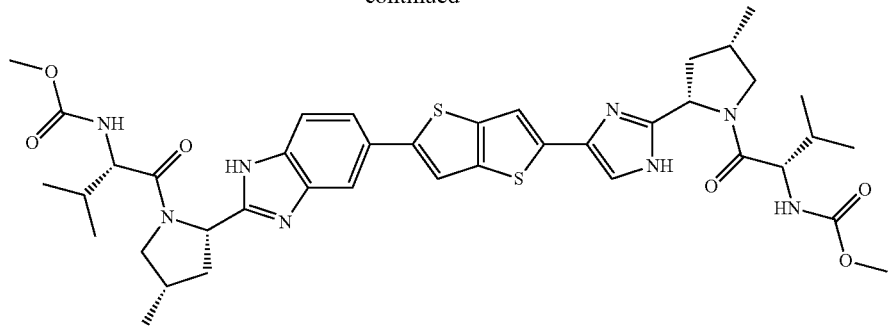

To a degassed (vacuum/nitrogen flush) mixture of methyl N-[(1S)-1-[(2S,4S)-2-(4-iodo-1H-imidazol-2-yl)-4-methyl-pyrrolidine-1-carbonyl]-2-methyl-propyl]carbamate (153.5 mg, 0.3347 mmol), methyl N-[(1S)-1-[(2S,4S)-2-(5-iodo-1H-benzimidazol-2-yl)-4-methyl-pyrrolidine-1-carbonyl]-2-methyl-propyl]carbamate (162.1 mg, 0.3347 mmol), 4,4,5,5-tetramethyl-2-[5-(4,4,5,5-tetramethyl-1,3,2-dioxaborolan-2-yl)thieno[3,2-b]thiophen-2-yl]-1,3,2-dioxaborolane (125 mg, 0.3188 mmol) and $K_2CO_3$ (220.3 mg, 1.594 mmol) in degassed isopropanol (3.750 mL) and $H_2O$ (1.250 mL) are added [3-(2-dicyclohexylphosphanylphenyl)-2,4-dinnethoxy-phenyl]sulfonyloxysodium (VPHOS) (13.07 mg, 0.02550 mmol) and $Pd(OAc)_2$ (1.431 mg, 0.006376 mmol). After degassing twice, reaction mixture is heated at 90° C. for 16 hours, then diluted with ethyl acetate (30 mL). The aqueous solution is discarded, and the organic solution is washed with water, brine, dried ($Na_2SO_4$) and concentrated. The residue is purified by silica gel chromatography using ethyl acetate to 8% MeOH-EtOAc as eluent to afford a mixture of products (160 mg) as yellow solid. The desired compound is isolated by reverse phase preparative HPLC to afford methyl N-[(1S)-1-[(2S,4S)-2-[4-[5-[2-[(2S,4S)-1-[(2S)-2-(methoxycarbonylamino)-3-methyl-butanoyl]-4-methyl-pyrrolidin-2-yl]-1H-benzimidazol-5-yl]thieno[3,2-b]thiophen-2-yl]-1H-imidazol-2-yl]-4-methyl-pyrrolidine-1-carbonyl]-2-methyl-propyl]carbamate (34.4 mg) as yellow solid.

$^1$H NMR (400 MHz, $CD_3OD$) δ 7.8-7.2 (m, 6H), 5.14 (dd, 1H), 5.02 (dd, 1H), 4.29 (t, 1H), 4.25-4.18 (m, 3H), 3.64 (s, 3H), 3.49-3.36 (m, 2H), 2.66-2.26 (m, 4H), 2.09-1.80 (m, 4H), 1.21 (d, 3H), 1.19 (d, 3H), 0.95-0.89 (m, 6H), 0.87 (d, 3H), 0.835 (d, 3H).

LC/MS: m/z=803.34 (M+H$^+$).

Intermediate (2S)-tert-Butyl 2-(4-(4'-bromo-[1,1'-biphenyl]-4-yl)-1H-imidazol-2-yl)pyrrolidine-1-carboxylate

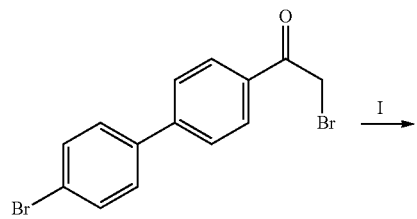

-continued

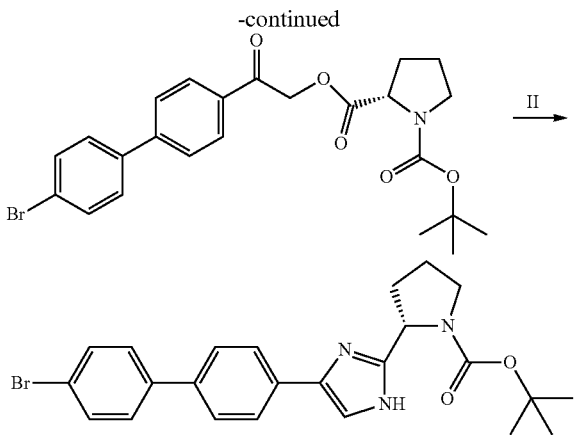

Step I (2S,4S)-2-(2-(4'-Bromobiphenyl-4-yl)-2-oxoethyl)1-tert-butyl 4-methylpyrrolidine-1,2-dicarboxylate To a solution of 2-bromo-1-[4-(4-bromophenyl)phenyl]ethanone (759 mg, 1.897 mmol) and (2S)-1-tert-butoxycarbonylpyrrolidine-2-carboxylic acid (484.3 mg, 2.25 mmol) in acetonitrile (7.5 mL) is added DIPEA (290.8 mg, 392 µL, 2.25 mmol). The reaction mixture is stirred at room temperature for 2 hours and washed with brine (3×5 mL). The organic layer is concentrated to dryness. The residue is diluted with toluene (5 mL) and concentrated to dryness and purified by flash column chromatography on silica gel (2 to 20% EtOAc in hexanes) to obtain (2S,4S)-2-(2-(4'-bromobiphenyl-4-yl)-2-oxoethyl)1-tert-butyl 4-methylpyrrolidine-1,2-dicarboxylate (855 mg, 93%) that is used as such for the next step.

Step II (2S)-tert-Butyl 2-(4-(4'-bromo-[1,1'-biphenyl]-4-yl)-1H-imidazol-2-yl)pyrrolidine-1-carboxylate To a solution of (2S,4S)-2-(2-(4'-bromobiphenyl-4-yl)-2-oxoethyl) 1-tert-butyl 4-methylpyrrolidine-1,2-dicarboxylate (855 mg, 1.751 mmol) in toluene (8 mL) is added ammonium acetate (2.699 g, 35.02 mmol). The reaction mixture is heated at 100° C. for 24 hours, cooled to rt, and diluted with water (10 mL). The layers are separated and the aqueous layer is extracted with EtOAc (10 mL), and the combined organic layers are dried over $Na_2SO_4$, filtered, and concentrated to dryness. The residue is purified by flash column chromatography on silica gel (6 to 80% EtOAc in hexanes) to give (2S)-tert-butyl 2-(4-(4'-bromo-[1,1'-biphenyl]-4-yl)-1H-imidazol-2-yl)pyrrolidine-1-carboxylate (511 mg, 62%).

Intermediate

4,4,5,5-Tetramethyl-2-[5-(4,4,5,5-tetramethyl-1,3,2-dioxaborolan-2-yl)thieno[3,2-b]thiophen-2-yl]-1,3,2-dioxaborolane

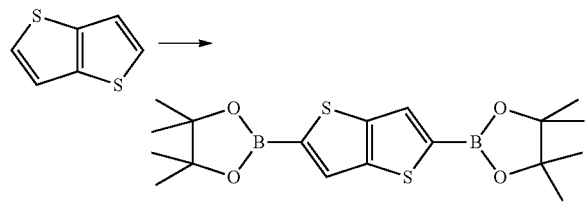

To a solution of thieno[3,2-b]thiophene (1.5 g, 10.70 mmol) in THF (25.5 mL) at −78° C. under $N_2$ is added dropwise a solution of BuLi in hexanes (8.988 mL of 2.5 M, 22.47 mmol), stirred for 20 min, cooling bath is replaced with ice bath and stirred for 50 min. The resultant thick suspension is quenched with 2-isopropoxy-4,4,5,5-tetramethyl-1,3,2-dioxaborolane (4.181 g, 4.584 mL, 22.47 mmol). The reaction mixture is kept for overnight and then quenched with saturated aq. $NH_4Cl$ solution. After extraction with $CH_2Cl_2$ (2×100 mL), the combined extracts are washed with brine and dried ($Na_2SO_4$). Organic solution is diluted with ~20 mL of ethyl acetate, concentrated slowly on rotary evaporator until $CH_2Cl_2$ is removed. The resultant white fine crystals are collected by filtration. The solid is washed with heptanes and dried under high vacuum to afford 4,4,5,5-tetramethyl-2-[5-(4,4,5,5-tetramethyl-1,3,2-dioxaborolan-2-yl)thieno[3,2-b]thiophen-2-yl]-1,3,2-dioxaborolane (2.57 g, 6.554 mmol, 61.25%) as half-white solid. $^1$H NMR (400 MHz, CDCl$_3$) δ 7.75 (s, 2H), 1.343 (s, 12H).

Intermediate

(2S)-2-(Methoxycarbonylamino)-3-methyl-butanoic acid

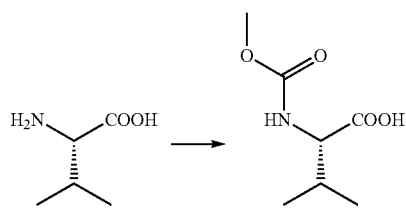

L-Valine (140 g, 1.195 mol) is added to a stirred solution of 1 M sodium hydroxide (1.183 L, 1.183 mol). After complete dissolution, sodium carbonate (65.8 g, 621.4 mmol) is added followed by methyl chloroformate (122 g, 99.75 mL, 1.291 mol) at 0° C. over 40 minutes. The reaction mixture is stirred at rt for 3.5 hours, then washed with diethyl ether (3×200 ml). The aqueous layer is cooled to 0° C., and acidified to pH 1-2. The white solid formed is filtered on a Buchner, washed with cold water and dried to afford the title compound (2S)-2-(methoxycarbonylamino)-3-methyl-butanoic acid (140 g, 67%).

Intermediate

(2S)-2-[Methoxycarbonyl(methyl)amino]-3-methyl-butanoic acid

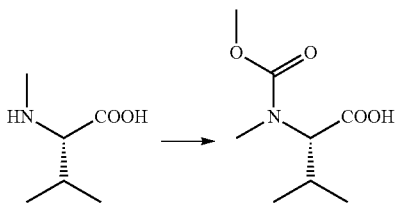

(2S)-3-Methyl-2-methylamino-butanoic acid (5 g, 38.12 mmol) is added to a stirring solution of sodium hydroxide (76.2 mL of 1 M, 76.24 mmol). After complete dissolution, sodium carbonate (2.1 g, 19.82 mmol) is added followed by methyl chloroformate (3.18 mL, 41.17 mmol) at 0° C. over 40 minutes. The reaction mixture is stirred at rt for 4 hours, and then washed with diethyl ether (2×75 ml). The aqueous layer is cooled to 0° C., acidified to pH 1-2 and extracted with $CH_2Cl_2$. The organic phase is dried over $MgSO_4$, filtered and concentrated to dryness to give the title compound (2S)-2-[methoxycarbonyl(methyl)amino]-3-methyl-butanoic acid (5.12 g, 71%) as a clear oil.

Intermediate

Methyl N-[(1S)-1-[(2S,4S)-2-(4-iodo-1H-imidazol-2-yl)-4-methyl-pyrrolidine-1-carbonyl]-2-methyl-propyl]carbamate

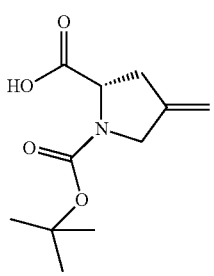 →I→ 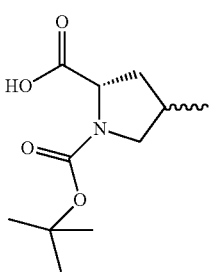 →II→ →III→ →IV→

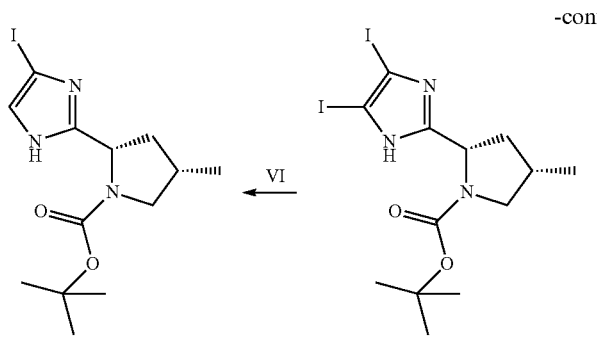
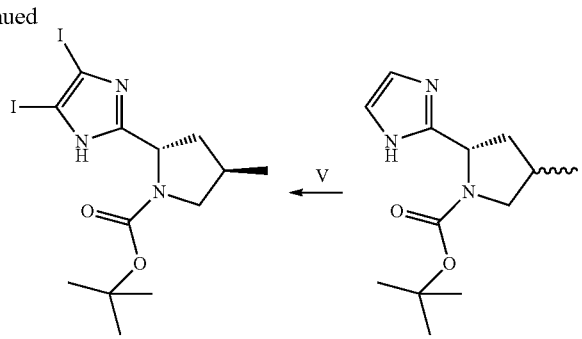

-continued

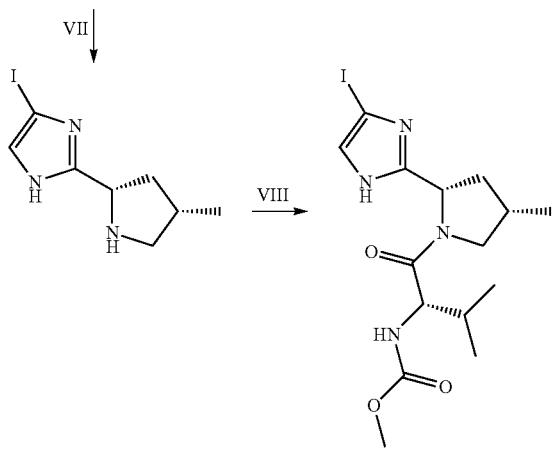

Step I (2S)-1-tert-Butoxycarbonyl-4-methyl-pyrrolidine-2-carboxylic acid

A solution of (2S)-1-tert-butoxycarbonyl-4-methylene-pyrrolidine-2-carboxylic acid (25 g, 110 mmol) in methanol or ethanol (250 mL) is purged 3 times under $N_2$ before the addition of $PtO_2$ (2.5 g, 11 mmol). The solution is purged again with vacuum and $H_2$, and this process is repeated three times. Then the reaction mixture is stirred for 20 hours under one atmosphere of hydrogen. The reaction mixture is filtered through celite to remove the catalyst, and the filtrate is concentrated to dryness to give (2S)-1-tert-butoxycarbonyl-4-methyl-pyrrolidine-2-carboxylic acid (24.9 g, 98.7%) as a white solid (mixture of cis/trans approx. 80/20 ratio).

Step II tert-Butyl (2S)-2-(hydroxymethyl)-4-methyl-pyrrolidine-1-carboxylate To a solution of (2S)-1-tert-butoxycarbonyl-4-methyl-pyrrolidine-2-carboxylic acid (26.6 g, 116.0 mmol) in THF (160 mL) is added 1 M borane in THF (243.6 mL, 243.6 mmol) at 0° C. The reaction mixture is stirred at rt overnight. Then a saturated aqueous solution of $NH_4Cl$ (50 mL) is carefully added (dropwise) at 4° C., followed by $H_2O$ (100 mL). The mixture is extracted with EtOAc and the organic phase is washed with $H_2O$, dried over $Na_2SO_4$, filtered and concentrated to dryness. The residue is purified by flash column chromatography on silica gel (0 to 20% EtOAc in Hexanes) to give tert-butyl (2S)-2-(hydroxymethyl)-4-methyl-pyrrolidine-1-carboxylate (23.5 g, 94%).

Step III tert-Butyl (2S)-2-formyl-4-methyl-pyrrolidine-1-carboxylate

To a solution of oxalyl chloride (319.4 mL of 2 M, 638.8 mmol) in $CH_2Cl_2$ (460 mL) is added DMSO (90.69 mL, 1.28 mol) over 30 minutes, keeping the internal temperature around -60° C. tert-Butyl (2S)-2-(hydroxymethyl)-4-methyl-pyrrolidine-1-carboxylate (55 g, 255.5 mmol) in $CH_2Cl_2$ (460 mL) is then added over 50 minutes at -78° C. The reaction mixture is stirred for 20 minutes before dropwise addition of DIPEA (445 mL, 2.55 mol). The reaction mixture is stirred at -78° C. for 2 hours and is allowed to warm to rt over 2 hours. To this mixture is added slowly 1N HCl (800 mL). After stirring, the organic phase is separated, dried over $Na_2SO_4$, filtered and concentrated to dryness. The residue is purified by flash column chromatography on silica gel (0 to 20% EtOAc in Hexanes) to give tert-butyl (2S)-2-formyl-4-methyl-pyrrolidine-1-carboxylate (48.5 g, 227.4 mmol, 85%) as a brown oil (mixture cis/trans 77/23).

Step IV tert-Butyl (2S)-2-(1H-imidazol-2-yl)-4-methyl-pyrrolidine-1-carboxylate To a stirred solution of tert-butyl (2S)-2-formyl-4-methyl-pyrrolidine-1-carboxylate (45 g, 211 mmol) in MeOH (90 mL) is added $NH_4OH$ (90 mL). Oxaldehyde (85.6 g, 67.7 mL of 40% w/v, 466.7 mmol) is added by portions (exothermic reaction). The reaction mixture is stirred at rt overnight, diluted with $H_2O$ (300 ml) and is extracted with $CH_2Cl_2$ (2×300 ml). The aqueous phase is extracted for second time with CH$_2$Cl$_2$ and the combined organic layers are washed with H$_2$O, dried over Na$_2$SO$_4$, filtered and evaporated to dryness. The residue is purified by re-crystallization in EtOAc, to give 24 g of the title compound. The filtrate is evaporated to dryness and the residue is purified by flash column chromatography on silica gel (25 to 100% EtOAc in Hexanes) to give 9.67 g of title compound. The two isolated solids are combined to give tert-butyl (2S)-2-(1H-imidazol-2-yl)-4-methyl-pyrrolidine-1-carboxylate (33.67 g, 63.5%).

$^1$H NMR (400 MHz, dmso-d6, mixture of cis and trans isomers and its rotamers) δ 11.71 (s, 1 H), 6.85 (s, 2 H), 4.86-4.58 (m, 2 H), 3.75-3.5 (m, 2 H), 3.03-2.82 (m, 2 H), 2.36-2.25 (m, 1 H), 2.25-2.11 (m, 1 H), 1.6-1.45 (m, 1 H), 1.39 (s, minor rotamer of minor isomer), 1.37 (s, minor rotamer of major isomer), 1.15 (s, major rotamer of minor isomer), 1.09 (s, major rotamer of major isomer) 1.005 (d, minor isomer) 0.99 (d, major isomer).

Step V tert-Butyl (2S,4S)-2-(4,5-diiodo-1H-imidazol-2-yl)-4-methyl-pyrrolidine-1-carboxylate To a stirred solution of tert-butyl (2S)-2-(1H-imidazol-2-yl)-4-methyl-pyrrolidine-1-carboxylate (36.6 g, 145.6 mmol) in CH$_2$Cl$_2$ (366.0 mL) at 5° C. is added 1-iodopyrrolidine-2,5-dione (68.80 g, 305.8 mmol) over 15 minutes. After 1 hour, a 10% solution of sodium thiosulfate (800 ml) is added. After stirring for 10 minutes, the organic phase is separated, washed with water, dried over Na$_2$SO$_4$, filtered and evaporated to dryness. The crude is purified by flash column chromatography on silica gel (0 to 50% EtOAc in Hexanes) to give tert-butyl (2S,4S)-2-(4,5-diiodo-1H-imidazol-2-yl)-4-methyl-pyrrolidine-1-carboxylate (52.3 g, 65.7%).

$^1$H NMR (400 MHz, dmso-d6, 2.5:1 mixture of rotamers), peaks for the major rotamer δ 12.70 (s, 1 H), 4.57 (dd, 1 H), 3.62-3.52 (m, 1 H), 2.95 (t, 1 H), 2.35-2.0 (m, 2 H), 1.50 (dd, 1 H), 1.10 (s, 9 H), 1.01 (d, 3 H).

tert-Butyl (2S,4R)-2-(4,5-diiodo-1H-imidazol-2-yl)-4-methyl-pyrrolidine-1-carboxylate (10.5 g, 13%) is also isolated $^1$H NMR (400 MHz, dmso-d6, 1.2:1 mixture of rotamers), peaks for the major rotamer, δ 12.65 (br s, 1 H), 4.69 (dd, 1 H), 3.69-3.50 (m, 1 H), 2.82 (t, 1 H), 2.45-2.3 (m, 1 H), 1.91-1.68 (m, 2 H), 1.15 (s, 9 H), 0.97 (d, J=6.6 Hz, 3 H). Selected peaks for the minor rotamer: 4.77 (d), 1.38 (s).

Step VI tert-Butyl (2S,4S)-2-(4-iodo-1H-imidazol-2-yl)-4-methyl-pyrrolidine-1-carboxylate A solution of LiCl in THF (3.9 mL of a 0.5 M solution, 1.99 mmol) is added to tert-butyl (2S,4S)-2-(4,5-diiodo-1H-imidazol-2-yl)-4-methyl-pyrrolidine-1-carboxylate (1 g, 1.99 mmol). After stirring for 5 minutes at rt the reaction mixture is cooled down to −20° C. and a solution of methyl magnesium chloride in THF (946.7 μL of 2.1 M, 1.99 mmol) is added dropwise. After stirring for 20 minutes at −20° C., a solution of isopropyl magnesium chloride in THF (3.2 mL of 1.24 M, 3.97 mmol) is added dropwise. The reaction mixture is slowly warmed up to rt and stirred for 2 hours. The reaction mixture is cooled down to 0° C. and a saturated aqueous NH$_4$Cl solution is slowly added followed by water. This mixture is then extracted with EtOAc (3×20 mL), and the combined organic layers are washed with brine, dried over Na$_2$SO$_4$, filtered and concentrated to dryness. The residue is purified by flash column chromatography on silica gel (0 to 25% EtOAC/Hexane) to afford tert-butyl (2S,4S)-2-(4-iodo-1H-imidazol-2-yl)-4-methyl-pyrrolidine-1-carboxylate (636 mg, 83%) as a white solid.

$^1$H NMR (400 MHz, dmso-d6, 2:1 mixture of rotamers), peaks for the major rotamer, δ 12.15 (s, 1 H), 7.19 (s, 1 H), 4.65-4.57 (m, 1 H), 3.65-3.55 (m, 1 H), 2.95 (t, 1 H), 2.4-2.1 (m, 2 H), 1.52 (dd, 1 H), 1.10 (s, 9 H), 1.00 (d, 3 H). Selected peaks for minor rotamer, 12.09 (s), 7.15 (s), 1.36 (s).

Step VII

4-Iodo-2-[(2S,4S)-4-methylpyrrolidin-2-yl]-1H-imidazole as a HCl salt

To a solution of tert-butyl (2S,4S)-2-(4-iodo-1H-imidazol-2-yl)-4-methyl-pyrrolidine-1-carboxylate (1.6 g, 4.242 mmol) in MeOH (16 mL) is added a 4M HCl in dioxane solution (16 ml) at 0° C. The reaction mixture is stirred at RT overnight and evaporated to dryness to afford 4-iodo-2-[(2S,4S)-4-methylpyrrolidin-2-yl]-1H-imidazole (1.37 g, 92.5%) as a yellow solid.

$^1$H NMR (400 MHz, dmso-d6) δ 9.98 (br s, 1 H), 9.17 (br s, 1 H), 7.46 (s, 1 H), 4.8-4.6 (m, 1 H), 3.45-3.35 (m, 1 H), 2.9-2.75 (m, 1 H), 2.5-2.3 (m, 2 H), 1.88-1.78 (m, 1 H), 1.09 (d, 3 H).

Step VIII

Methyl N-[(1S)-1-[(2S,4S)-2-(4-iodo-1H-imidazol-2-yl)-4-methyl-pyrrolidine-1-carbonyl]-2-methyl-propyl]carbamate To a solution of (2S)-2-(methoxycarbonylamino)-3-methyl-butanoic acid (644.5 mg, 3.68 mmol) in DMF (25 mL) at 0° C. is added HATU (1.4 g, 3.68 mmol), DIPEA (2.5 mL, 14.57 mmol) followed by 4-iodo-2-[(2S,4S)-4-methylpyrrolidin-2-yl]-1H-imidazole as HCl salt (1.28 g, 3.64 mmol). The reaction mixture is stirred at rt for 20 hours, diluted with EtOAc and H$_2$O. The organic phase is separated, washed with H$_2$O, dried over Na$_2$SO$_4$, filtered and concentrated to dryness. The residue is purified by flash column chromatography on silica gel (0 to 100% EtOAC/Hexane) to afford methyl N-[(1S)-1-[(2S,4S)-2-(4-iodo-1H-imidazol-2-yl)-4-methyl-pyrrolidine-1-carbonyl]-2-methyl-propyl]carbamate (1.3 g, 87.3%) as a white solid.

$^1$H NMR (400 MHz, dmso-d6) δ 12.03 (s, 1 H), 7.19 (d, 1 H), 7.18 (s, 1 H), 4.83 (dd, 1 H), 4.16-3.91 (m, 2 H), 3.52 (s, 3 H), 3.16 (t, 1 H), 2.38-2.08 (m, 2 H), 1.9-1.72 (m, 1 H), 1.72-1.61 (m, 1 H), 1.06 (d, 3 H), 0.76 (d, 3 H), 0.755 (m, 3 H).

121

Intermediate

Methyl N-[(1S)-1-[(2S,4S)-2-(5-iodo-1H-imidazol-2-yl)-4-methyl-pyrrolidine-1-carbonyl]-2-methyl-propyl]carbamate

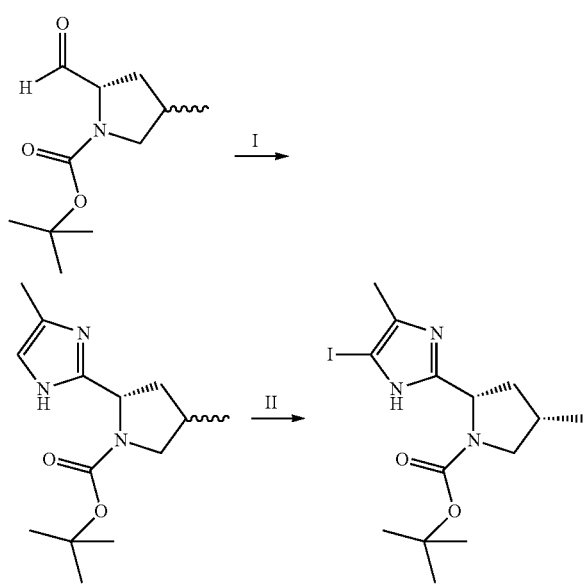

Step I tert-Butyl (2S)-4-methyl-2-(4-methyl-1H-imidazol-2-yl)pyrrolidine-1-carbo-xylate A stirred solution of tert-butyl (2S)-2-formyl-4-methyl-pyrrolidine-1-carboxylate (282 mg, 1.322 mmol) in MeOH (5.6 mL) is cooled to −20° C. and gaseous ammonia is bubbled for 10 minutes. 2-oxopropanal (35% w/w in water, 1.905 g, 9.254 mmol) is added and the reaction mixture is warmed to room temperature over one hour. The mixture is then heated to 65° C. for 1 hour, concentrated and 5 mL of water is added to the residue. The aqueous layer is extracted with $CH_2Cl_2$ (3×10 mL). The combined organic layers are dried over $Na_2SO_4$, filtered, and evaporated to dryness. The residue is purified by flash column chromatography on silica gel (0 to 20% MeOH in $CH_2Cl_2$) to afford tert-butyl (2S)-4-methyl-2-(4-methyl-1H-imidazol-2-yl)pyrrolidine-1-carbo-xylate (307 mg, 88%).

Step II tert-Butyl (2S,4S)-2-(5-iodo-4-methyl-1H-imidazol-2-yl)-4-methyl-pyrrolidine-1-carboxylate To a stirred solution of tert-butyl (2S)-4-methyl-2-(4-methyl-1H-imidazol-2-yl)pyrrolidine-1-carboxylate (307 mg, 1.013 mmol) in $CH_2Cl_2$ (15 mL) is added N-iodosuccinimide (240 mg, 1.013 mmol) at 5° C. The reaction mixture is stirred for one hour and water (2 mL) is added. The organic layer is separated, dried over $Na_2SO_4$, and evaporated to dryness. The residue is purified by flash column chromatography on silica gel (12 to 100% EtOAc in Hexanes) to give tert-butyl (2S,4S)-2-(5-iodo-4-methyl-1H-imidazol-2-yl)-4-methyl-pyrrolidine-1-carboxylate (246 mg, 62%).

122

Intermediate (S)-2-(5-Iodo-1H-benzoimidazol-2-yl)-pyrrolidine-1-carboxylic acid tert-butyl ester

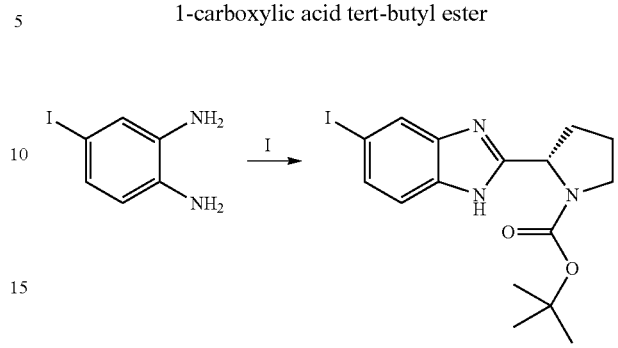

To a dry 1000 mL round bottom flask under Nitrogen, is added 4-iodo-benzene-1,2-diamine (45 g), (S)-pyrrolidine-1,2-dicarboxylic acid 1-tert-butyl ester (41.39 g) and THF (450 ml). The reaction mixture is stirred until complete dissolution then cooled to 0-2° C. DIPEA (50.17 ml) is added dropwise to control the exotherm then HATU (80.38 g) is added in one portion. The reaction mixture is stirred in an ice bath for 3 hours and followed by HPLC to monitor completion of reaction. To this solution are added 500 ml of water and 500 ml of ethyl acetate. The aqueous phase is extracted twice with ethyl acetate. The organic phases are combined and evaporated half. To the organic phase is added 450 ml of acetic acid and the mixture is evaporated to 300 ml. This procedure is repeated 3 times for a residual of ~470 ml, and the mixture is then heated at 50° C. over night. Toluene (200 ml) is added and evaporated to a small residue (repeated 6 times). To this solution is added 450 ml of ethyl acetate. The organic phase is washed with saturated sodium carbonate, dried over sodium sulfate, filtered and evaporated to dryness. The residue is purified on a pad of silica using 25% ethyl acetate/hexane mixture to give (S)-2-(5-Iodo-1H-benzoimidazol-2-yl)-pyrrolidine-1-carboxylic acid tert-butyl ester (67 g) as a beige powder.

$^1$H NMR (400 MHz, $CD_3OD$): δ [ppm] 8.0-7.7 (bs, 1 H), 7.5 (m, 1 H), 7.4-7.1 (bs, 1 H), 5.1-4.9 (m, 1 H), 3.8-3.6 (m, 1 H), 3.6-3.4 (m, 1 H), 2.6-2.2 (m, 1 H), 2.2-1.8 (m, 3 H), 1.4 (s, 3 H), 1.1 (s, 6 H)

LC/MS: m/z=413.95 (M+H$^+$).

Intermediates (2S,4S)-tert-Butyl 2-(5-iodo-1H-benzo[d]imidazol-2-yl)-4-methylpyrrolidine-1-carboxylate (1) and (2S,4R)-tert-butyl 2-(5-iodo-1H-benzo[d]imidazol-2-yl)-4-methylpyrrolidine-1-carboxylate (2)

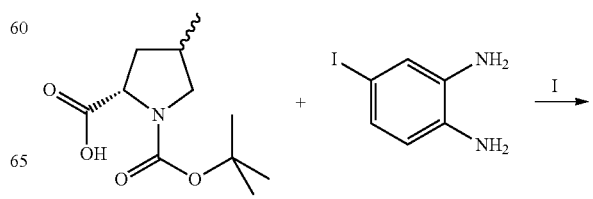

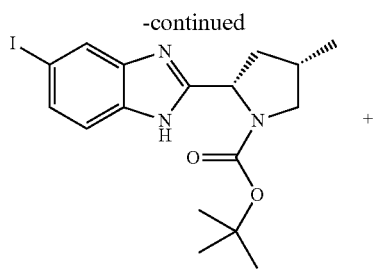

1

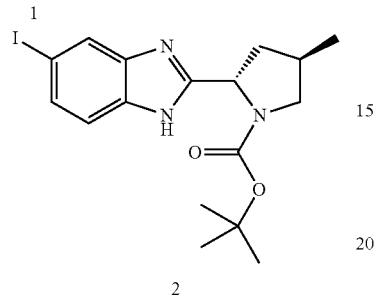

2

(2S)-1-tert-Butoxycarbonyl-4-methyl-pyrrolidine-2-carboxylic (880 mg, 3.83 mmol) acid, 4-iodobenzene-1,2-diamine(1.07, 4.60 mmol), HATU (1.75 g, 4.6 mmol) and 2,4,6-collidine (1.52 mL, 11.5 mmol) are added to 14 mL of DMF. The mixture is stirred at rt overnight. After removal of the solvent under vacuum, the residue is dissolved in 10 mL of AcOH, which is heated to 50° C. overnight. After removal of AcOH under vacuum, the residue is purified by silica gel chromatography 0-50% ethyl acetate/hexanes to provide trans compound 2 (2S,4R)-2-(5-iodo-1H-benzimidazol-2-yl)-4-methyl-pyrrolidine-1-carboxylate (260 mg, 15%). $^1$H NMR (400 MHz, CD$_3$OD) δ 7.85 (d, 1H), 7.49 (dt, 1H), 7.31 (d, 1H), 4.98 (m, 1H), 3.90 (m, 1H), 3.04 (dt, 1H), 2.48 (dd, 1H), 2.25-1.94 (m, 2H), 1.47 (d, 3H), 1.08 (s, 9H). Further elution gives cis compound 1 tert-butyl (2S,4S)-2-(5-iodo-1H-benzimidazol-2-yl)-4-methyl-pyrrolidine-1-carboxylate (1.38 g, 84%) $^1$H NMR (400 MHz, CD$_3$OD) δ 7.82 (d, 1H), 7.49 (m, 1H), 7.31 (d, 1H), 4.90 (m, 1H), 3.82 (m, 1H), 3.15 (t, 1H), 2.55 (m, 1H), 2.36 (m, 1H), 1.40 (d, 3H), 1.08 (s, 9H).

5-Iodo-2-((2S,4S)-4-methylpyrrolidin-2-yl)-1H-benzo[d]imidazole

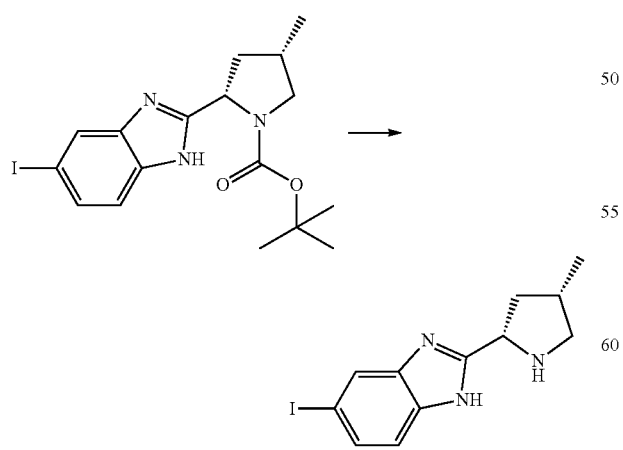

To a stirring solution of tert-butyl (2S,4S)-2-(5-iodo-1H-benzimidazol-2-yl)-4-methyl-pyrrolidine-1-carboxylate (3.70 g, 8.659 mmol) in dichloromethane (34 mL) is added TFA (17.22 mL, 223.5 mmol) and stirred at rt for 1 h. The reaction mixture is concentrated, azeotroped 2× with toluene and dried in vacuo. The residue is diluted with dichloromethane (200 mL), washed 2× with saturated sodium bicarbonate and brine and then dried over sodium sulfate. The organic is evaporated to give 5-iodo-2-[(2S,4S)-4-methylpyrrolidin-2-yl]-1H-benzimidazole (2.32 g, 82%).

Methyl (S)-1-((2S,4S)-2-(5-iodo-1H-benzo[d]imidazol-2-yl)-4-methylpyrrolidin-1-yl)-3-methyl-1-oxobutan-2-ylcarbamate

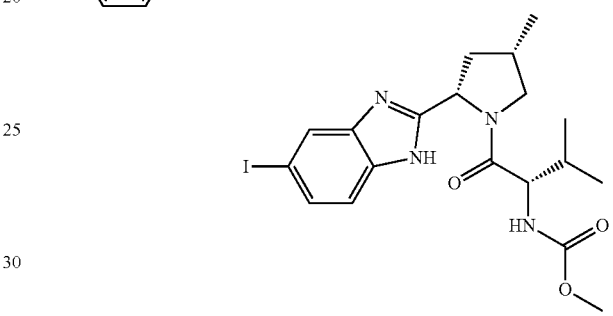

To 5-iodo-2-[(2S,4S)-4-methylpyrrolidin-2-yl]-1H-benzimidazole (2.29 g, 7.00 mmol) and (2S)-2-(methoxycarbonylamino)-3-methyl-butanoic acid (1.49 g, 7.70 mmol) in DMF is added HATU (3.46 g, 9.1 mmol) and DIPEA (2.4 mL, 14.0 mmol) at rt. The reaction mixture is stirred at rt overnight. To the reaction mixture is added water (350 mL) with fast stirring upon which a white solid precipitated out. The solid is suction filtered and dried under vacuum to give methyl N-[(1S)-1-[(2S,4S)-2-(5-iodo-1H-benzimidazol-2-yl)-4-methyl-pyrrolidine-1-carbonyl]-2-methyl-propyl]carbamate (2.73 g, 81%).

$^1$H NMR (400 MHz, CD$_3$OD) δ 7.83 (d, 1H), 7.49 (dd, 1H), 7.29 (d, 1H), 5.09 (dd, 1H), 4.31-4.15 (m, 2H), 3.59 (s, 6H), 2.54 (m, 1H), 2.43 (m, 1H), 2.00-1.90 (m, 2H), 1.18 (d, 3H), 0.95 (d, 3H), 0.82 (d, 3H).

LC/MS: m/z=485.0 (M+H$^+$).

Methyl (S)-1-((2S,4R)-2-(5-iodo-1H-benzo[d]imidazol-2-yl)-4-methylpyrrolidin-1-yl)-3-methyl-1-oxobutan-2-ylcarbamate

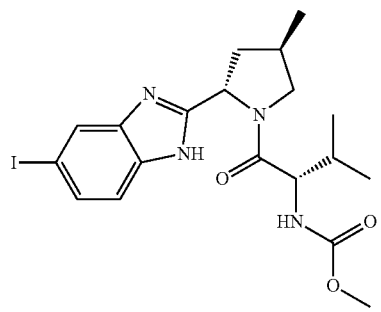 [SMILES: COC(=O)N[C@H](C(=O)N1C[C@H](C)C[C@H]1c1nc2cc(I)ccc2[nH]1)C(C)C]

¹H NMR (400 MHz, CD₃OD) δ 7.84 (d, 1H), 7.48 (dd, 1H), 7.30 (d, 1H), 5.29 (dd, 1H), 4.24-4.15 (m, 1H), 4.01 (dt, 1H), 3.66 (s, 3H), 3.57-3.46 (m, 1H), 2.80-2.69 (m, 1H), 2.25 (m, 1H), 2.01 (m, 2H), 1.17 (d, 3H), 0.91 (d, 3H), 0.88 (d, 3H).
LC/MS: m/z=485.0 (M+H⁺).

Intermediate

{(S)-1-[(S)-2-(5-Iodo-1H-benzoimidazol-2-yl)-pyrrolidine-1-carbonyl]-2-methyl-propyl}-carbamic acid methyl ester

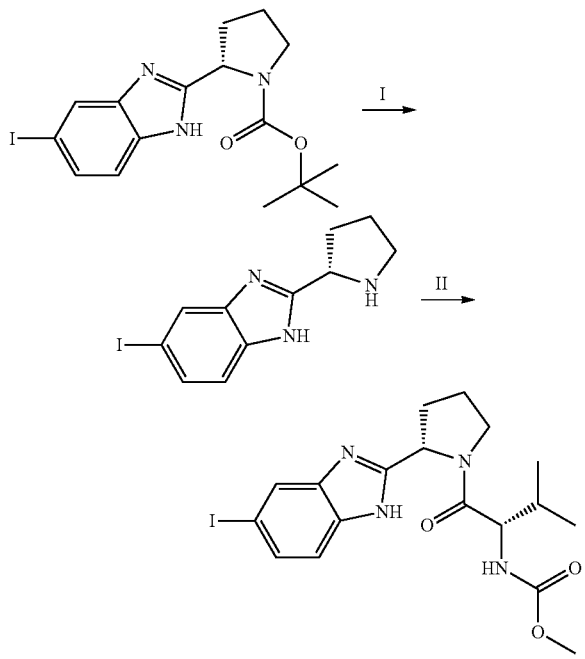

Step I (S)-5-Iodo-2-(pyrrolidin-2-yl)-1H-benzo[d]imidazole-TFA salt

To a stirring mixture of (S)-2-(5-Iodo-1H-benzoimidazol-2-yl)-pyrrolidine-1-carboxylic acid tert-butyl ester (20 g, 48 mmol) in CH₂Cl₂ (200 mL) at 0° C. is added TFA (200 mL). The reaction mixture is stirred at room temperature for 2 hours and concentrated in vacuum. The residue is dissolved in CH₂Cl₂ and saturated aqueous NaHCO₃, the organic layer is washed with saturated aqueous NaHCO₃, dried over sodium sulfate and concentrated in vacuum to afford (S)-5-iodo-2-(pyrrolidin-2-yl)-1H-benzo[d]imidazole-TFA salt (12 g).

¹H NMR (400 MHz, CDCl₃): δ [ppm] 8.40 (br s, 2H), 7.82 (s, 1H), 7.45 (d, 1H), 7.26 (d, 1H), 4.66 (t, 1H), 3.10 (m, 2H), 2.30 (m, 1H), 2.18 (m, 1H), 1.90 (m, 2H).

Step II

Methyl ((S)-1-((S)-2-(5-iodo-1H-benzo[d]imidazol-2-yl)pyrrolidin-1-yl)-3-methyl-1-oxobutan-2-yl)carbamate To a mixture of (S)-2-methoxycarbonylamino-3-methylbutyric acid (68 mg, 0.39 mmol) and (S)-5-iodo-2-(pyrrolidin-2-yl)-1H-benzo[d]imidazole-TFA salt (100 mg, 0.32 mmol) in anhydrous DMF (2 mL) is added DIPEA (0.25 mL, 1.43 mmol) followed by HATU (142 mg, 0.37 mmol). The reaction mixture is stirred for 4 hours at room temperature. Ice is added and the product is extracted with EtOAc. The combined organic layers are washed with brine, dried over sodium sulfate and concentrated in vacuum. The residue is purified by flash column chromatography on silica gel (EtOAc/MeOH 0% to 10%) to give methyl ((S)-1-((S)-2-(5-iodo-1H-benzo[d]imidazol-2-yl)pyrrolidin-1-yl)-3-methyl-1-oxobutan-2-yl)carbamate (150 mg).

¹H NMR (400 MHz, dmso-d6) 12.25 (d, 1H), 7.8 (d, 1H), 7.45-7.33 (m, 1H), 7.33-7.15 (m, 2), 5.1-5.2 (m, 1H), 3.9-3.7 (m, 2H), 3.5 (s, 3H), 2.25-2.05 (m, 2H), 2.05-1.8 (m, 3H), 0.8 (m, 7H)
LC/MS: m/z=470.90 (M+H⁺).
HPLC (Method C): $t_R$=7.78 min.

Intermediate

Methyl ((S)-3-methyl-1-oxo-1-((S)-2-(5-(4,4,5,5-tetramethyl-1,3,2-dioxaborolan-2-yl)-1H-benzo[d]imidazol-2-yl)pyrrolidin-1-yl)butan-2-yl)carbamate

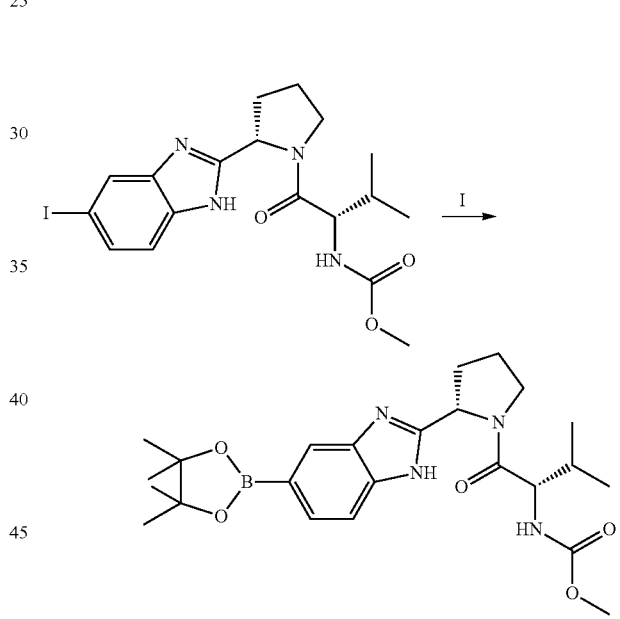

Methyl ((S)-1-((S)-2-(5-iodo-1H-benzo[d]imidazol-2-yl)pyrrolidin-1-yl)-3-methyl-1-oxobutan-2-yl)carbamate (2.23 g, 4.74 mmol), 4,4,4',4',5,5,5',5'-octamethyl-2,2';bi(1,3,2-dioxaborolane (3.61 g, 14.22 mmol), PdCl₂dppf (193 mg), and potassium acetate (1.53 g, 15.64 mmol) are added to dry DMF (40 mL). The mixture is purged twice with nitrogen and is stirred overnight at 85° C. After removal of the solvent under reduced pressure, the residue is purified on flash chromatography on silica gel (methanol/CH₂Cl₂, 0 to 5%) to give methyl ((S)-3-methyl-1-oxo-1-((S)-2-(5-(4,4,5,5-tetramethyl-1,3,2-dioxaborolan-2-yl)-1H-benzo[d]imidazol-2-yl)pyrrolidin-1-yl)butan-2-yl)carbamate (1.5 g).

¹H NMR (400 MHz, CDCl₃): δ [ppm] 7.60-7.95 (m, 3H), 5.82 (m, 1H), 5.42 (m, 1H), 4.29 (m, 1H), 3.63-3.75 (m, 6H), 3.04 (m, 1H), 1.91-2.40 (m, 5H), 1.26-1.34 (m, 12H), 0.79-1.03 (m, 6H).
LC/MS: m/z 471.19 (M+H⁺).

Compounds 1-3, 11, 14, 15, and 17-57

Compounds 1-3, 11, 14, 15, and 17-57 as disclosed in Tables 1A and 1B were prepared according to the procedures outlined in Examples 1-12 using the appropriate intermediate starting materials.

Example 13

Activity Determination Using the ELISA and the Sub-Genomic Replicon 1a Cell Line The cell line W11.8 containing the sub-genomic HCV replicon of genotype 1a is used to determine the potency of the drugs. The RNA replication in presence of different drug concentrations is indirectly measured in this cell line by the level of NS5A protein content upon drug treatment for four days. It is shown that the level of the NS5A protein correlates well with the level of HCV RNA in the replicon cell line. Cells are split twice a week in order to keep the confluence state below 85% of the culture flask surface area. The culture media used for cell passaging consists of DMEM-10% foetal bovine serum with 100 UI/mL penicillin, 100 µg/mL streptomycin, 2 mM glutamine, 1 mM sodium pyruvate, non-essential amino acids (1×) and 600 µg/mL of G418 final concentrations. Monolayer of the W11.8 cells is trypsinized and cells are counted. Cells are diluted at 50,000 cells/mL with complete DMEM without G418, then approximately 5,000 viable cells (100 µL) are plated per well in a white opaque 96-well microtiter plate. After an incubation period of 2-4 hours at 37° C. in a 5% CO2 incubator, compounds are added at various concentrations. Drugs are resuspended in DMSO at a stock concentration of 10 mM. Then, drugs are serially diluted at twice the final concentration in the same medium. One volume (100 µL) of each drug dilution is then added to each well that contains cells. A control compound is used as an internal standard for each plate assay. Sixteen wells are used as control (0% inhibition) without drug. Eight wells are used as background control (100% inhibition) containing 2 µM (final concentration) of the control drug that was shown to inhibit the NS5A expression at≈100% and is nontoxic to the cells. Values from 100% inhibited wells were averaged and used as the background value. Cells are further incubated for four days at 37° C. in a 5% $CO_2$ incubator. Following the incubation time of four days, the media is removed and wells are washed once with 150 µL of PBS at room temperature for five minutes. Cells are then fixed for five minutes using 150 µL per well of cold (−20° C.) fixative solution (50% methanol/50% acetone mix). Cells are then washed twice with 150 µL of PBS (phosphate buffered saline) per well, following the addition of 150 µL of blocking solution, cells are incubated for one hour at 37° C. to block non-specific sites. The blocking solution is removed and cells are washed twice with 150 µL of PBS per well and once with 150 µL of PBSTS solution (PBS/0.1% Triton X-100/0.02% SDS) per well. Then, 50 µL of mouse monoclonal anti-NS5A antibody (Santa Cruz, Cat. No. sc-52417) is added in each well, diluted 1/1,000 in the blocking solution and incubated at 4° C. overnight. Next day, media is removed and plates are washed five times with 150 µL of PBS per well with five-minute incubations at room temperature. Then 50 µL per well of peroxidase-conjugated donkey anti-mouse antibody (Jackson Immunoresearch, Cat. No. 715-036-150) diluted 1/10,000 in the blocking solution is added and incubated at room temperature for three hours on a shaker (500 rpm). Plates are washed four times with 150 µL of PBSTS solution per well and once with 150 µL of PBS. Then, substrate solution (100 µl, SuperSignal ELISA Pico Chemiluminescent Substrate, Fisher Cat. No. 37069) is added in each well and plates are incubated 60 minutes at room temperature prior to reading the luminescence (relative light units) on the Analyst HT plate reader. The percentage of inhibition at each drug concentration tested (in duplicate) is calculated. The concentration required to reduce viral replication by 50% ($IC_{50}$) is then determined from dose response curves using nonlinear regression analysis with the GraphPad Prism software, version 2.0 (GraphPad Software Inc., San Diego, Calif., USA).

Example 14

Cell-Based Luciferase Reporter HCV (Ib) RNA Replication Assay Cell Culture

Replicon cell lines Huh-5.2 are derived from the Huh-7 hepatocarcinoma cell line are maintained in culture as generally described in Krieger, N; Lohmann, V; Bartenschlager, R. Enhancement of hepatitis C virus RNA replication by cell culture-adaptive mutations. *J. Virol.* 2001, 75, 4614-4624. The Huh-5.2 cells contain the highly cell culture-adapted replicon $I_{389}$luc-ubi-neo/NS3-375.1 construct that carries, in addition to the neomycin gene, an integrated copy to the firefly luciferase gene (Krieger, N; Lohmann, V; Bartenschlager, R. Enhancement of hepatitis C virus RNA replication by cell culture-adaptive mutations. *J. Virol.* 2001, 75, 4614-4624). This cell line allows measurement of HCV RNA replication and translation by measuring luciferase activity. It has been previously shown that the luciferase activity tightly follows the replicon RNA level in these cells (Krieger, N; Lohmann, V; Bartenschlager, R. Enhancement of hepatitis C virus RNA replication by cell culture-adaptive mutations. *J. Virol.* 2001, 75, 4614-4624). The Huh-ET cell line has the same features as those mentioned for Huh-5.2 cell line, except that ET cells are more robust and contain an adaptative mutation in the HCV NS4B gene instead of NS5A. Both cell lines are maintained in cultures at a sub-confluent level (<85%) as the level of replicon RNA is highest in actively proliferating cells. The culture media used for cell passaging consist of DMEM (Gibco BRL Laboratories, Mississauga, ON, Canada) supplemented with 10% foetal bovine serum with 1% penicilin/streptomycin, 1% glutamine, 1% sodium pyruvate, 1% non-essential amino acids, and 180 µg/ml of G418 final concentration. Cells are incubated at 37° C., in an atmosphere of 5% $CO_2$ and passaged twice a week to maintain sub-confluence.

Approximately 3000 viable Huh-ET cells (100 µl) are plated per well in a white opaque 96-well microtiter plate. The cell culture media used for the assay is the same as described above except that it contains no G418 and no phenol red. After an incubation period of 3-4 hours at 37° C. in a 5% $CO_2$ incubator, compounds (100 µl) are added at various concentrations. Cells are then further incubated for 4 days at 37° C. in a 5% $CO_2$ incubator. Thereafter, the culture media is removed and cells are lysed by the addition of 95 µL of the luciferase buffer (luciferin substrate in buffered detergent). Cell lysates are incubated at room temperature and protected from direct light for at least 10 minutes. Plates are read for luciferase counts using a luminometer (Wallac MicroBeta Trilux, Perkin Elmer™, MA, USA).

HCV 1a and 1b are the two most prevalent HCV genotypes and the most difficult to treat. It has proven problematic in the past to find compounds having good activity against both genotypes. However, the compounds of the present invention, particularly those with a 4-methylpyrrolidine group, are active against both HCV 1a and 1b genotypes. The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The 50% inhibitory concentrations ($IC_{50}$s) for inhibitory effect are determined from dose response curves using eleven concentrations per compound in duplicate. Curves are fitted to data points using nonlinear regression analysis, and $IC_{50}$s are interpolated from the resulting curve using GraphPad Prism software, version 2.0 (GraphPad Software Inc., San Diego, Calif., USA).

Table 2 shows compounds representative of the present invention.

TABLE 2

| # | M + 1 (Obs) | RT (min) | 1H-NMR | EC50_1b (uM) |
|---|---|---|---|---|
| 1 | | | | ++ |
| 2 | | | | ++ |
| 3 | 713.6 | 6.9 | | +++ |
| 4 | 789.6 | 7.81 | | +++ |
| 5 | 817.7 | 8.41 | | +++ |
| 6 | 845.06 | 9.23 | | +++ |
| 7 | 831.67 | 8.77 | | +++ |
| 8 | 831.61 | 8.72 | | +++ |
| 9 | 765.5 | 8.11 | | +++ |
| 10 | 793.38 | 9.04 | | +++ |
| 11 | 831.85 | 2.5 | | +++ |
| 12 | 765.53 | 7.91 | | +++ |
| 13 | 817.5 | 8.62 | | +++ |
| 14 | 823.68 | 2.56 | H NMR (300.0 MHz, Acetone) d 11.45-11.13 (m, 2H), 7.98-7.21 (m, 8H), 6.28-6.19 (m, 2H), 5.36-5.22 (m, 1H), 5.18-5.12 (m, 1H), 3.60 (s, 3H), 3.24 (s, 3H), 2.83 (s, 2H), 1.17 (m, 14H) and 1.00-0.80 (m, 18H) ppm | +++ |
| 15 | 831.46 | 8.26 | | +++ |
| 16 | 803.34 | 8.16 | | +++ |
| 17 | 845.58 | 8.94 | | +++ |
| 18 | 817.62 | 8.43 | | +++ |
| 19 | 817.32 | 8.18 | | +++ |
| 20 | 791.37 | 7.7 | | +++ |
| 21 | 833.68 | 7.89 | | |
| 22 | 831.9 | 2.65 | H NMR (300.0 MHz, Acetone) d 11.04 (s, 1H), 8.20-7.29 (m, 12H), 6.28 (d, J = 8.6 Hz, 2H), 5.35-5.29 (m, 1H), 5.17-5.12 (m, 1H), 4.32-4.20 (m, 3H), 4.01 (s, 3H), 3.69 (s, 1H), 3.61 (s, 6H), 3.44 (t, J = 10.2 Hz, 1H), 3.28-3.19 (m, 1H), 2.66-2.57 (m, 1H), 2.51-2.38 (m, 3H), 2.07-1.83 (m, 4H), 1.40 (m, 3H), 1.22-1.15 (m, 6H) and 0.96-0.66 (m, 9H) ppm | |
| 23 | 845.6 [1] | | | +++ |
| 24 | 829.66 [1] | | | +++ |
| 25 | 879.78 [1], 880.1 [2] | | | +++ |
| 26 | 879.72 [1] | | | +++ |
| 27 | 823.47 [1] | | | +++ |
| 28 | 831.9 [1] | | | +++ |
| 29 | 789.35 [1] | | | +++ |
| 30 | 861.3 [1] | | | +++ |
| 31 | 845.49 [1] | | | +++ |
| 32 | 835.5 [1] | | | +++ |
| 33 | 797.43 [1] | | | +++ |
| 34 | 792.5 [1], 792.58 [2] | | | +++ |
| 35 | 831.65 [1] | | | +++ |
| 36 | 689.4 [1] | | | |
| 37 | 489.05 [1], 489.17 [2] | | | |
| 38 | 831.37 [1] | | | +++ |
| 39 | 835.6 [1] | | | +++ |
| 40 | 815.51 [1] | | | +++ |
| 41 | 797.44 [1] | | | +++ |
| 42 | 781.47 [1] | | | ++ |
| 43 | 803.57 [1] | | | +++ |
| 44 | 827.49 [1] | | | +++ |
| 45 | 827.42 [1] | | | +++ |
| 46 | 817.01 [1] | | | +++ |
| 47 | 817.84 [1] | | | +++ |
| 48 | 817.51 [1] | | | +++ |
| 49 | 503.29 [1], 503.29 [2] | | | |
| 50 | 703.65 [1] | | | |

TABLE 2-continued

| # | M + 1 (Obs) | RT (min) | 1H-NMR | EC50_1b (uM) |
|---|---|---|---|---|
| 51 | 660.7 [1], 660.66 [2], 660.62 [3] | | | +++ |
| 52 | 821.7 [1], 821.8 [2] | | | +++ |
| 53 | 760.75 [1] | | | |
| 54 | 817.74 [1] | | | +++ |
| 55 | 916.78 [1] | | | +++ |
| 56 | 916.65 [1] | | | +++ |
| 57 | 660.58 [1] | | | | uM: +++ <= 0.005 < ++ <= 5.0 < +

Table 3 shows comparative data for exemplary compounds of formula (I). As is shown in the table, the compounds having a substituent at the 4-position of the pyrrolidine ring (i.e. compounds of the invention where $R_4$ and $R_{4'}$ are methyl). Data shows $IC_{50}$ values against the sub-genomic replicon 1a and 1b cell lines.

TABLE 3

| Entry | Comp. | Structure | IC$_{50}$ (pM) (1a) | IC$_{50}$ (pM) (1b) |
|---|---|---|---|---|
| 1 | 5 | 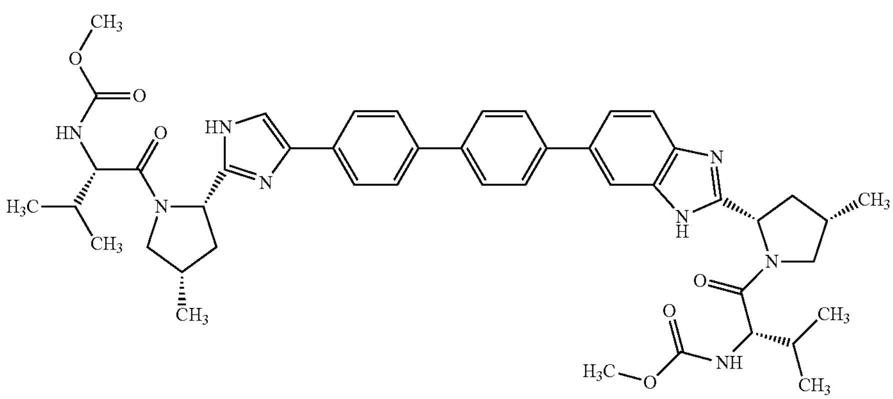 [SMILES: COC(=O)N[C@H](C(=O)N1C[C@@H](C)C[C@H]1c1nc(-c2ccc(-c3ccc(-c4ccc5nc([C@@H]6C[C@H](C)CN6C(=O)[C@@H](NC(=O)OC)C(C)C)[nH]c5c4)cc3)cc2)c[nH]1)C(C)C] | 4.1 | 5 |
| 2 | 18 | 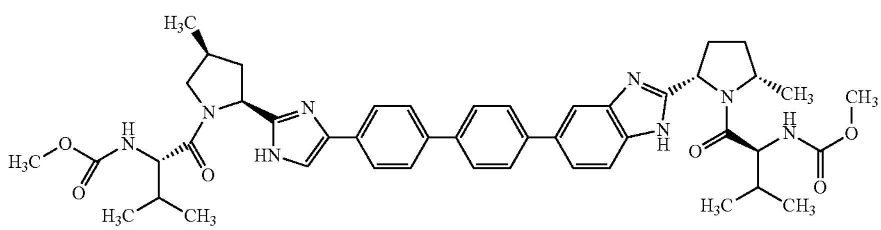 | 8.5 | 8.5 |
| 3 | 13 | 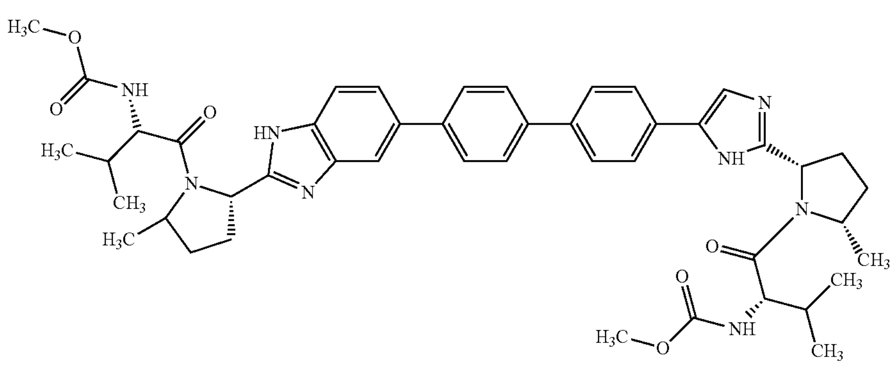 | 36 | 2.6 |

TABLE 3-continued

| Entry | Comp. | Structure | IC$_{50}$ (pM) (1a) | IC$_{50}$ (pM) (1b) |
|---|---|---|---|---|
| 4 | 4 | 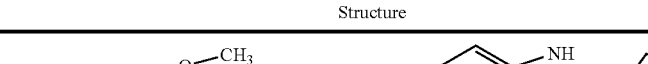 | 140 | 13 |

The invention claimed is:

1. A compound of formula (IIIA):

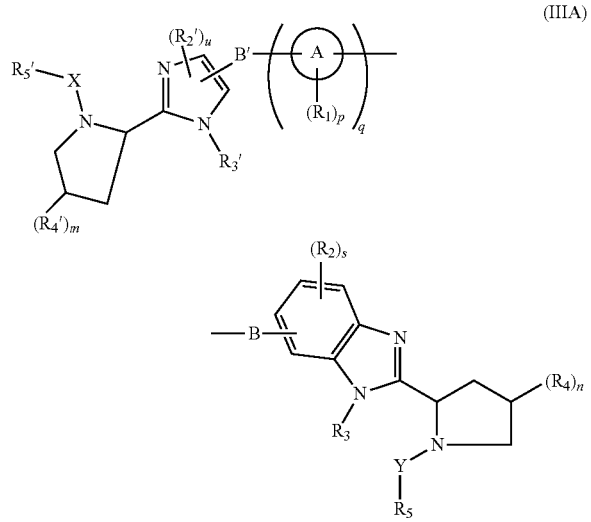

(IIIA)

or a pharmaceutically acceptable salt thereof, wherein
each A is independently $C_{6-14}$ aryl, 4-12 membered heterocycle, $C_{3-10}$ cycloalkyl, or 5-12 membered heteroaryl;
B and B' are each independently absent, $C_{1-6}$ alkyl, $C_{2-6}$ alkenyl, or $C_{2-6}$ alkynyl;
$R_1$ is halogen, $-OR_a$, $-NR_aR_b$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, $-P(=O)OR_aOR_b$, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, or any two occurrences of $R_1$ can be taken together with the atoms to which they are attached to form a 5-7 cycloalkyl which is unsubstituted or substituted one or more times by $R^{11}$ or a 5-7 membered heterocycle which is unsubstituted or substituted one or more times by $R^{12}$;

$R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;
$R_{2'}$ is halogen, $C_{1-10}$ alkyl, $C_{1-6}$ halogenated alkyl, $-(CH_2)_{1-6}OH$, $-NR_bC(=O)R_a$, $C_{6-12}$ aryl, or 5-12 membered heteroaryl;
each $R_2$ is independently halogen, $C_{1-10}$ alkyl, $C_{1-6}$ halogenated alkyl, $-(CH_2)_{1-6}OH$, $-OR_a$, $-C(=O)OR_a$, $-NR_aR_b$, $-NR_bC(=O)R_a$, $-C(O)NR_aR_b$, $-S(O)_{0-3}R_a$, $C_{6-12}$ aryl, 5-12 membered heterocycle, or 5-12 membered heteroaryl;
$R_3$ and $R_3'$ are each independently H, $C_{1-6}$ alkyl, $-(CH_2)_{1-6}OH$, $C_{2-6}$ alkenyl, or $C_{2-6}$ alkynyl;
$R_4$ and $R_4'$ are each independently $C_{1-6}$ alkyl,
X and Y are each independently

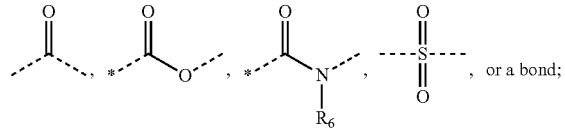, or a bond;

wherein the asterisk (*) indicates the point of attachment to the nitrogen of pyrrolidine ring;
$R_5$ and $R_5'$ are each independently H, $C_{1-18}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;
$R_6$ is H, $C_{1-6}$ alkyl, or halogenated $C_{1-6}$ alkyl;
m and n are each independently 1, or 2;
p is 0, 1, 2, 3 or 4;
q is 0, 1 or 2;
u is 0 or 1;
s is 0, 1, 2, 3 or 4;

$R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —P(=O)$OR_aOR_b$;

$R^{11}$ is halogen, —$OR_a$, —$NR_aR_b$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and $R^{12}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

2. The compound according claim 1, wherein
each A is independently cyclopropyl, cyclohexyl, pyrrolidinyl, pyrazolidinyl, imidazolidinyl, piperazinyl, piperadinyl, phenyl, naphthalenyl, thienyl, furanyl, pyrrolyl, pyrazolyl, imidazolyl, thiazolyl, thiadiazolyl, oxazolyl, oxadiazolyl, pyridyl, pyrimidyl, pyrazinyl, pyridazinyl, indolyl, indazolyl, benzimidazolyl, benzoxazolyl, benzodioxolyl, benzothiazolyl, benzothiadiazolyl, dihydrobenzodioxine, thienofuranyl, thienothienyl, thienopyrrolyl, quinolinyl, quinoxalinyl, quinazolinyl, cinnolinyl, or triazolyl; and wherein each A is independently substituted with $(R_1)_p$.

3. The compound according to claim 2, wherein each A is independently piperazinyl, piperadinyl, thienyl, furanyl, pyrrolyl, pyrazolyl, imidazolyl, thiazolyl, oxazolyl, thiadiazolyl, pyrrolidinyl, pyridyl, pyrimidinyl, pyrazinyl, pyridazinyl, benzoxazolyl, benzodioxolyl, benzothiazolyl, benzothiadiazolyl, dihydrobenzodioxinyl, thienofuranyl, thienothienyl, quinolinyl, or triazolyl.

4. The compound according to claim 1, wherein B and B' are independently absent, $C_{1-6}$ alkyl or $C_{2-6}$ alkynyl.

5. The compound according to claim 1, wherein

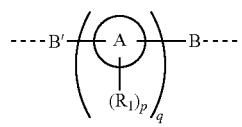

is selected from the group consisting of:

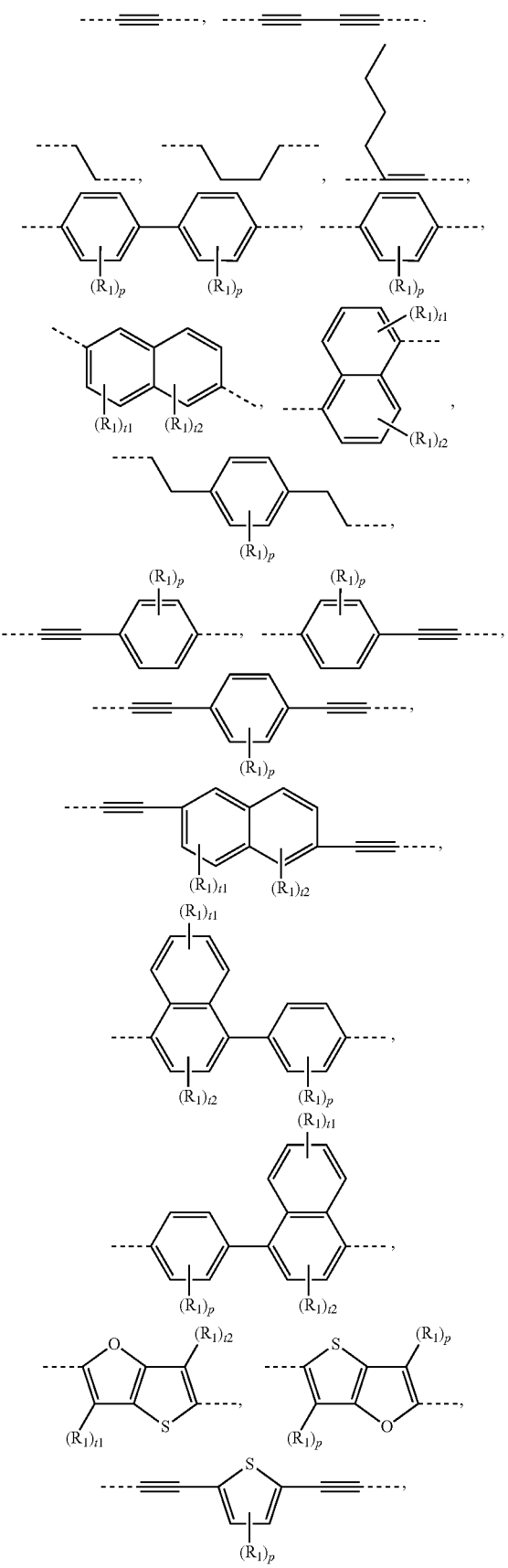

-continued
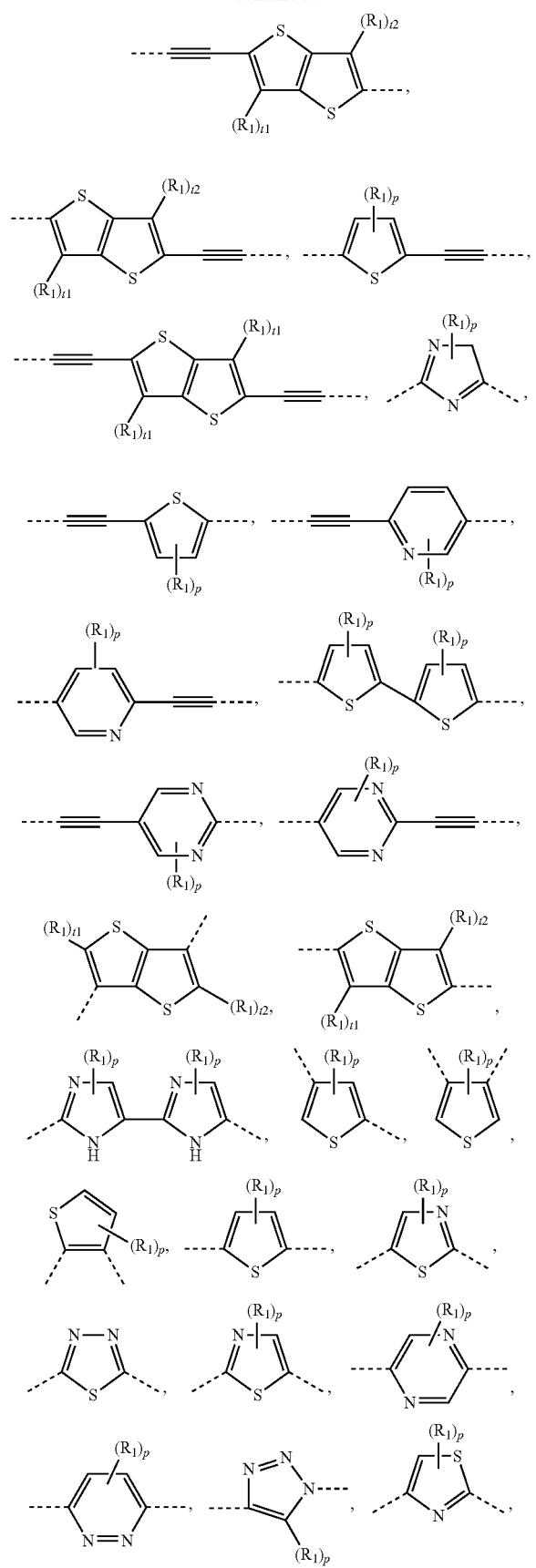
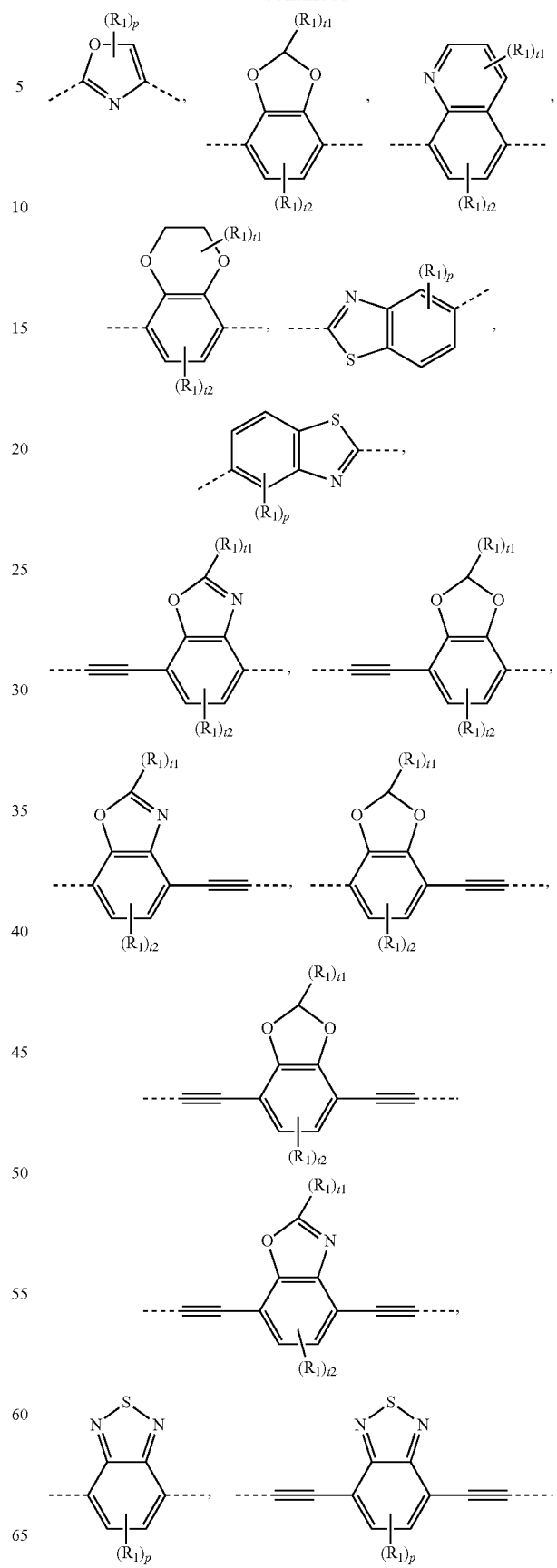

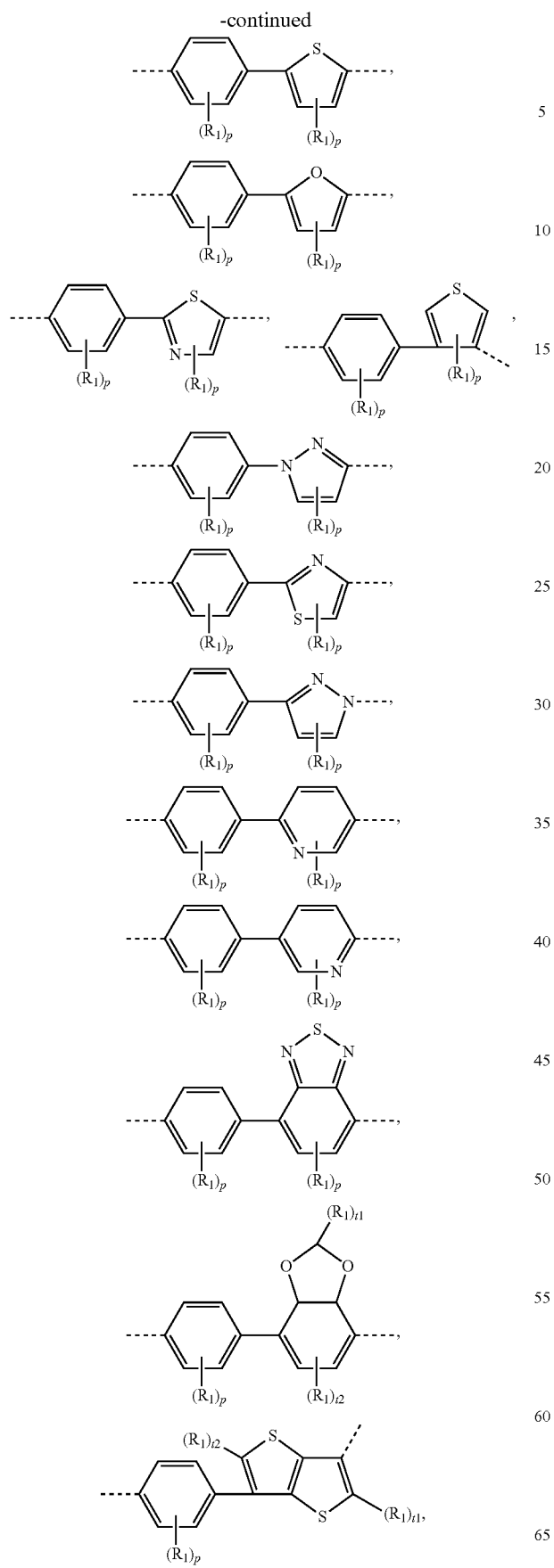
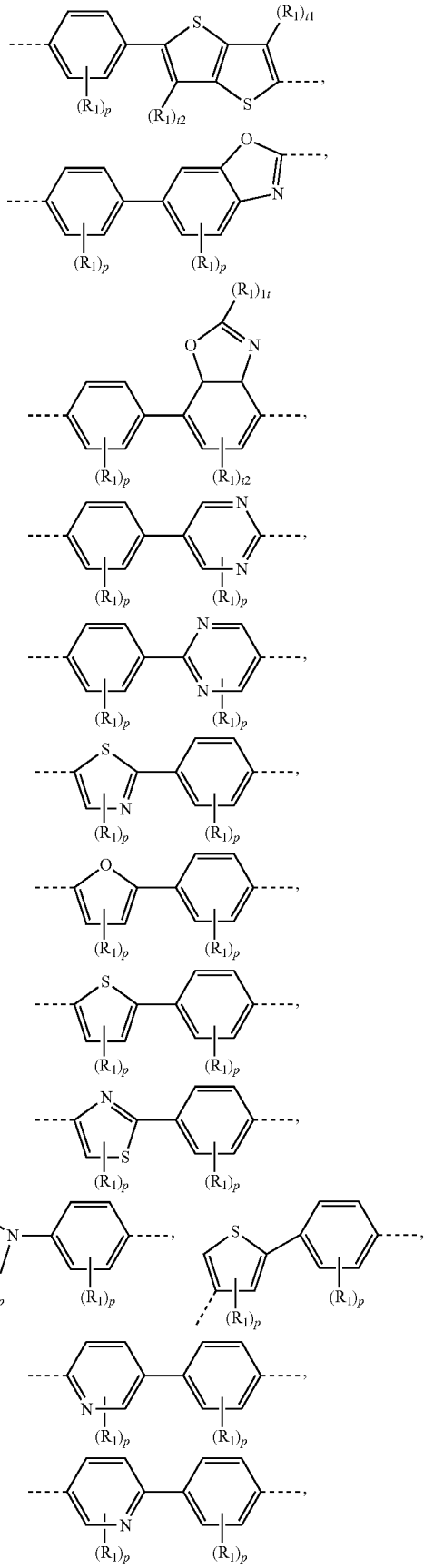

-continued

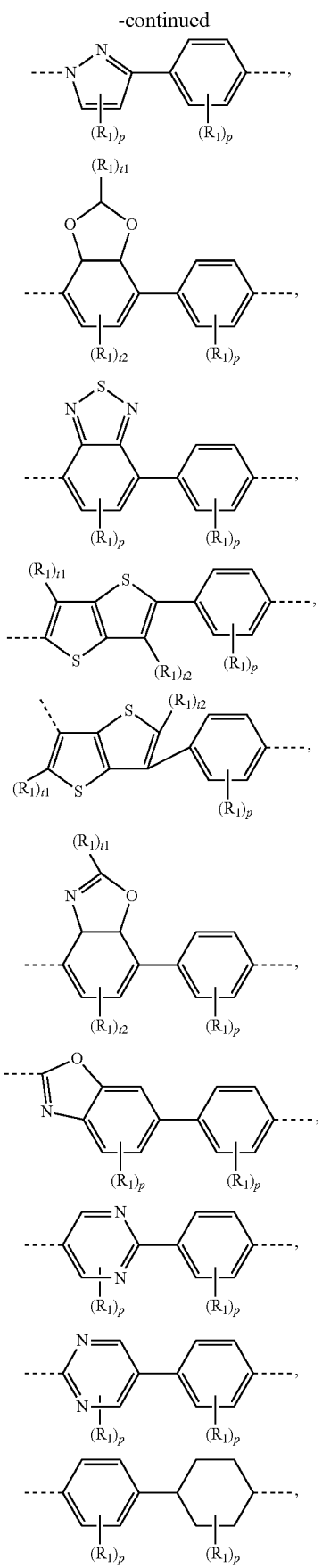

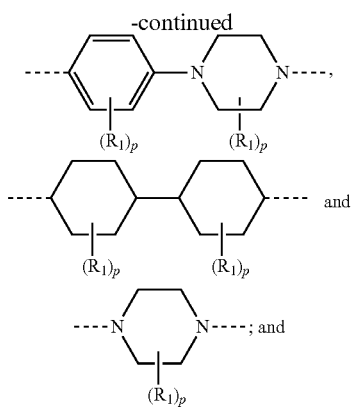

t1 + t2 = p.

6. The compound according to claim 1, wherein $R_1$ is halogen, $C_{1-4}$ alkyl which is unsubstituted or substituted one or more times by $R^{10}$, —C(=O)$OR_a$, —C(O)$NR_aR_b$, hydroxyl, cyano, or $C_{1-3}$ alkoxy.

7. The compound according to claim 1, wherein $R_2'$ is methyl, trifluoromethyl, iodo, $CH_2OH$, or $NHC(O)CH_3$.

8. The compound according to claim 7, wherein u is 0.

9. The compound according to claim 1, wherein each $R_2$ is independently fluoro or methyl.

10. The compound according to claims 9, wherein s is 0.

11. The compound according to claim 1, wherein $R_3$ and $R_3'$ are H or methyl.

12. The compound according to claim 11, wherein $R_4$ and $R_4'$ are methyl.

13. The compound according to claim 1, wherein one of m and n is 1, and the other is 0.

14. The compound according to claim 1, wherein X and Y are

15. The compound according to claim 1, wherein $R_5$ and $R_5'$ are each independently, $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, $C_{7-8}$ aralkyl which is unsubstituted or substituted one or more times by $R^{11}$, 5-6 membered heteroaryl which is unsubstituted or substituted one or more times by $R^{11}$, 6-8 membered heteroaralkyl which is unsubstituted or substituted one or more times by $R^{11}$, 3-6 membered heterocycle which is unsubstituted or substituted one or more times by $R^{12}$, or 4-8 membered heterocycle-alkyl which is unsubstituted or substituted one or more times by $R^{12}$.

16. The compound according to claim 1, wherein $R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$R_a$, hydroxyl, nitro, azido, cyano, —S(O)$_{0-3}R_a$, —SO$_2NR_aR_b$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

17. The compound according to claim 1, wherein $R_a$-$R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

18. The compound according to claim 1, wherein said compound is of formula (IV):

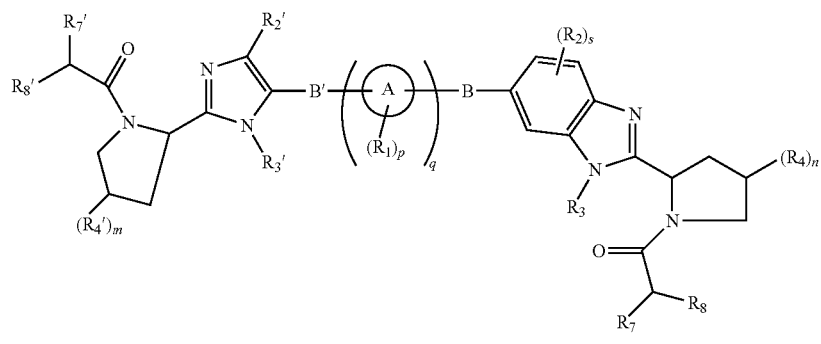

(IV)

or a pharmaceutically acceptable salt thereof wherein
- $R_7$ and $R_7'$ are each independently $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 3-6 membered heterocycle which is unsubstituted or substituted one or more times by $R^{12}$, or 4-7 membered heterocycle-alkyl which is unsubstituted or substituted one or more times by $R^{12}$;
- $R_8$ and $R_8'$ are each independently —$NR_aR_b$, —$NR_aC(=O)NR_aR_b$, —$NR_bC(=O)R_a$, —$NR_dC(=NR_c)NR_aR_b$, —$NR_bC(=O)OR_a$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

19. The compound according to claim 1 wherein said compound is of formula (V):

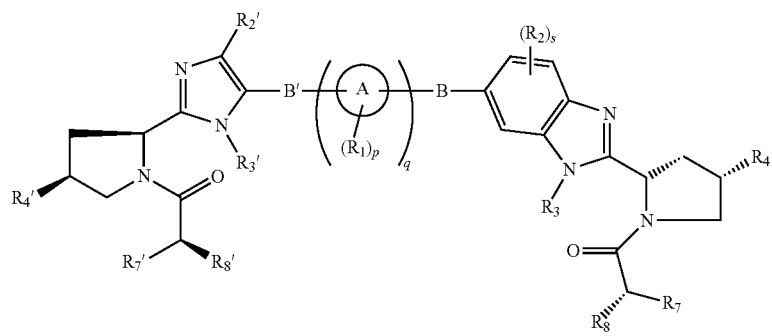

(V)

or a pharmaceutically acceptable salt thereof.

20. A compound of formula (VI):

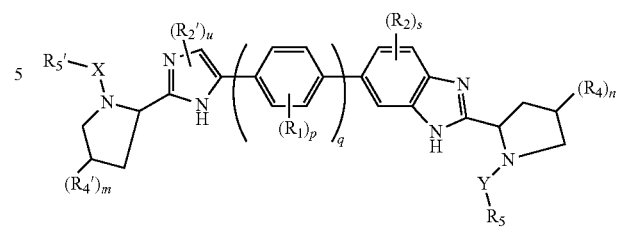

(VI)

or a pharmaceutically acceptable salt thereof, wherein
- $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;
- $R_1$ is halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, —$P(=O)OR_aOR_b$, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, or any two occurrences of $R_1$ can be taken together with the atoms to which they are attached to form a 5-7 cycloalkyl which is unsubstituted or substituted one or more times by $R^{11}$ or a 5-7 membered heterocycle which is unsubstituted or substituted one or more times by $R^{12}$;

$R_{2'}$ is halogen, $C_{1-10}$ alkyl, $C_{1-6}$ halogenated alkyl, —(CH$_2$)$_{1-6}$OH, —NR$_b$C(=O)R$_a$, $C_{6-12}$ aryl, or 5-12 membered heteroaryl;

each R$_2$ is independently halogen, $C_{1-10}$ alkyl, $C_{1-6}$ halogenated alkyl, —(CH$_2$)$_{1-6}$OH, —OR$_a$, —C(=O)OR$_a$, —NR$_a$R$_b$, —NR$_b$C(=O)R$_a$, —C(O)NR$_a$R$_b$, —S(O)$_{0-3}$R$_a$, $C_{6-12}$ aryl, 5-12 membered heterocycle, or 5-12 membered heteroaryl;

R$_4$ and R$_4'$ are each independently $C_{1-6}$ alkyl;

X and Y are each independently

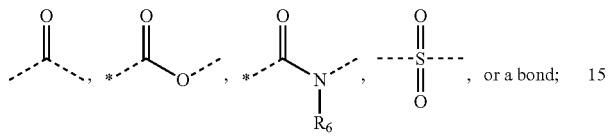

, or a bond;

wherein the asterisk (*) indicates the point of attachment to the nitrogen of the pyrrolidine ring;

R$_5$ and R$_5'$ are each independently H, $C_{1-18}$ alkyl which is unsubstituted or substituted one or more times by R$^{10}$, $C_{2-12}$ alkenyl which is unsubstituted or substituted one or more times by R$^{10}$, $C_{2-12}$ alkynyl which is unsubstituted or substituted one or more times by R$^{10}$, $C_{6-14}$ aryl which is unsubstituted or substituted one or more times by R$^{11}$, $C_{7-16}$ aralkyl which is unsubstituted or substituted one or more times by R$^{11}$, 5-12 membered heteroaryl which is unsubstituted or substituted one or more times by R$^{11}$, 6-18 membered heteroaralkyl which is unsubstituted or substituted one or more times by R$^{11}$, 3-12 membered heterocycle which is unsubstituted or substituted one or more times by R$^{12}$, or 4-18 membered heterocycle-alkyl which is unsubstituted or substituted one or more times by R$^{12}$;

R$_6$ is H, $C_{1-6}$ alkyl, or halogenated $C_{1-6}$ alkyl;

m and n are each independently 1 or 2;

p is 0, 1, 2, 3 or 4;

q is 1 or 2;

u is 0 or 1;

s is 0, 1, 2, 3 or 4;

$R^{10}$ is halogen, —OR$_a$, oxo, —NR$_a$R$_b$, =NO—R$_c$, —C(=O)OR$_a$, —C(O)NR$_a$R$_b$, —C(=O)OH, —C(=O)R$_a$, —C(=NOR$_c$)R$_a$, —C(=NR$_c$)NR$_a$R$_b$, —NR$_a$C(=O)NR$_a$R$_b$, —NR$_b$C(=O)R$_a$, —NR$_a$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$;

$R^{11}$ is halogen, —OR$_a$, —NR$_a$R$_b$, —C(=O)OR$_a$, —C(O)NR$_a$R$_b$, —C(=O)OH, —C(=O)R$_a$, —C(=NOR$_c$)R$_a$, —C(=NR$_c$)NR$_a$R$_b$, —NR$_a$C(=O)NR$_a$R$_b$, —NR$_b$C(=O)R$_a$, —NR$_a$C(=NR$_c$)NR$_a$R$_b$, —NR$_b$C(=O)OR$_a$, —OC(=O)NR$_a$R$_b$, —O(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and $R^{12}$ is halogen, —OR$_a$, oxo, —NR$_a$R$_b$, =NO—R$_c$, —C(=O)OR$_a$, —C(O)NR$_a$R$_b$, —C(=O)OH, —C(=O)R$_a$, —C(=NOR$_c$)R$_a$, —C(=NR$_c$)NR$_a$R$_b$, —NR$_a$C(=O)NR$_a$R$_b$, —NR$_b$C(=O)R$_a$, —NR$_a$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

21. The compound according to claim 20, wherein said compound is of formula (VIA):

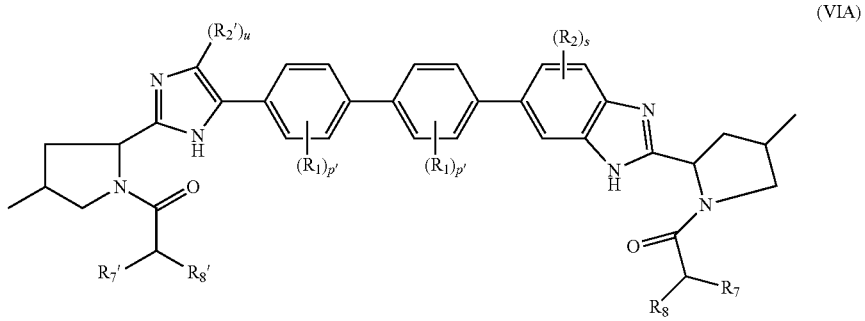

(VIA)

or a pharmaceutically acceptable salt thereof wherein each p' is independently 0, 1 or 2;

R$_7$ and R$_7'$ are each independently $C_{1-8}$ alkyl which is unsubstituted or substituted one or more times by R$^{10}$, $C_{2-8}$ alkenyl which is unsubstituted or substituted one or more times by R$^{10}$, $C_{2-8}$ alkynyl which is unsubstituted or substituted one or more times by R$^{10}$, phenyl which is unsubstituted or substituted one or more times by R$^{11}$, benzyl which is unsubstituted or substituted one or more times by R$^{11}$, 5-6 membered heteroaryl which is unsubstituted or substituted one or more times by R$^{11}$, 6-7 membered heteroaralkyl which is unsubstituted or substituted one or more times by R$^{11}$, 3-6 membered heterocycle which is unsubstituted or substituted one or more times by R$^{12}$, or 4-7 membered heterocycle-alkyl which is unsubstituted or substituted one or more times by R$^{12}$; and R$_8$ and R$_8'$ are each independently —NR$_a$R$_b$, —NR$_a$C(=O)NR$_a$R$_b$, —NR$_b$C(=O)R$_a$, —NR$_a$C(=NR$_c$)NR$_a$R$_b$, —NR$_b$C(=O)OR$_a$, —NR$_b$SO$_2$R$_a$, or —NR$_b$SO$_2$NR$_a$R$_b$, wherein R$_a$-R$_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

22. The compound according to claim 20, wherein said compound is of formula (VIB):

(VIB)

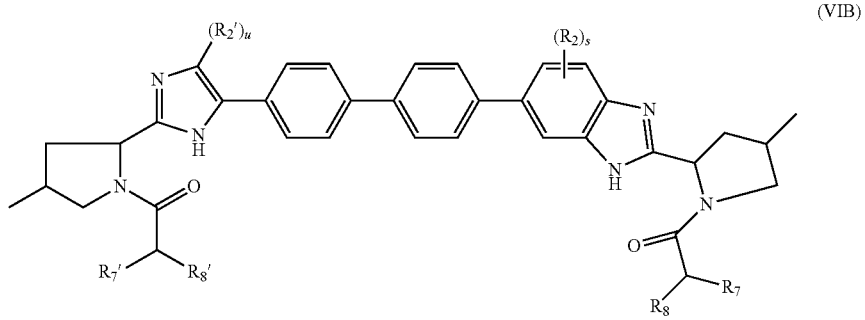

or a pharmaceutically acceptable salt thereof wherein $R_7$ and $R_7'$ are each independently $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 3-6 membered heterocycle which is unsubstituted or substituted one or more times by $R^{12}$, or 4-7 membered heterocycle-alkyl which is unsubstituted or substituted one or more times by $R^{12}$; and $R_8$ and $R_8'$ are each independently —$NR_aR_b$, —$NR_dC(=O)NR_aR_b$, —$NR_bC(=O)R_a$, —$NR_dC(=NR_c)NR_aR_b$, —$NR_bC(=O)OR_a$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

23. The compound according to claim 20, wherein said compound is of formula (VIIA):

or a pharmaceutically acceptable salt thereof wherein each p' is independently 0, 1 or 2;

$R_7$ and $R_7'$ are each independently $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 3-6 membered heterocycle which is unsubstituted or substituted one or more times by $R^{12}$, or 4-7 membered heterocycle-alkyl which is unsubstituted or substituted one or more times by $R^{12}$; and $R_8$ and $R_8'$ are each independently —$NR_aR_b$, —$NR_dC(=O)NR_aR_b$, —$NR_bC(=O)R_a$, —$NR_dC(=NR_c)NR_aR_b$, —$NR_bC(=O)OR_a$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

24. The compound according to claim 20, wherein said compound is of formula (VIIB):

(VIIA)

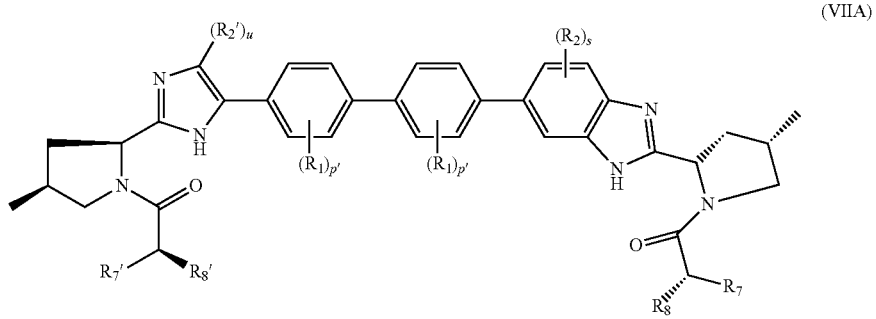

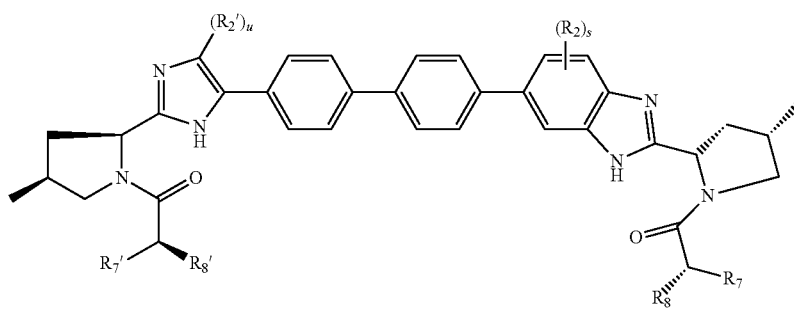

(VIIB)

or a pharmaceutically acceptable salt thereof wherein $R_7$ and $R_7'$ are each independently $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 3-6 membered heterocycle which is unsubstituted or substituted one or more times by $R^{12}$, or 4-7 membered heterocycle-alkyl which is unsubstituted or substituted one or more times by $R^{12}$; and $R_8$ and $R_8'$ are each independently —$NR_aR_b$, —$NR_dC(=O)NR_aR_b$, —$NR_bC(=O)R_a$, —$NR_dC(=NR_c)NR_aR_b$, —$NR_bC(=O)OR_a$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

25. A compound represented by a structural formula selected from the group consisting of:

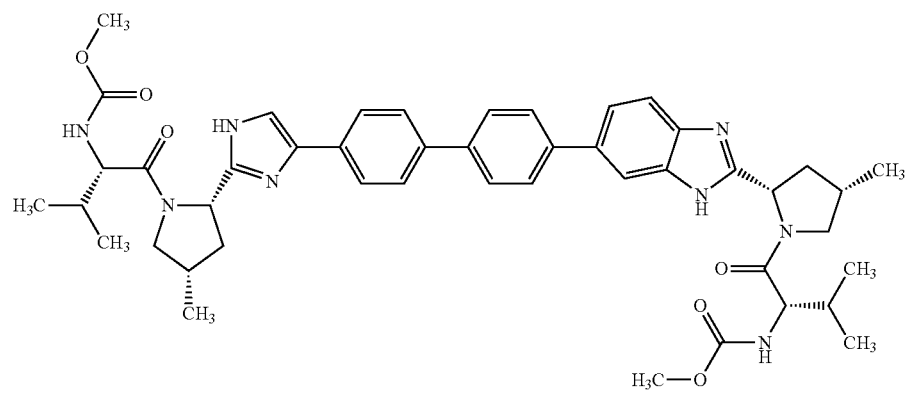 [SMILES: COC(=O)N[C@H](C(=O)N1C[C@@H](C)C[C@H]1c1nc(-c2ccc(-c3ccc(-c4ccc5nc([C@@H]6C[C@H](C)CN6C(=O)[C@@H](NC(=O)OC)C(C)C)[nH]c5c4)cc3)cc2)c[nH]1)C(C)C]

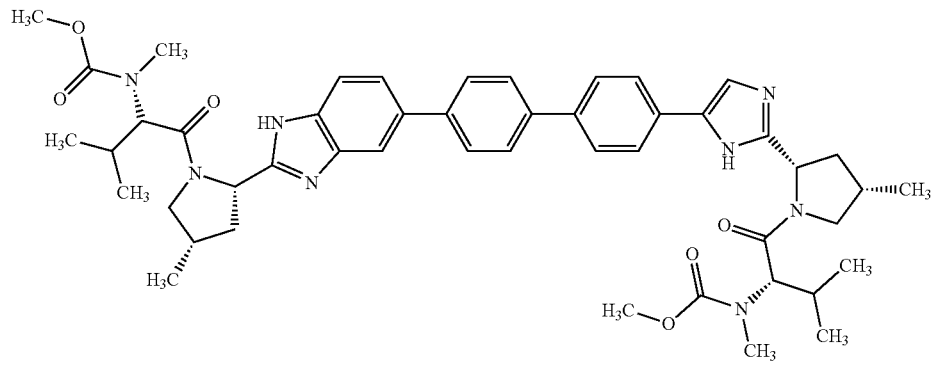

151 152
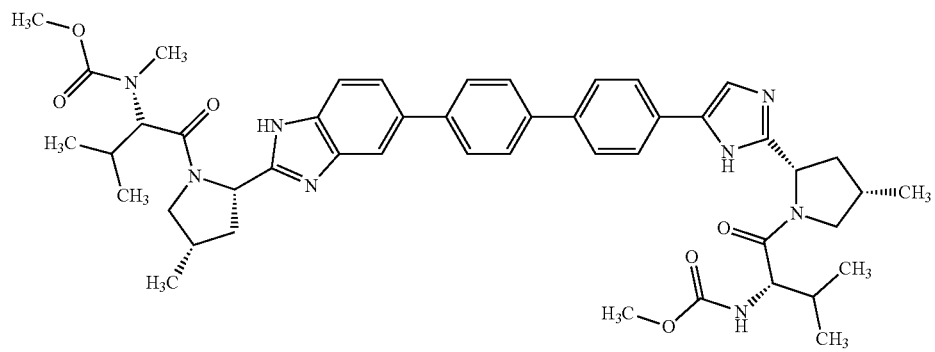
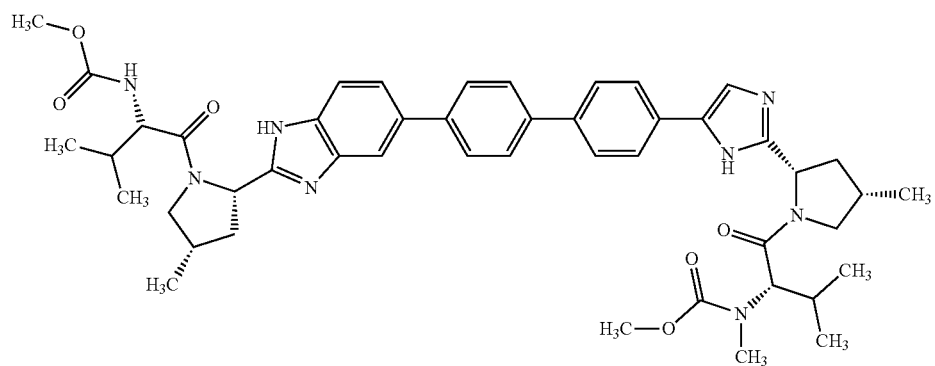
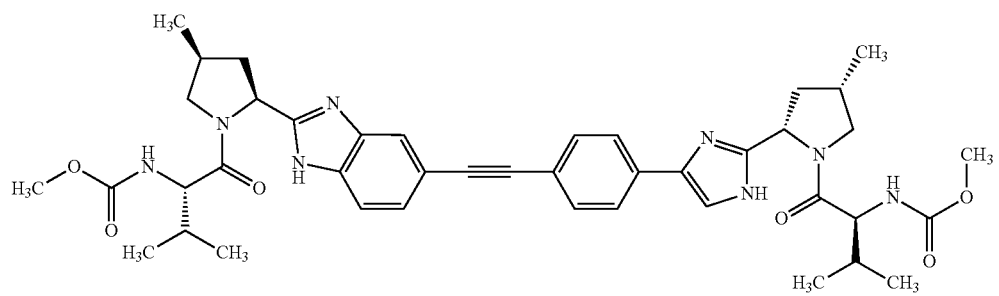
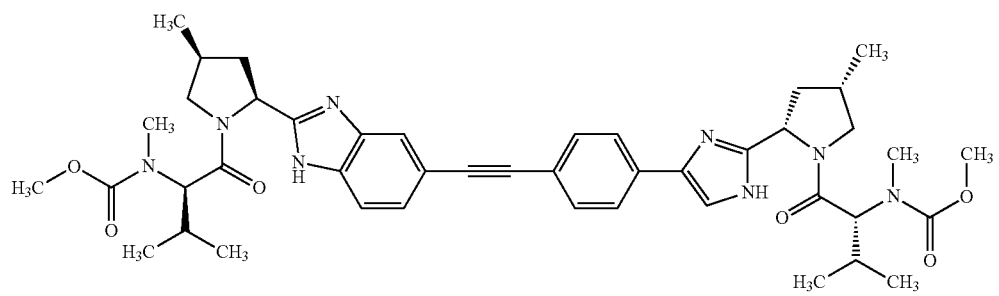

153 154
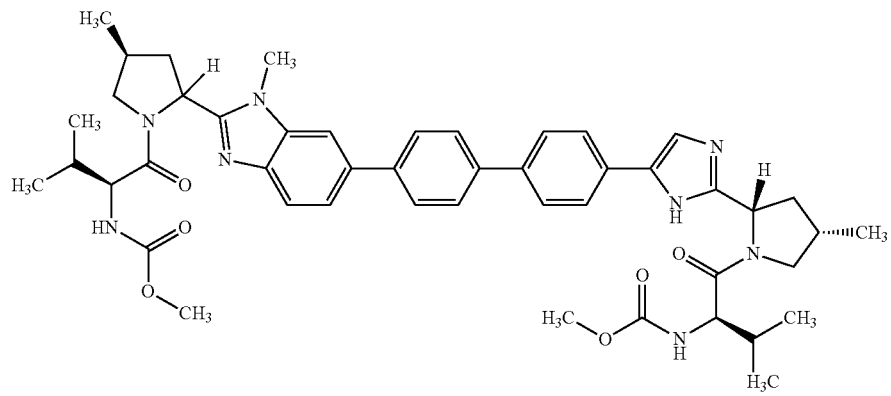 [SMILES: COC(=O)N[C@H](C(=O)N1C[C@@H](C)CC1c1nc2ccc(-c3ccc(-c4ccc(-c5cnc([C@@H]6C[C@H](C)CN6C(=O)[C@H](NC(=O)OC)C(C)C)[nH]5)cc4)cc3)cc2n1C)C(C)C]
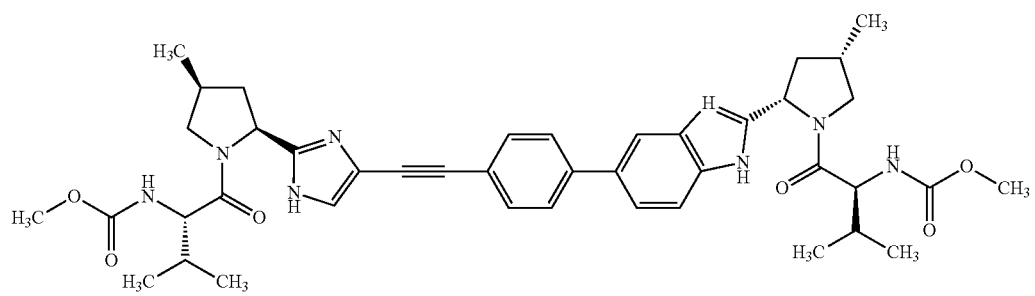
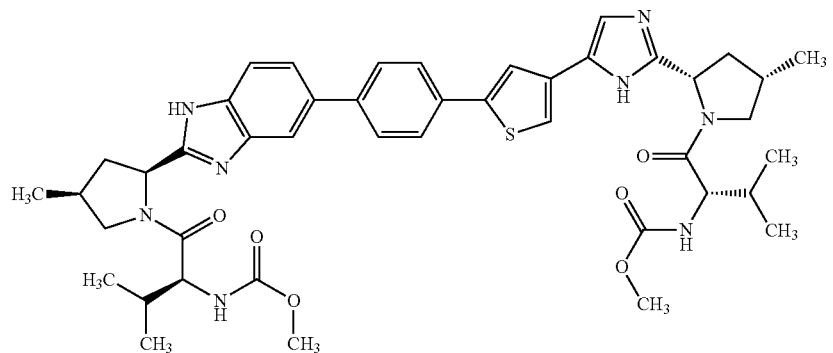
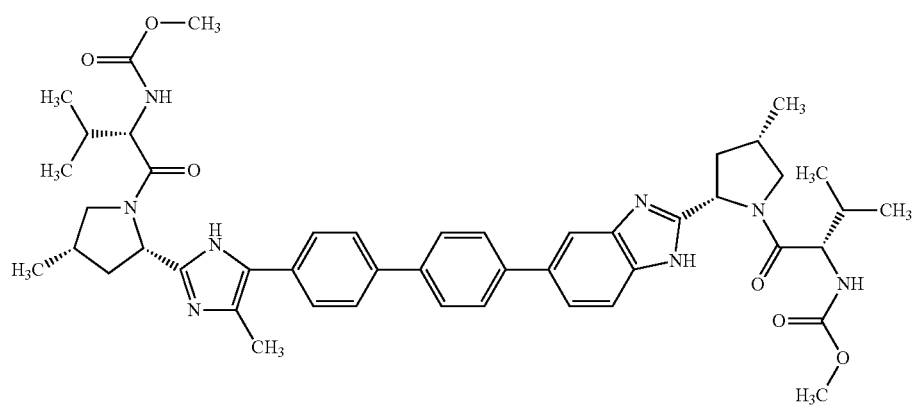 [SMILES: COC(=O)N[C@H](C(=O)N1C[C@@H](C)C[C@H]1c1nc(C)c(-c2ccc(-c3ccc(-c4ccc5[nH]c([C@@H]6C[C@H](C)CN6C(=O)[C@@H](NC(=O)OC)C(C)C)nc5c4)cc3)cc2)[nH]1)C(C)C]

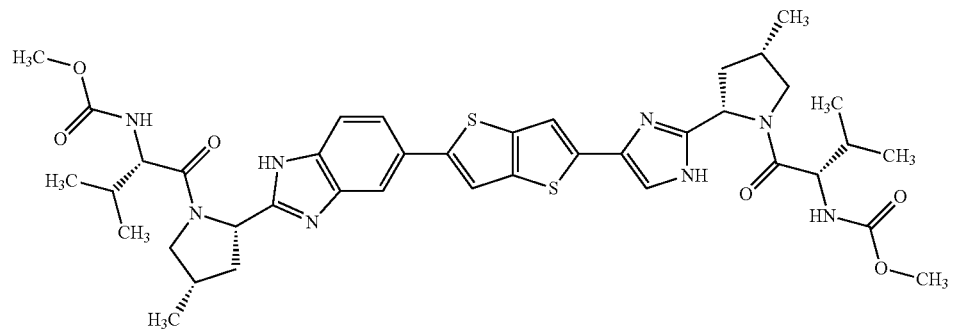
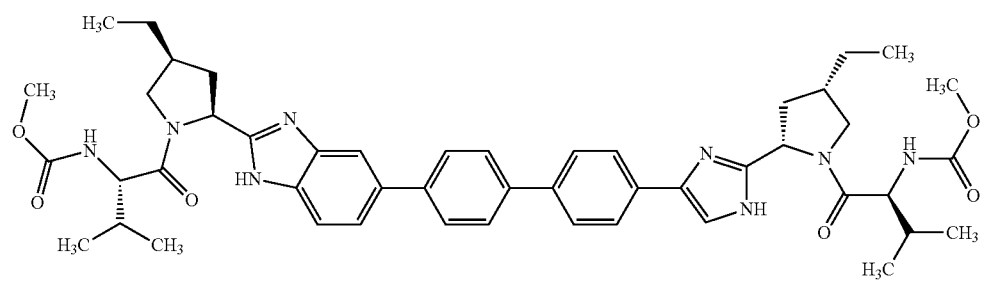 [SMILES: CC[C@H]1C[C@@H](c2nc(-c3ccc(-c4ccc(-c5ccc6[nH]c([C@@H]7C[C@H](CC)CN7C(=O)[C@@H](NC(=O)OC)C(C)C)nc6c5)cc4)cc3)c[nH]2)N(C(=O)[C@@H](NC(=O)OC)C(C)C)C1]
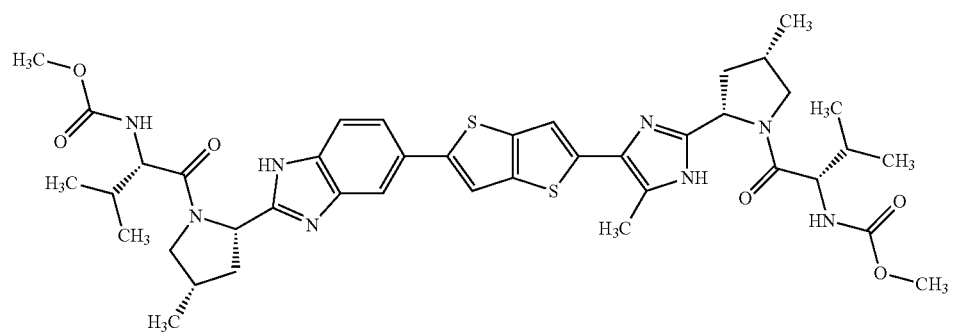
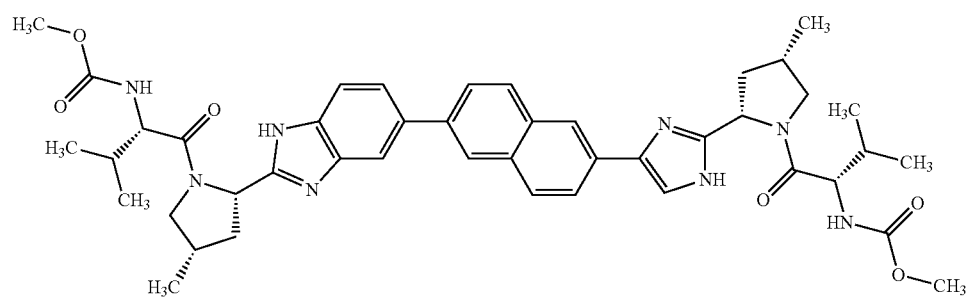

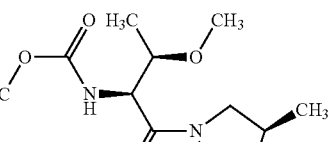
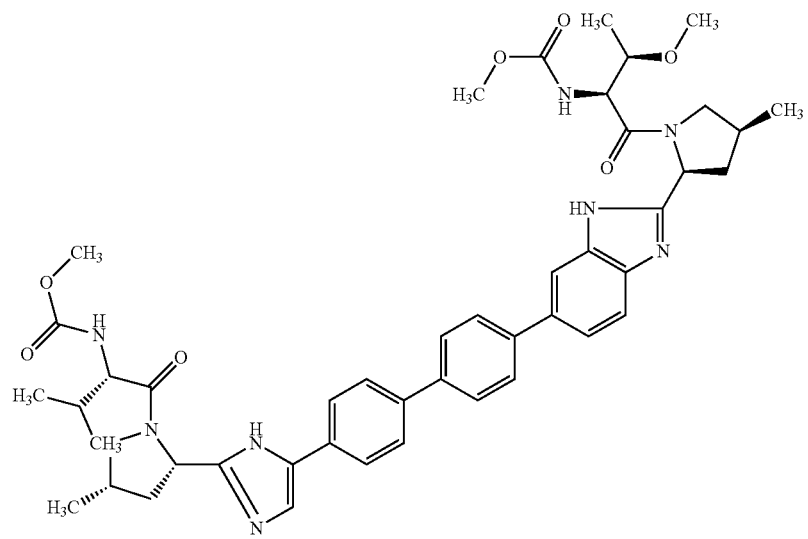
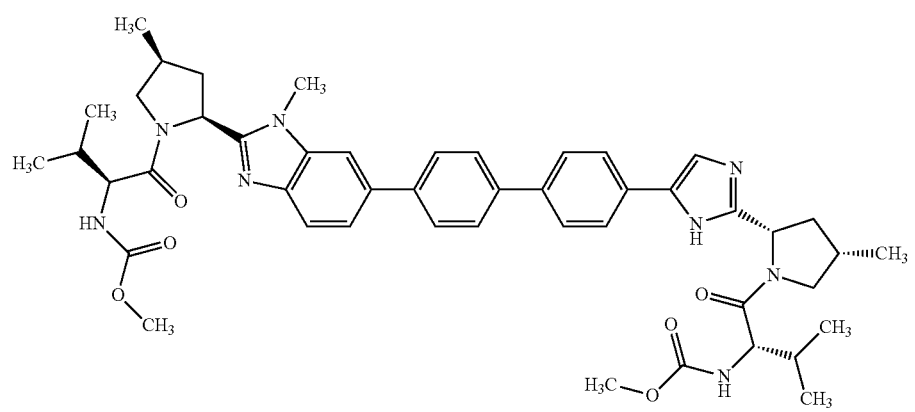 [SMILES: COC(=O)N[C@H](C(=O)N1C[C@@H](C)C[C@H]1c1ncc(-c2ccc(-c3ccc(-c4ccc5nc([C@@H]6C[C@H](C)CN6C(=O)[C@@H](NC(=O)OC)C(C)C)n(C)c5c4)cc3)cc2)[nH]1)C(C)C]
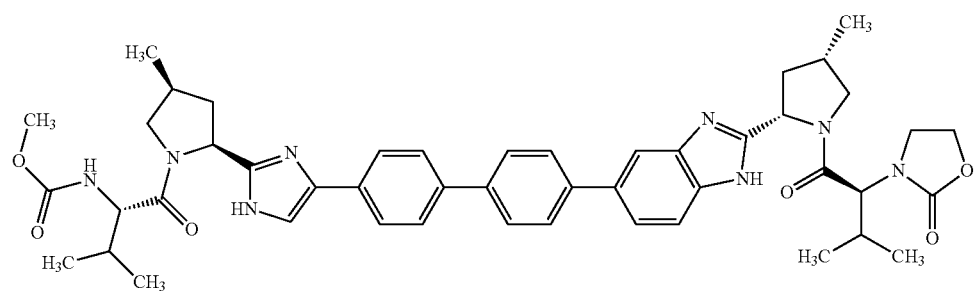 [SMILES: COC(=O)N[C@H](C(=O)N1C[C@@H](C)C[C@H]1c1nc(-c2ccc(-c3ccc(-c4ccc5[nH]c([C@@H]6C[C@H](C)CN6C(=O)[C@H](C(C)C)N6CCOC6=O)nc5c4)cc3)cc2)c[nH]1)C(C)C]

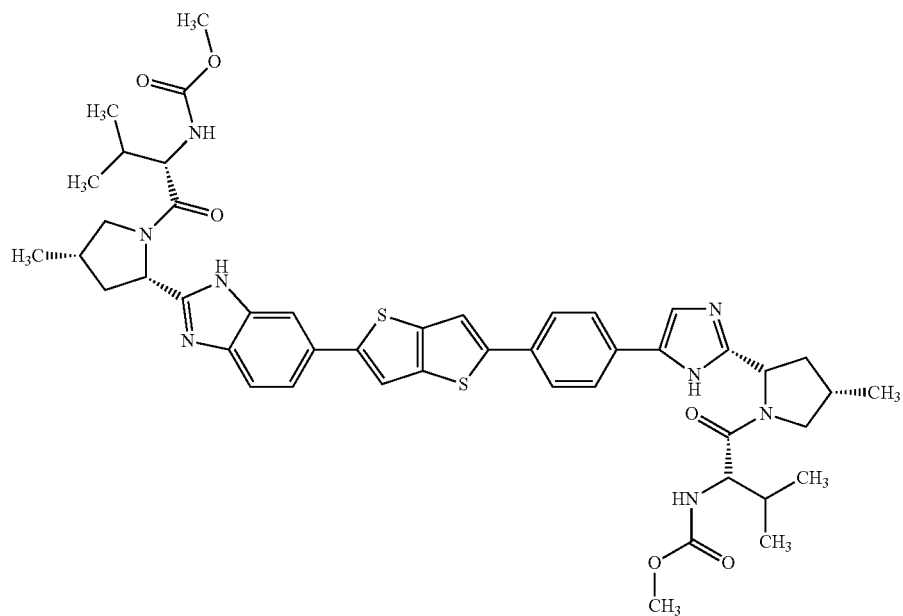
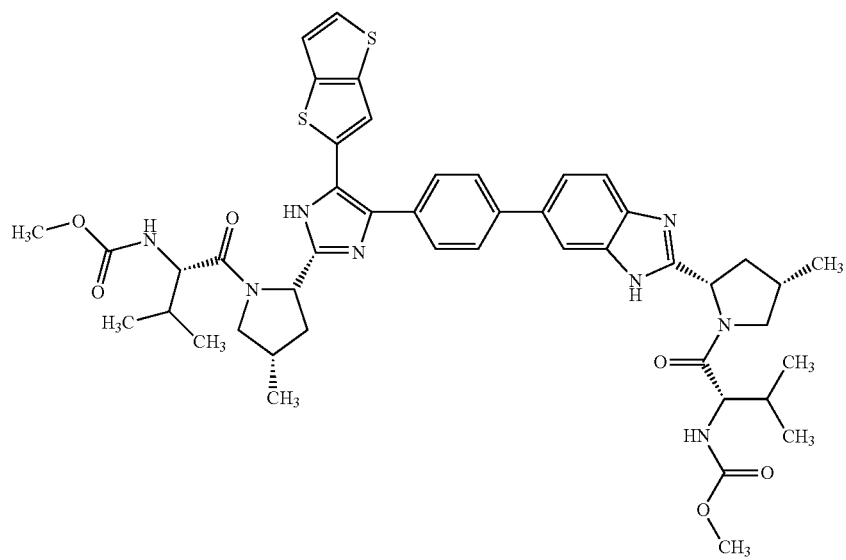

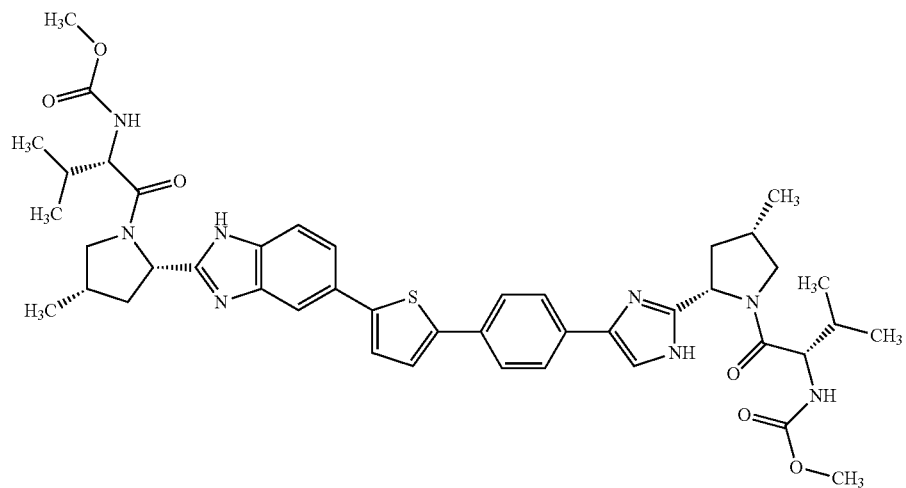 [SMILES: COC(=O)N[C@H](C(=O)N1C[C@@H](C)C[C@H]1c1nc(-c2ccc(-c3ccc(-c4ccc5[nH]c([C@@H]6C[C@H](C)CN6C(=O)[C@@H](NC(=O)OC)C(C)C)nc5c4)s3)cc2)c[nH]1)C(C)C]
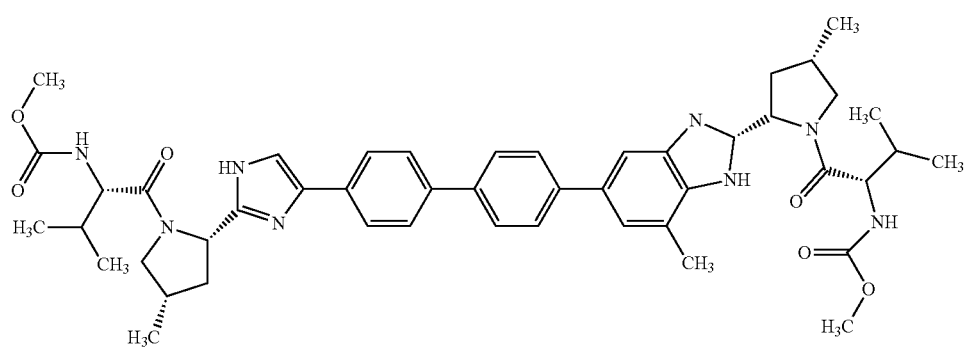 [SMILES: COC(=O)N[C@H](C(=O)N1C[C@@H](C)CC1[C@H]1Nc2cc(-c3ccc(-c4ccc(-c5c[nH]c([C@@H]6C[C@H](C)CN6C(=O)[C@@H](NC(=O)OC)C(C)C)n5)cc4)cc3)cc(C)c2N1)C(C)C]
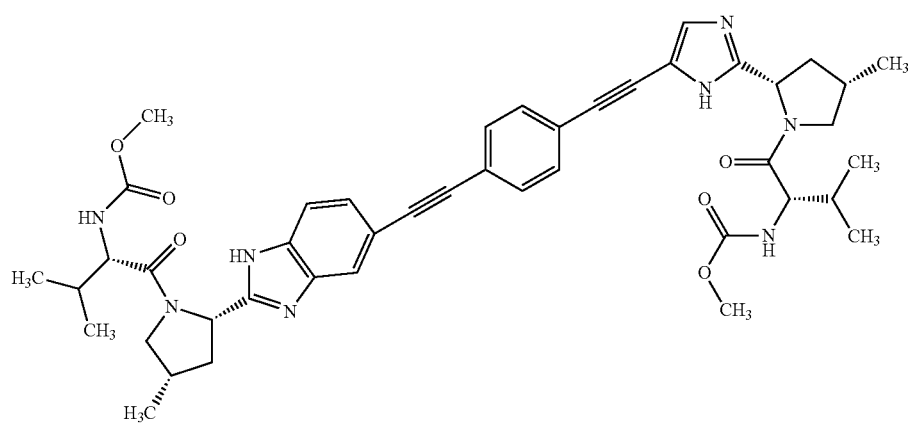 [SMILES: COC(=O)N[C@H](C(=O)N1C[C@@H](C)C[C@H]1c1ncc(C#Cc2ccc(C#Cc3ccc4[nH]c([C@@H]5C[C@H](C)CN5C(=O)[C@@H](NC(=O)OC)C(C)C)nc4c3)cc2)[nH]1)C(C)C]

163 164
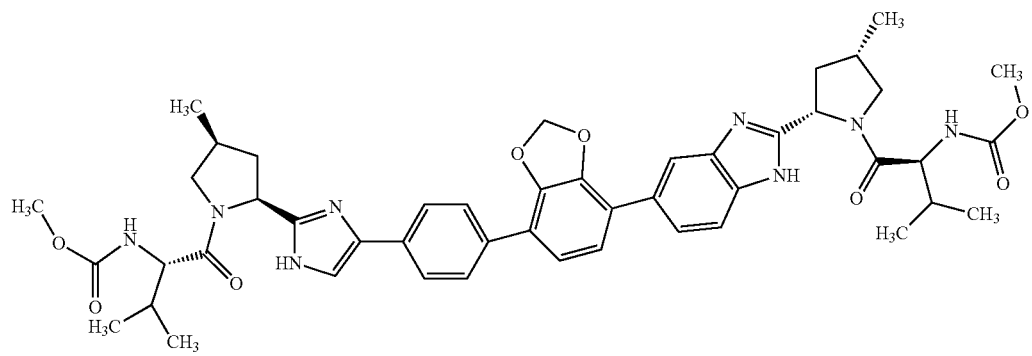 [SMILES: COC(=O)N[C@H](C(=O)N1C[C@@H](C)C[C@H]1c1nc(-c2ccc(-c3ccc(-c4ccc5[nH]c([C@@H]6C[C@H](C)CN6C(=O)[C@@H](NC(=O)OC)C(C)C)nc5c4)c4c3OCO4)cc2)c[nH]1)C(C)C]
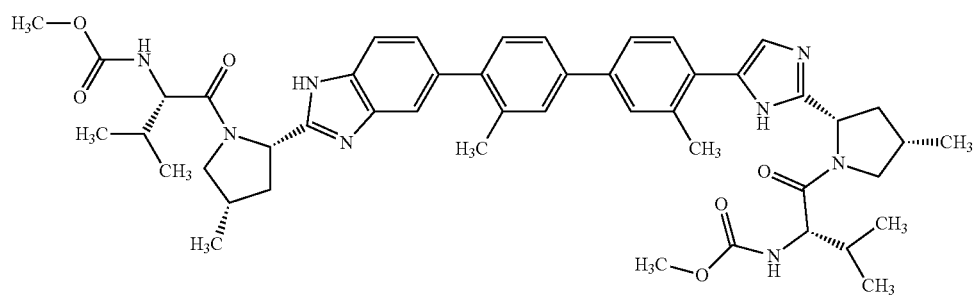
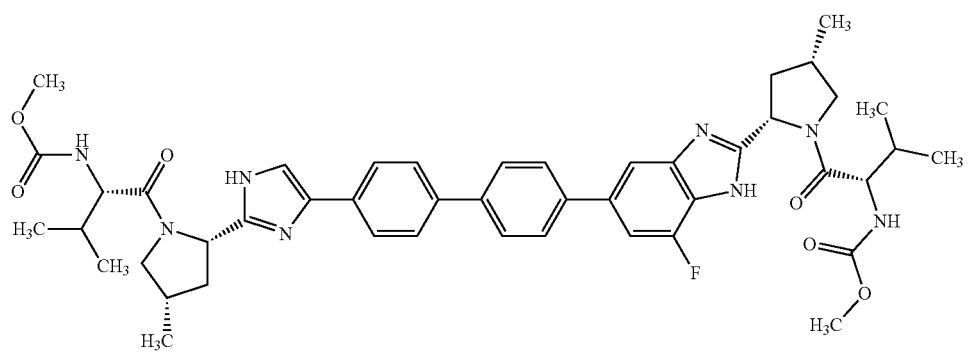 [SMILES: COC(=O)N[C@H](C(=O)N1C[C@@H](C)C[C@H]1c1nc(-c2ccc(-c3ccc(-c4cc(F)c5[nH]c([C@@H]6C[C@H](C)CN6C(=O)[C@@H](NC(=O)OC)C(C)C)nc5c4)cc3)cc2)c[nH]1)C(C)C]

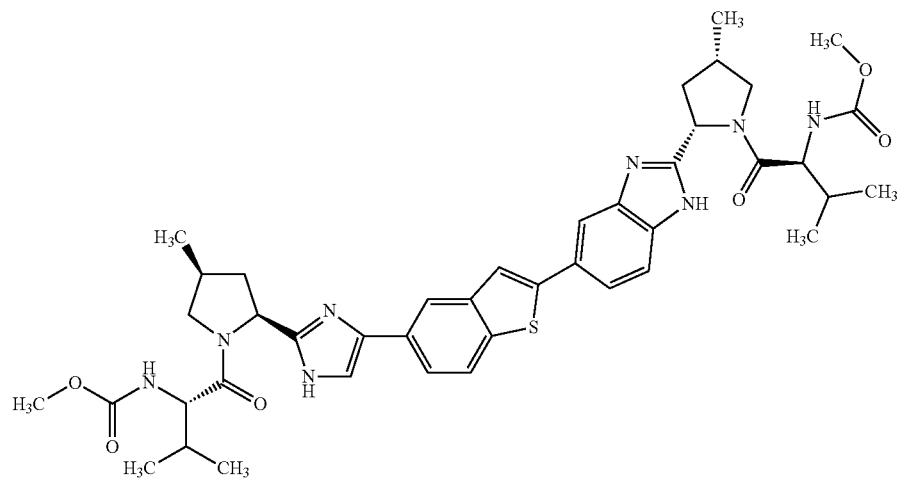 [SMILES: COC(=O)N[C@H](C(=O)N1C[C@@H](C)C[C@H]1c1nc(-c2ccc3sc(-c4ccc5[nH]c([C@@H]6C[C@H](C)CN6C(=O)[C@@H](NC(=O)OC)C(C)C)nc5c4)cc3c2)c[nH]1)C(C)C]
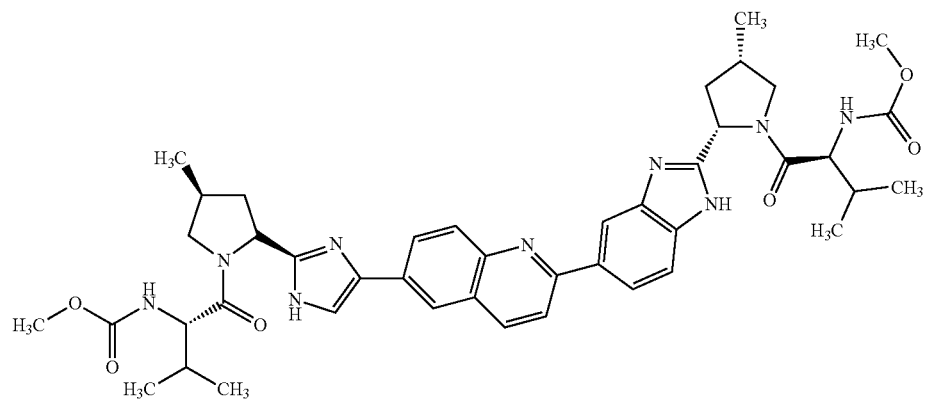
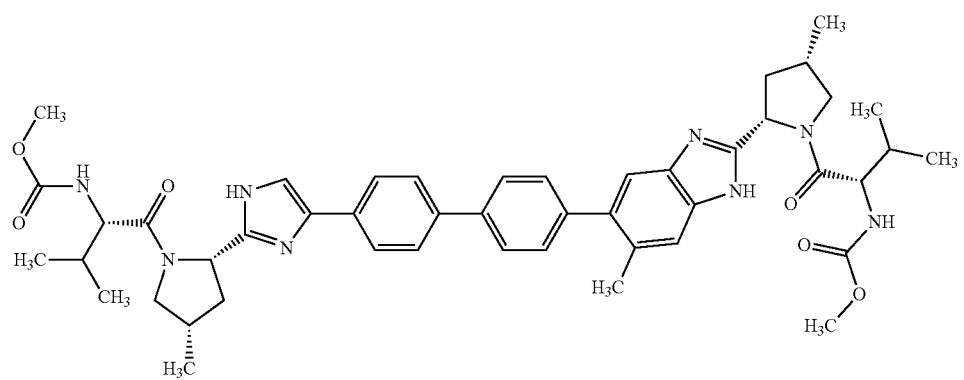 [SMILES: COC(=O)N[C@H](C(=O)N1C[C@@H](C)C[C@H]1c1nc(-c2ccc(-c3ccc(-c4cc5nc([C@@H]6C[C@H](C)CN6C(=O)[C@@H](NC(=O)OC)C(C)C)[nH]c5cc4C)cc3)cc2)c[nH]1)C(C)C]

167                                                                                          168
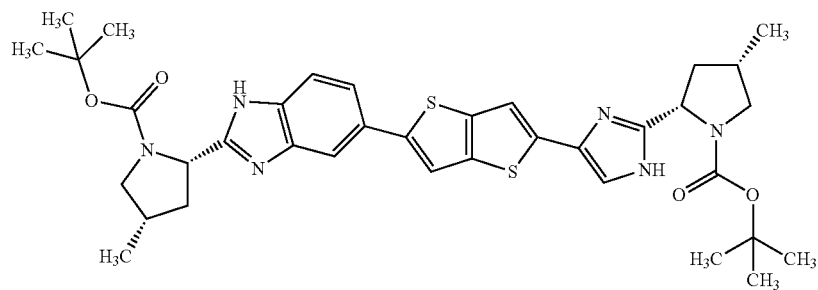 [SMILES: C[C@H]1C[C@@H](c2nc(-c3cc4sc(-c5ccc6[nH]c([C@@H]7C[C@H](C)CN7C(=O)OC(C)(C)C)nc6c5)cc4s3)c[nH]2)N(C(=O)OC(C)(C)C)C1]
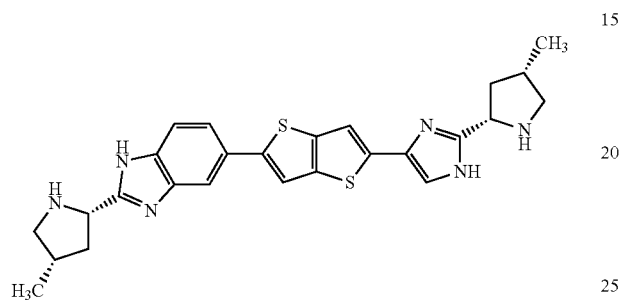
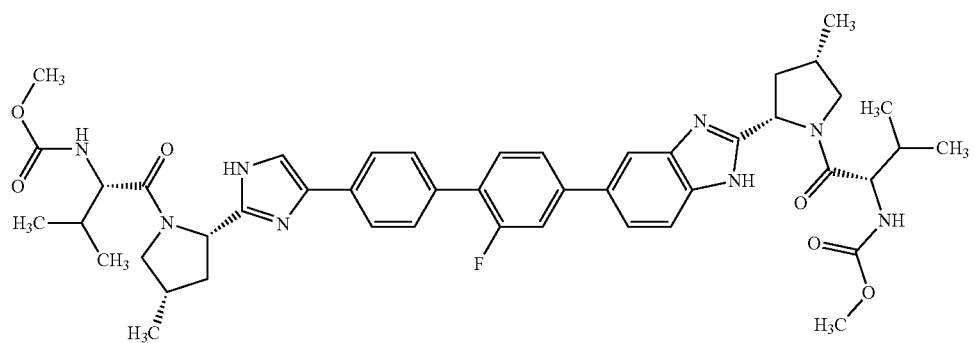
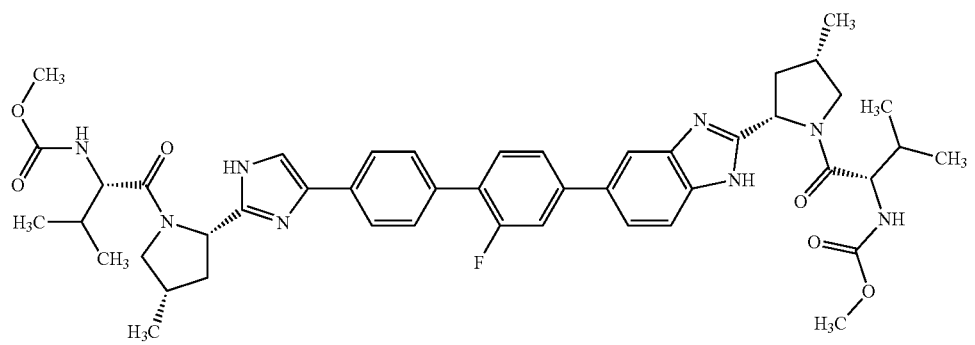 [SMILES: COC(=O)N[C@H](C(=O)N1C[C@@H](C)C[C@H]1c1nc(-c2ccc(-c3ccc(-c4ccc5[nH]c([C@@H]6C[C@H](C)CN6C(=O)[C@@H](NC(=O)OC)C(C)C)nc5c4)cc3F)cc2)c[nH]1)C(C)C]

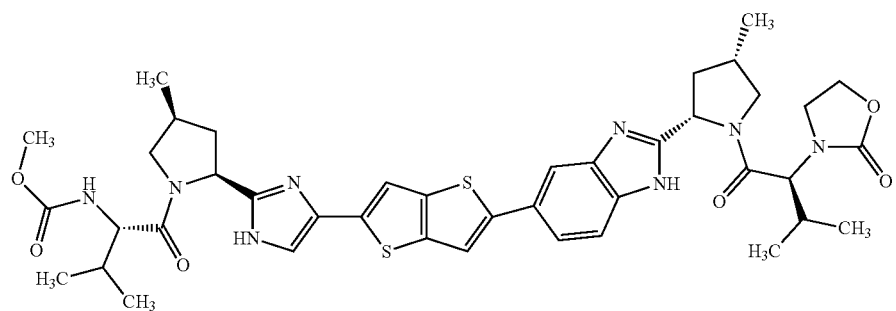 [SMILES: COC(=O)N[C@H](C(=O)N1C[C@@H](C)C[C@H]1c1nc(-c2cc3sc(-c4ccc5[nH]c([C@@H]6C[C@H](C)CN6C(=O)[C@H](C(C)C)N6CCOC6=O)nc5c4)cc3s2)c[nH]1)C(C)C]
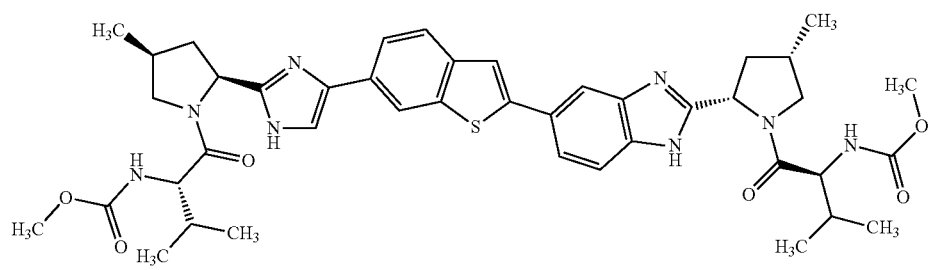 [SMILES: COC(=O)N[C@H](C(=O)N1C[C@@H](C)C[C@H]1c1nc(-c2ccc3cc(-c4ccc5[nH]c([C@@H]6C[C@H](C)CN6C(=O)[C@@H](NC(=O)OC)C(C)C)nc5c4)sc3c2)c[nH]1)C(C)C]
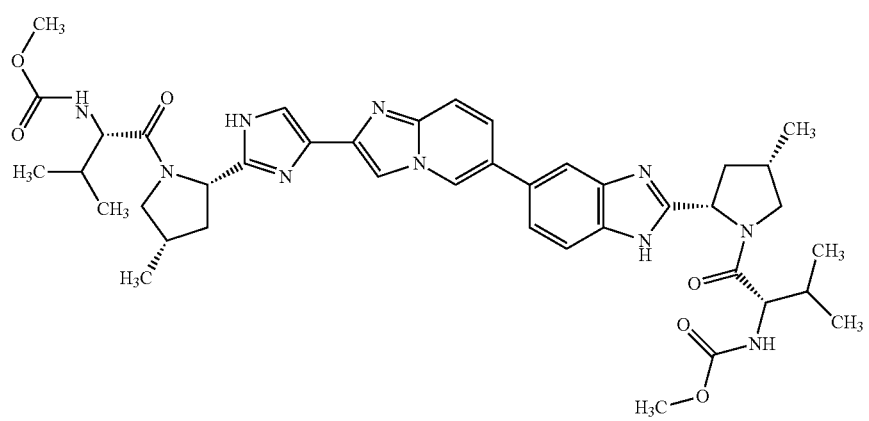 [SMILES: COC(=O)N[C@H](C(=O)N1C[C@@H](C)C[C@H]1c1nc(-c2cn3cc(-c4ccc5[nH]c([C@@H]6C[C@H](C)CN6C(=O)[C@@H](NC(=O)OC)C(C)C)nc5c4)ccc3n2)c[nH]1)C(C)C]
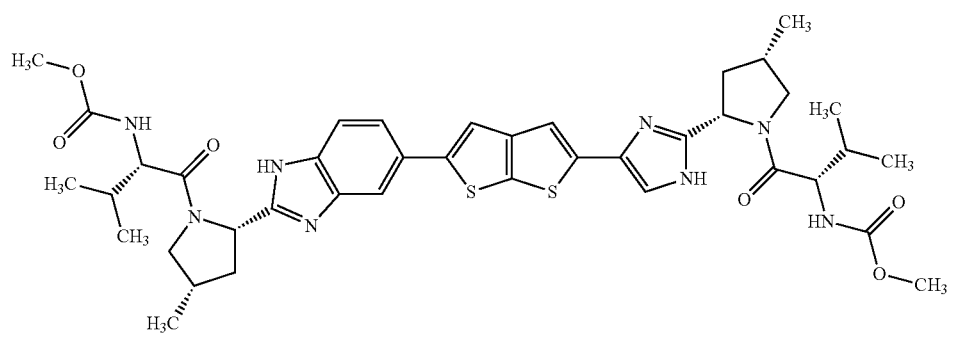

171 172
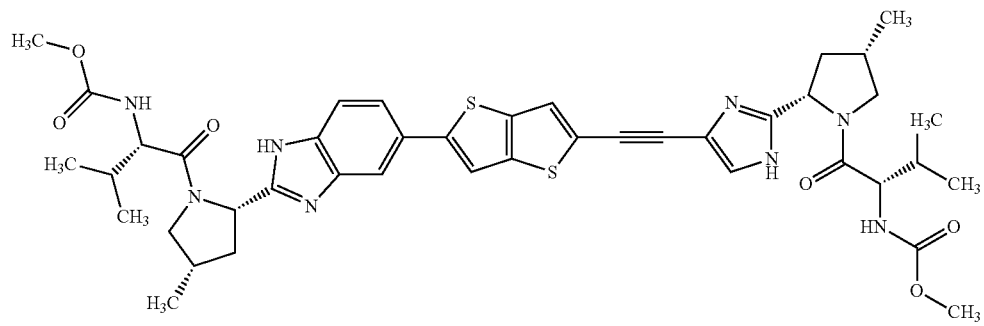 [SMILES: COC(=O)N[C@H](C(=O)N1C[C@@H](C)C[C@H]1c1nc(C#Cc2cc3sc(-c4ccc5[nH]c([C@@H]6C[C@H](C)CN6C(=O)[C@@H](NC(=O)OC)C(C)C)nc5c4)cc3s2)c[nH]1)C(C)C]
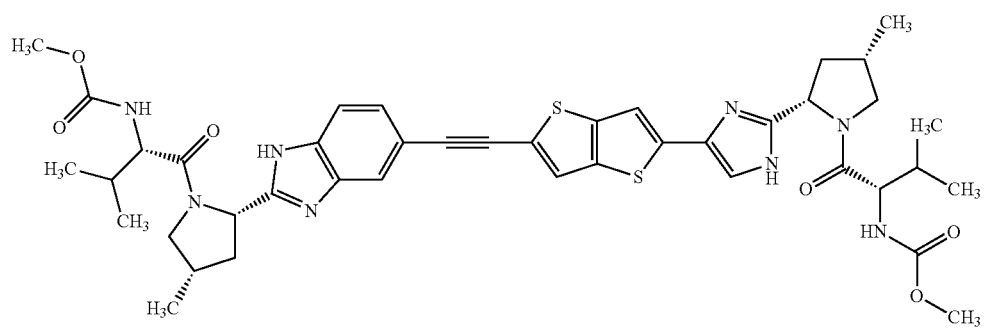 [SMILES: COC(=O)N[C@H](C(=O)N1C[C@@H](C)C[C@H]1c1nc(-c2cc3sc(C#Cc4ccc5[nH]c([C@@H]6C[C@H](C)CN6C(=O)[C@@H](NC(=O)OC)C(C)C)nc5c4)cc3s2)c[nH]1)C(C)C]
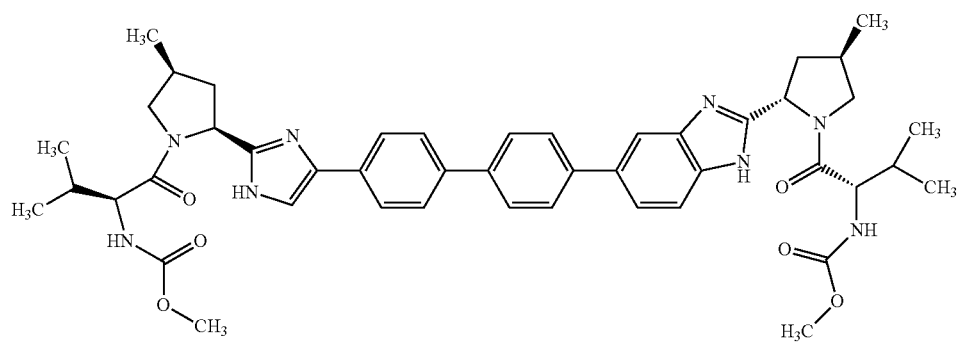 [SMILES: COC(=O)N[C@H](C(=O)N1C[C@@H](C)C[C@H]1c1nc(-c2ccc(-c3ccc(-c4ccc5[nH]c([C@@H]6C[C@@H](C)CN6C(=O)[C@@H](NC(=O)OC)C(C)C)nc5c4)cc3)cc2)c[nH]1)C(C)C]
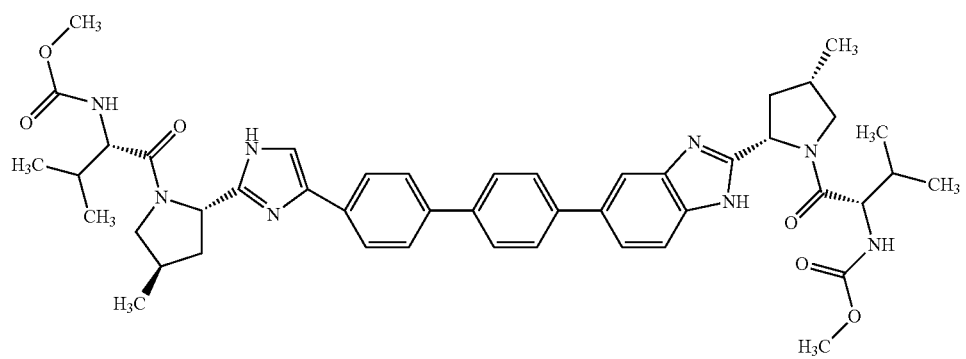 [SMILES: COC(=O)N[C@H](C(=O)N1C[C@H](C)C[C@H]1c1nc(-c2ccc(-c3ccc(-c4ccc5[nH]c([C@@H]6C[C@H](C)CN6C(=O)[C@@H](NC(=O)OC)C(C)C)nc5c4)cc3)cc2)c[nH]1)C(C)C]

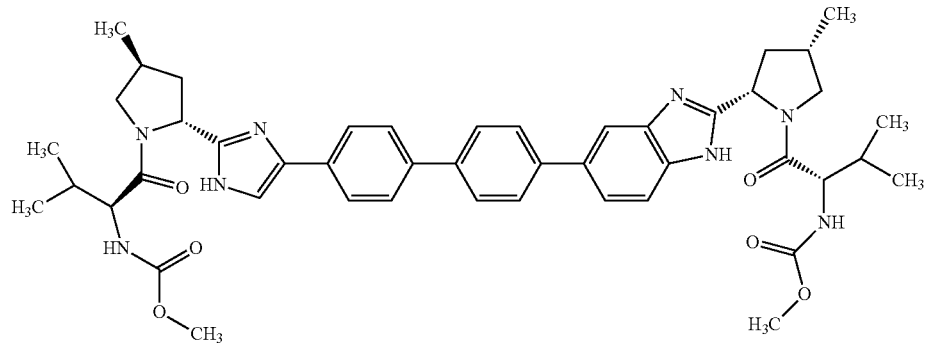 [SMILES: COC(=O)N[C@H](C(=O)N1C[C@@H](C)C[C@@H]1c1nc(-c2ccc(-c3ccc(-c4ccc5[nH]c([C@@H]6C[C@H](C)CN6C(=O)[C@@H](NC(=O)OC)C(C)C)nc5c4)cc3)cc2)c[nH]1)C(C)C]
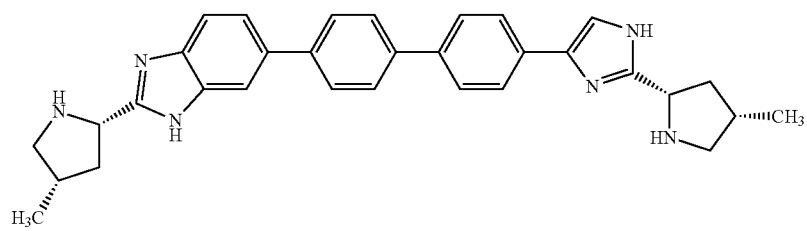 [SMILES: C[C@@H]1CN[C@H](c2nc(-c3ccc(-c4ccc(-c5ccc6nc([C@@H]7C[C@H](C)CN7)[nH]c6c5)cc4)cc3)c[nH]2)C1]
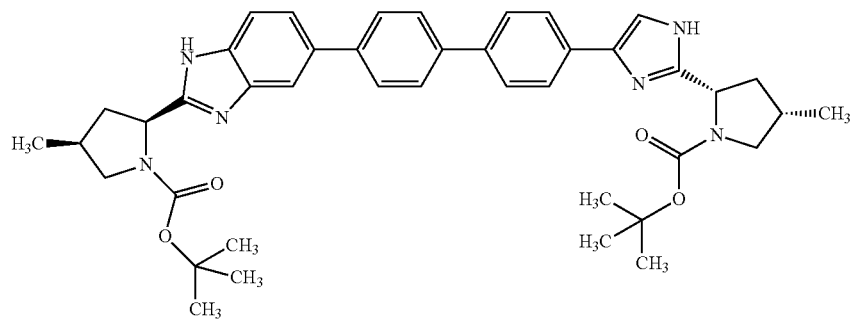
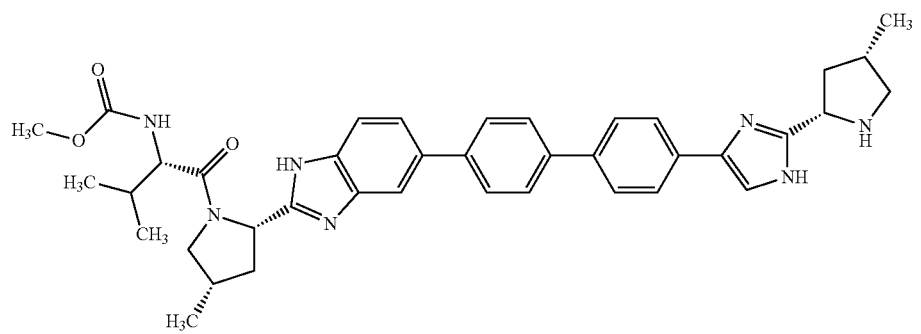 [SMILES: COC(=O)N[C@H](C(=O)N1C[C@@H](C)C[C@H]1c1nc2cc(-c3ccc(-c4ccc(-c5c[nH]c([C@@H]6C[C@H](C)CN6)n5)cc4)cc3)ccc2[nH]1)C(C)C]

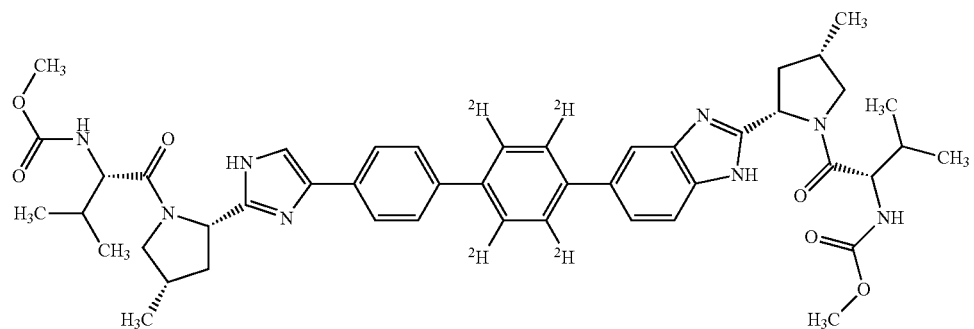 [SMILES: [2H]c1c([2H])c(-c2ccc3[nH]c([C@@H]4C[C@H](C)CN4C(=O)[C@@H](NC(=O)OC)C(C)C)nc3c2)c([2H])c([2H])c1-c1ccc(-c2c[nH]c([C@@H]3C[C@H](C)CN3C(=O)[C@@H](NC(=O)OC)C(C)C)n2)cc1]
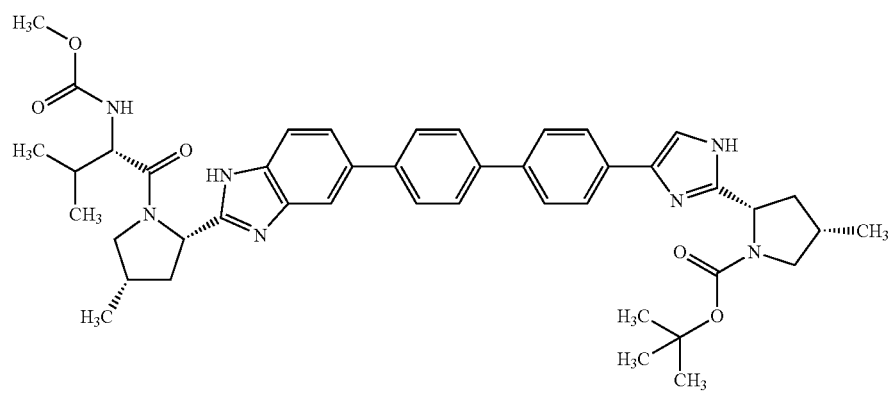 [SMILES: COC(=O)N[C@H](C(=O)N1C[C@@H](C)C[C@H]1c1nc2cc(-c3ccc(-c4ccc(-c5c[nH]c([C@@H]6C[C@H](C)CN6C(=O)OC(C)(C)C)n5)cc4)cc3)ccc2[nH]1)C(C)C]
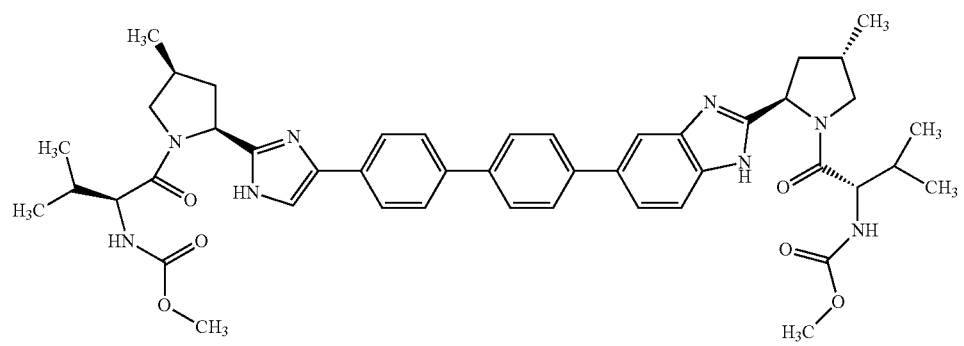 [SMILES: COC(=O)N[C@H](C(=O)N1C[C@@H](C)C[C@@H]1c1nc2cc(-c3ccc(-c4ccc(-c5c[nH]c([C@@H]6C[C@H](C)CN6C(=O)[C@@H](NC(=O)OC)C(C)C)n5)cc4)cc3)ccc2[nH]1)C(C)C]
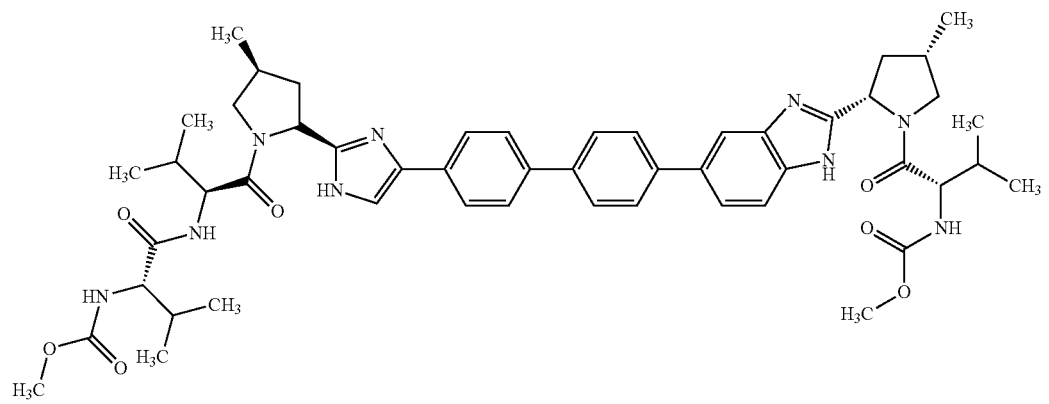

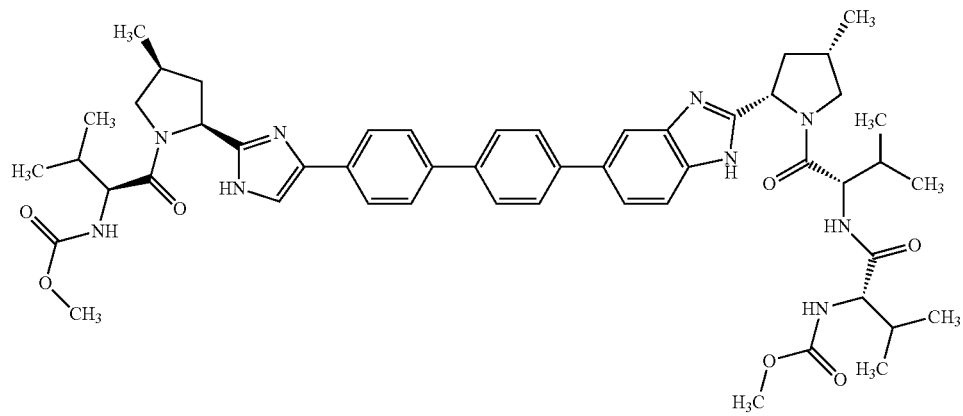 [SMILES: COC(=O)N[C@H](C(=O)N[C@H](C(=O)N1C[C@@H](C)C[C@H]1c1nc2cc(-c3ccc(-c4ccc(-c5c[nH]c([C@@H]6C[C@H](C)CN6C(=O)[C@@H](NC(=O)OC)C(C)C)n5)cc4)cc3)ccc2[nH]1)C(C)C)C(C)C]

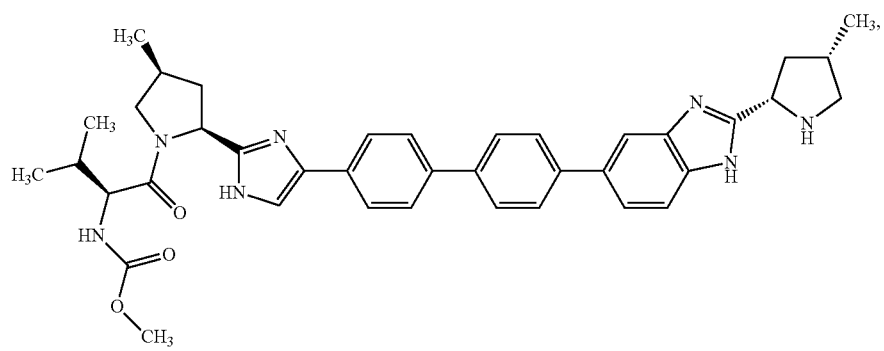 [SMILES: COC(=O)N[C@H](C(=O)N1C[C@@H](C)C[C@H]1c1nc(-c2ccc(-c3ccc(-c4ccc5[nH]c([C@@H]6C[C@H](C)CN6)nc5c4)cc3)cc2)c[nH]1)C(C)C]

or a pharmaceutically acceptable salt thereof.

26. A pharmaceutical composition comprising at least one compound according to claim 1 and at least one pharmaceutically acceptable carrier or excipient.

27. A method of treating infection by a HCV virus, comprising contacting a biological sample or administering to a patient in need thereof a compound of claim 1 in an amount effective to treat the infection.

* * * * *